(12) United States Patent
Rajashekara et al.

(10) Patent No.: US 12,161,630 B2
(45) Date of Patent: Dec. 10, 2024

(54) METHODS TO CONTROL INFECTION USING NEW GENERATION SMALL MOLECULE GROWTH INHIBITORS

(71) Applicant: Ohio State Innovation Foundation, Columbus, OH (US)

(72) Inventors: Gireesh Rajashekara, Wooster, OH (US); Loic Deblais, Wooster, OH (US); Yosra A. Helmy, Wooster, OH (US); Dipak Kathayat, Wooster, OH (US); Sally A. Miller, Wooster, OH (US)

(73) Assignee: Ohio State Innovation Foundation, Columbus, OH (US)

(*) Notice: Subject to any disclaimer, the term of this patent is extended or adjusted under 35 U.S.C. 154(b) by 0 days.

(21) Appl. No.: 17/938,872

(22) Filed: Oct. 7, 2022

(65) Prior Publication Data
US 2023/0094112 A1     Mar. 30, 2023

Related U.S. Application Data

(63) Continuation of application No. 16/955,603, filed as application No. PCT/US2018/066767 on Dec. 20, 2018, now Pat. No. 11,478,454.

(60) Provisional application No. 62/608,335, filed on Dec. 20, 2017.

(51) Int. Cl.

| | |
|---|---|
| *A61K 31/4184* | (2006.01) |
| *A01N 43/50* | (2006.01) |
| *A01N 43/52* | (2006.01) |
| *A01N 47/44* | (2006.01) |
| *A23K 20/111* | (2016.01) |
| *A23K 20/137* | (2016.01) |
| *A23K 20/195* | (2016.01) |
| *A23K 50/75* | (2016.01) |
| *A61K 9/00* | (2006.01) |
| *A61K 31/155* | (2006.01) |
| *A61K 31/407* | (2006.01) |
| *A61K 31/4164* | (2006.01) |
| *A61K 31/496* | (2006.01) |
| *A61K 31/546* | (2006.01) |
| *A61P 31/04* | (2006.01) |

(52) U.S. Cl.
CPC .......... *A61K 31/4184* (2013.01); *A01N 43/50* (2013.01); *A01N 43/52* (2013.01); *A01N 47/44* (2013.01); *A23K 20/111* (2016.05); *A23K 20/137* (2016.05); *A23K 20/195* (2016.05); *A23K 50/75* (2016.05); *A61K 9/0053* (2013.01); *A61K 31/155* (2013.01); *A61K 31/407* (2013.01); *A61K 31/4164* (2013.01); *A61K 31/496* (2013.01); *A61K 31/546* (2013.01); *A61P 31/04* (2018.01)

(58) Field of Classification Search
CPC ................................................. A61K 31/4184
See application file for complete search history.

(56) References Cited

U.S. PATENT DOCUMENTS

| | | | |
|---|---|---|---|
| 11,478,454 B2* | 10/2022 | Rajashekara | ......... A01N 43/50 |
| 2012/0171129 A1 | 7/2012 | Melander et al. | |
| 2014/0079808 A1 | 3/2014 | Lindsey et al. | |
| 2014/0212374 A1 | 7/2014 | Kim et al. | |
| 2014/0364474 A1 | 12/2014 | Melander et al. | |
| 2016/0326174 A1 | 11/2016 | Rajashekara et al. | |
| 2017/0342025 A1 | 11/2017 | Potter et al. | |
| 2019/0373890 A1 | 12/2019 | Huigens, III | |

OTHER PUBLICATIONS

Kathayat et al., "Novel small molecule growth inhibitor affecting bacterial outer membrane reduces extraintestinal pathogenic *Escherichia coli* (ExPEC) infection in avian model", 2021, Microbiol. Spectr., 9(2), pp. 1-23 (e00006-21; https://doi.org/10.1128/Spectrum.00006-21). (Year: 2021).*
International Search Report and Written Opinion issued by the International Searching Authority (ISA/US) in PCT Application No. PCT/US2018/066767 on Dec. 20, 2018. 12 pages.
PUBCHEM CID 126957442, pp. 1-10, May 4, 2017.
PUBCHEM CID 2847561, pp. 1-11, Jul. 28, 2005.
Abouelhassan, Y. et al. Discovery of quinoline small molecules with potent dispersal activity against methicillin-resistant *Staphylococcus aureus* and *Staphylococcus epidermidis* biofilms using a scaffold hopping strategy. Bioorg. Med. Chem. Lett. 24, 5076-5080 (2014).
Anderl JN, Zahller J, Roe F, Stewart PS. 2003. Role of Nutrient Limitation and Stationary-Phase Existence in Klebsiella pneumoniae Biofilm Resistance to Ampicillin and Ciprofloxacin. Antimicrob Agents Chemother 47:1251-1256.
Andrews, J. Gut Bacteria on 97 Percent of Retail Chicken Breasts. Food Safety News (2013). Available at: http://www.foodsafetynews.com/2013/12/consumer-reports-gut-bacteria-on-97-percent-of-retail-chicken/ (Accessed: Jul. 11, 2018).
Antunes P, Mourão J, Campos J, Peixe L. 2016. Salmonellosis: the role of poultry meat. Clin Microbiol Infect 22:110-121.
Arlet, G et al. *Salmonella* resistant to extended-spectrum cephalosporins: prevalence and epidemiology. Microbes Infect. 8, 1945-1954 (2006).
Barba-Vidal, E. et al. The Probiotic Combination of *Bifidobacterium longum* subsp. infantis CECT 7210 and *Bifidobacterium animalis* subsp. lactis BPL6 Reduces Pathogen Loads and Improves Gut Health of Weaned Piglets Orally Challenged with *Salmonella* Typhimurium. Front. Microbiol. 8, 1570 (2017).
Basler C, Nguyen T-A, Anderson TC, Hancock T, Behravesh CB. 2016. Outbreaks of Human Salmonella Infections Associated with Live Poultry, United States, 1990-2014. Emerg Infect Dis 22:1705-1711.

(Continued)

*Primary Examiner* — Rei Tsang Shiao
(74) *Attorney, Agent, or Firm* — Meunier Carlin & Curfman LLC

(57) ABSTRACT

Disclosed herein are methods of treating a subject with a bacterial infection, or preventing a bacterial infection, comprising administering to the subject an effective amount of at least one compound, or a derivative thereof, having the formula of SM1, SM3, SM4, or SM5. Also described are methods of inhibiting bacterial growth in a plant comprising contacting the plant with an effective amount of at least one compound, or a derivative thereof, having the formula of SM1, SM3, SM4, or SM5. The methods are effective against an array of bacterial pathogens in various animals and plants.

24 Claims, 24 Drawing Sheets

(56) References Cited

OTHER PUBLICATIONS

Batz MB, Hoffmann S, Morris JG. 2012. Ranking the disease burden of 14 pathogens in food sources in the United States using attribution data from outbreak investigations and expert elicitation. J Food Prot 75:1278-1291.

Behravesh, C. Barton, et al. "Multistate outbreak of *Salmonella* serotype Typhimurium infections associated with consumption of restaurant tomatoes, USA, 2006: hypothesis generation through case exposures in multiple restaurant clusters." Epidemiology & Infection 140.11 (2012): 2053-2061.

Bolger AM, Lohse M, Usadel B. 2014. Trimmomatic: a flexible trimmer for Illumina sequence data. Bioinforma Oxf Engl 30:2114-2120.

Caporaso JG, Kuczynski J, Stombaugh J, Bittinger K, Bushman FD, Costello EK, Fierer N, Peña AG, Goodrich JK, Gordon JI, Huttley GA, Kelley ST, Knights D, Koenig JE, Ley RE, Lozupone CA, McDonald D, Muegge BD, Pirrung M, Reeder J, Sevinsky JR, Turnbaugh PJ, Walters WA, Widmann J, Yatsunenko T, Zaneveld J, Knight R. 2010. QIIME allows analysis of high-throughput community sequencing data. Nat Methods 7:335-336.

CDC. Biggest Threats | Antibiotic/Antimicrobial Resistance | CDC. Centers for Disease Control and Prevention Available at: https://www.cdc.gov/drugresistance/biggest_threats.html (Accessed: Jul. 20, 2018).

CDC. Keeping Backyard Poultry. Centers for Disease Control and Prevention Available at: https://www.cdc.gov/features/salmonellapoultry/index.html (Accessed: Jul. 20, 2018).

Coraça-Hubér, D. C., Fille, M., Hausdorfer, J., Pfaller, K. & Nogler, M. Evaluation of MBECTM-HTP biofilm model for studies of implant associated infections. J. Orthop. Res. 30, 1176-1180 (2012).

Dalebroux, Z. D. et al. Delivery of cardiolipins to the *Salmonella* outer membrane is necessary for survival within host tissues and virulence. Cell Host Microbe 17, 441-451 (2015).

Dalebroux, Z. D., Matamouros, S., Whittington, D., Bishop, R. E. & Miller, S. I. PhoPQ regulates acidic glycerophospholipid content of the *Salmonella* Typhimurium outer membrane. Proc. Natl. Acad. Sci. USA 111, 1963-1968 (2014).

De Keersmaecker, S. C. J et al. Strong antimicrobial activity of Lactobacillus rhamnosus GG against *Salmonella typhimurium* is due to accumulation of lactic acid. FEMS Microbiol. Lett. 259, 89-96 (2006).

Desbois AP, Coote PJ. 2011. Wax moth larva (*Galleria mellonella*): an in vivo model for assessing the efficacy of antistaphylococcal agents. J Antimicrob Chemother 66:1785-1790.

Desbois AP, Coote PJ. 2012. Utility of Greater Wax Moth Larva (*Galleria mellonella*) for Evaluating the Toxicity and Efficacy of New Antimicrobial Agents. Adv Appl Microbiol 78:25-53.

Doern CD. 2014. When does 2 plus 2 equal 5? A review of antimicrobial synergy testing. J Clin Microbiol 52:4124-4128.

Dougherty, T. J. & Pucci, M. J. Antibiotic Discovery and Development. (Springer Science & Business Media, 2011).

Eeckhaut V, Wang J, Van Parys A, Haesebrouck F, Joossens M, Falony G, Raes J, Ducatelle R, Van Immerseel F. 2016. The Probiotic Butyricicoccus pullicaecorum Reduces Feed Conversion and Protects from Potentially Harmful Intestinal Microorganisms and Necrotic Enteritis in Broilers. Front Microbiol 7, 1416.

Eisenstein M. 2016. Microbiome: Bacterial broadband. Nature 533:S104-S106.

Fernández-Rubio C, Ordóñez C, Abad-González J, Garcia-Gallego A, Honrubia MP, Mallo JJ, Balana-Fouce R. 2009. Butyric acid-based feed additives help protect broiler chickens from *Salmonella enteritidis* infection. Poult Sci 88:943-948.

Foley SL, Johnson TJ, Ricke SC, Nayak R, Danzeisen J. 2013. *Salmonella* Pathogenicity and Host Adaptation in Chicken-Associated Serovars. Microbiol Mol Biol Rev MMBR 77:582-607.

Foley SL, Nayak R, Hanning IB, Johnson TJ, Han J, Ricke SC. 2011. Population Dynamics of *Salmonella enterica* Serotypes in Commercial Egg and Poultry Production V . Appl Environ Microbiol 77:4273-4279.

Friedman, C. R. & Whitney, C. G. It's Time for a Change in Practice: Reducing Antibiotic Use Can Alter Antibiotic Resistance. J. Infect. Dis. 197, 1082-1083 (2008).

Goel, M. K., Khanna, P. & Kishore, J. Understanding survival analysis: Kaplan-Meier estimate. Int. J. Ayurveda Res. 1, 274-278 (2010).

Guo, Q. et al. Identification of a small molecule that simultaneously suppresses virulence and antibiotic resistance of Pseudomonas aeruginosa. Sci. Rep. 6, srep19141 (2016).

Gupta N, Pathak DP. 2011. Synthesis and Evaluation of N-substituted Imidazole Derivatives for Antimicrobial Activity. Indian J Pharm Sci 73:674-678.

Harris, Noreen V., Noel S. Weiss, and Charles M. Nolan. "The role of poultry and meats in the etiology of Campylobacter jejuni/coli enteritis." American Journal of Public Health 76.4 (1986): 407-411.

Harris, A. P. & Phillips, R. S. Benzimidazole analogs of 1-tryptophan are substrates and inhibitors of tryptophan indole lyase from *Escherichia coli*. FEBS J. 280 (2013).

Helmy, Y. A., Kassem, I. I., Kumar, A. & Rajashekara, G. In Vitro Evaluation of the Impact of the Probiotic *E. coli* Nissle 1917 on Campylobacter jejuni's Invasion and Intracellular Survival in Human Colonic Cells. Front. Microbiol. 8 (2017).

Hong-Geller, E., Micheva-Viteva, S. Small Molecule Screens to Identify Inhibitors of Infectious Disease. in Drug Discovery: InTech, ed. E. Shelmy Hany El, 157-175 (2013).

Cost Estimates of Foodborne Illnesses https://www.ers.usda.gov/data-products/cost-estimates-of-foodborne-illnesses/.

Kassem, I. I. et al. Respiratory proteins contribute differentially to Campylobacter jejuni's survival and in vitro interaction with hosts' intestinal cells. BMC Microbiol. 12, 258 (2012).

Khan, I., Bahuguna, A., Kumar, P., Bajpai, V. K. & Kang, S. C. Antimicrobial Potential of Carvacrol against Uropathogenic *Escherichia coli* via Membrane Disruption, Depolarization, and Reactive Oxygen Species Generation. Front. Microbiol. 8 (2017).

Konaté, K et al. Antibacterial activity against ß- lactamase producing Methicillin and Ampicillin-resistants *Staphylococcus aureus*: fractional Inhibitory Concentration Index (FICI) determination. Ann. Clin. Microbiol. Antimicrob. 11, 18 (2012).

Kumar A, Drozd M, Pina-Mimbela R, Xu X, Helmy YA, Antwi J, Fuchs JR, Nislow C, Templeton J, Blackall PJ, Rajashekara G. 2016. Novel Anti-Campylobacter Compounds Identified Using High Throughput Screening of a Pre-selected Enriched Small Molecules Library. Front Microbiol 7.

Kunze, David J., et al. "*Salmonella enterica* burden in harvest-ready cattle populations from the southern high plains of the United States." Applied and Environmental Microbiology 74.2 (2008): 345-351.

Langdon A, Crook N, Dantas G. 2016. The effects of antibiotics on the microbiome throughout development and alternative approaches for therapeutic modulation. Genome Med 8.

Leeson, P. D. & Springthorpe, B. The influence of drug-like concepts on decision-making in medicinal chemistry. Nat. Rev. Drug Discov. 6, nrd2445 (2007).

Liu C, Shi C, Mao F, Xu Y, Liu J, Wei B, Zhu J, Xiang M, Li J. 2014. Discovery of New Imidazole Derivatives Containing the 2,4-Dienone Motif with Broad-Spectrum Antifungal and Antibacterial Activity. Molecules 19:15653-15672.

Łuczak J, Jungnickel C, Łęcka I, Stolte S, Hupka J. 2010. Antimicrobial and surface activity of 1-alkyl-3-methylimidazolium derivatives. Green Chem 12:593-601.

Martens E, Demain AL. 2017. The antibiotic resistance crisis, with a focus on the United States. J Antibiot (Tokyo) 70:520-526.

Mead, Paul S., et al. "Food-related illness and death in the United States." Emerging infectious diseases 5.5 (1999): 607-25.

Mingeot-Leclercq, M .- P. & Décout, J.-L. Bacterial lipid membranes as promising targets to fight antimicrobial resistance, molecular foundations and illustration through the renewal of aminoglycoside antibiotics and emergence of amphiphilic aminoglycosides. Med Chem Comm 7, 586-611 (2016).

Mirzaei MK, Maurice CF. 2017. Menage a trois in the human gut: interactions between host, bacteria and phages. Nat Rev Microbiol 15:397-408.

(56) References Cited

OTHER PUBLICATIONS

Mobley, D. L., Bayly, C. I., Cooper, M. D., Shirts, M. R. & Dill, K. A. Small Molecule Hydration Free Energies in Explicit Solvent: An Extensive Test of Fixed-Charge Atomistic Simulations. J. Chem. Theory Comput. 5, 350-358 (2009).

Mojsoska, B., Carretero, G., Larsen, S., Mateiu, R. V. & Jenssen, H. Peptoids successfully inhibit the growth of gram negative *E. coli* causing substantial membrane damage. Sci. Rep. 7, 42332 (2017).

Mon KKZ, Saelao P, Halstead MM, Chanthavixay G, Chang H-C, Garas L, Maga EA, Zhou H. 2015. *Salmonella enterica* Serovars Enteritidis Infection Alters the Indigenous Microbiota Diversity in Young Layer Chicks. Front Vet Sci 2.

Morrison DJ, Preston T. 2016. Formation of short chain fatty acids by the gut microbiota and their impact on human metabolism. Gut Microbes 7:189-200.

Nakphaichit M, Thanomwongwattana S, Phraephaisarn C, Sakamoto N, Keawsompong S, Nakayama J, Nitisinprasert S. 2011. The effect of including Lactobacillus reuteri KUB-AC5 during post-hatch feeding on the growth and ileum microbiota of broiler chickens. Poult Sci 90:2753-2765.

Naugle, A. L., Barlow, K. E., Eblen, D. R., Teter, V. & Umholtz, R. U. S. F. Safety and Inspection Service Testing for *Salmonella* in Selected Raw Meat and Poultry Products in the United States, 1998 through 2003: Analysis of Set Results. J. Food Prot. 69, 2607-2614 (2006).

Nonejuie, P., Burkart, M., Pogliano, K. & Pogliano, J. Bacterial cytological profiling rapidly identifies the cellular pathways targeted by antibacterial molecules. Proc. Natl. Acad. Sci. 110, 16169-16174 (2013).

Oakley BB, Lillehoj HS, Kogut MH, Kim WK, Maurer JJ, Pedroso A, Lee MD, Collett SR, Johnson TJ, Cox NA. 2014. The chicken gastrointestinal microbiome. FEMS Microbiol Lett 360:100-112.

Onrust, Lonneke, et al. "Steering endogenous butyrate production in the intestinal tract of broilers as a tool to improve gut health." Frontiers in veterinary science 2 (2015): 75.

Orhan, G., Bayram, A., Zer, Y. & Balci, I. Synergy Tests by E Test and Checkerboard Methods of Antimicrobial Combinations against *Brucella melitensis*. J. Clin. Microbiol. 43, 140-143 (2005).

Painter JA, Hoekstra RM, Ayers T, Tauxe RV, Braden CR, Angulo FJ, Griffin PM. 2013. Attribution of Foodborne Illnesses, Hospitalizations, and Deaths to Food Commodities by using Outbreak Data, United States, 1998-2008. Emerg Infect Dis 19:407-415.

Pascual M, Hugas M, Badiola JI, Monfort JM, Garriga M. 1999. Lactobacillus salivarius CTC2197 Prevents *Salmonella enteritidis* Colonization in Chickens. Appl Environ Microbiol 65:4981-4986.

Pendleton JN, Gilmore BF. 2015. The antimicrobial potential of ionic liquids: A source of chemical diversity for infection and biofilm control. Int J Antimicrob Agents 46:131-139.

Pryde SE, Duncan SH, Hold GL, Stewart CS, Flint HJ. 2002. The microbiology of butyrate formation in the human colon. FEMS Microbiol Lett 217:133-139.

Rajashekara G, Glover DA, Krepps M, Splitter GA. 2005. Temporal analysis of pathogenic events in virulent and avirulent *Brucella melitensis* infections. Cell Microbiol 7:1459-1473.

Reddy GKK, Nancharaiah YV, Venugopalan VP. 2017. Long alkyl-chain imidazolium ionic liquids: Antibiofilm activity against phototrophic biofilms. Colloids Surf B Biointerfaces 155:487-496.

Rolhion N, Chassaing B. 2016. When pathogenic bacteria meet the intestinal microbiota. Phil Trans R Soc B 371:20150504.

Romantsov, T., Guan, Z. & Wood, J. M. Cardiolipin and the osmotic stress responses of bacteria. Biochim. Biophys. Acta 1788, 2092-2100 (2009).

Rychlik I, Elsheimer-Matulova M, Kyrova K. 2014. Gene expression in the chicken caecum in response to infections with non-typhoid *Salmonella*. Vet Res 45, 119.

Segata, N. et al. Metagenomic biomarker discovery and explanation. Genome Biol. 12, R60 (2011).

Sekirov I, Finlay BB. 2009. The role of the intestinal microbiota in enteric infection. J Physiol 587:4159-4167.

Selin, C et al. A Pipeline for Screening Small Molecules with Growth Inhibitory Activity against Burkholderia cenocepacia. PLOS ONE 10, e0128587 (2015).

Sepandj, F., Ceri, H., Gibb, A., Read, R. & Olson, M. Minimum inhibitory concentration (MIC) versus minimum biofilm eliminating concentration (MBEC) in evaluation of antibiotic sensitivity of gram-negative bacilli causing peritonitis. Perit. Dial. Int. J. Int. Soc. Perit. Dial. 24, 65-67 (2004).

Son, S.-H., Jeon, H.-L., Yang, S.-J., Lee, N.-K. & Paik, H.-D. In vitro haracterization of Lactobacillus brevis KU15006, an isolate from kimchi, reveals anti-adhesion activity against foodborne pathogens and antidiabetic properties. Microb. Pathog. 112, 135-141 (2017).

Sonnenburg JL, Bäckhed F. 2016. Diet-microbiota interactions as moderators of human metabolism. Nature 535:56-64.

Sridhar, S. & Steele-Mortimer, O. Inherent Variability of Growth Media Impacts the Ability of *Salmonella* Typhimurium to Interact with Host Cells. PLoS ONE 11 (2016).

Su, L.-H., Chiu, C.-H., Chu, C. & Ou, J. T. Antimicrobial Resistance in Nontyphoid *Salmonella* Serotypes: A Global Challenge. Clin. Infect. Dis. 39, 546-551 (2004).

Sun Y, O'Riordan MXD. 2013. Regulation of bacterial pathogenesis by intestinal short-chain Fatty acids. Adv Appl Microbiol 85:93-118.

Svetoch EA, Eruslanov BV, Levchuk VP, Perelygin VV, Mitsevich EV, Mitsevich IP, Stepanshin J, Dyatlov I, Seal BS, Stern NJ. 2011. Isolation of Lactobacillus salivarius 1077 (NRRL B-50053) and Characterization of Its Bacteriocin, Including the Antimicrobial Activity Spectrum V . Appl Environ Microbiol 77:2749-2754.

Trincherini, Pier Renato, et al. "Precise determination of strontium isotope ratios by TIMS to authenticate tomato geographical origin." Food chemistry 145 (2014):349-355.

Tsai CJ-Y, Loh JMS, Proft T. 2016. Galleria mellonella infection models for the study of bacterial diseases and for antimicrobial drug testing. Virulence 7:214-229.

Urfer, M. et al. A Peptidomimetic Antibiotic Targets Outer Membrane Proteins and Disrupts Selectively the Outer Membrane in *Escherichia coli*. J. Biol. Chem. 291, 1921-1932 (2016).

Van der Wielen PWJJ, Bolhuis H, Borin S, Daffonchio D, Corselli C, Giuliano L, D'Auria G, de Lange GJ, Huebner A, Varnavas SP, Thomson J, Tamburini C, Marty D, McGenity TJ, Timmis KN, BioDeep Scientific Party. 2005. The enigma of prokaryotic life in deep hypersaline anoxic basins. Science 307:121-123.

Veber, D. F. et al. Molecular Properties That Influence the Oral Bioavailability of Drug Candidates. J. Med. Chem. 45, 2615-2623 (2002).

Vrisman CM, Deblais L, Rajashekara G, Miller SA. 2016. Differential Colonization Dynamics of Cucurbit Hosts by Erwinia tracheiphila. Phytopathology 106:684-692.

Vukomanović, M. et al. Nano-engineering the Antimicrobial Spectrum of Lantibiotics: Activity of Nisin against Gram Negative Bacteria. Sci. Rep. 7, 4324 (2017).

Wallace, I. M. et al. Compound prioritization methods increase rates of chemical probe discovery in model organisms. Chem. Biol. 18, 1273-1283 (2011).

Wells, J. G., et al. "Laboratory investigation of hemorrhagic colitis outbreaks associated with a rare *Escherichia coli* serotype." Journal of clinical microbiology 18.3 (1983): 512-520.

Wielen PWJJ van der, Biesterveld S, Notermans S, Hofstra H, Urlings BAP, Knapen F van. 2000. Role of Volatile Fatty Acids in Development of the Cecal Microflora in Broiler Chickens during Growth. Appl Environ Microbiol 66:2536-2540.

Xu X, Kumar A, Deblais L, Pina-Mimbela R, Nislow C, Fuchs JR, Miller SA, Rajashekara G. 2015. Discovery of novel small molecule modulators of Clavibacter michiganensis subsp. michiganensis. Front Microbiol 6, 1127.

Xu, Y. et al. Bacterial Diversity of Intestinal Microbiota in Patients with Substance Use Disorders Revealed by 16S rRNA Gene Deep Sequencing. Sci. Rep. 2017, 7, 3628.

Zhang, Y., Liu, X., Wang, Y., Jiang, P. & Quek, S. Antibacterial activity and mechanism of cinnamon essential oil against *Escherichia coli* and *Staphylococcus aureus*. Food Control 59, 282-289 (2016).

(56) References Cited

OTHER PUBLICATIONS

L. Deblais, Y.A. Helmy, D. Kathayat, C. Vrisman, R. Candelero, H.C Huang, S.A. Miller, and G. Rajashekara "A combined genomic and in vivo imaging platform to understanding *Salmonella*-tomato plant host interactions" NIFRA IAFP meeting (Tampa—USA—Jul. 2017).

L. Deblais, Y.A. Helmy, R. Candelero-Rueda, D. Kathayat, H. Huang, S.A. Miller, and G. Rajashekara "Reduction of *Salmonella* burden in poultry using new generation small molecules" OBASM (Columbus—USA—Apr. 2017).

L. Deblais, Y.A. Helmy, R. Candelero-Rueda, D. Kathayat, H. Huang, S.A. Miller, and G. Rajashekara "Novel anti-Salmonella compounds reduce *Salmonella* burden in poultry" ASM Antimicrobial Development meeting (Washington—USA—Dec. 2016).

L. Deblais, R. Candelero, Y.A. Helmy, C. Vrisman, S.A. Miller, and G. Rajashekara "A combined genomic and in vivo imaging platform to understanding Salmonella-tomato plant host interactions" NIFRA IAFP meeting (Missouri—USA—Jul. 2016).

L. Deblais, Y.A. Helmy, R. Candelero, Huang-chi Huang, Dipak Kathayat, S.A. Miller, and G. Rajashekara "Small molecules, a potential novel control strategy to reduce *Salmonella* burden" I3S meeting (Saint-malo—France—Jul. 2016).

L. Deblais, S. Miller, F.B. Gurel, and G. Rajashekara "Understanding *Salmonella*- tomato plant host interactions and development of effective novel control strategies to reduce *Salmonella* burden in tomato production" IAFP meeting (Oregon—USA—Jul. 2015).

Karjalainen, Katja, et al. "Design, development, and validation of a high-throughput drug-screening assay for targeting of human leukemia." Cancer 120.4 (2014): 589-602.

Deblais, Loïc, et al. "Novel imidazole and methoxybenzylamine growth inhibitors affecting *Salmonella* cell envelope integrity and its persistence in chickens." Scientific reports 8.1 (2018): 1-17.

Deblais, Loïc, et al. "Imidazole and methoxybenzylamine growth inhibitors reduce *Salmonella* persistence in tomato plant tissues." Journal of food protection 82.6 (2019): 997-1006.

De Waelheyns, Evelien, et al. "Identification of small-molecule inhibitors against SecA by structure-based virtual ligand screening." The Journal of antibiotics 68.11 (2015): 666-673.

International Preliminary Report on Patentability issued for Application No. PCT/US2018/066767, dated Jul. 2, 2020.

\* cited by examiner

SM1: 2834410

| ASSIGNED OTUs | N | 0 | 1 | 3 | 4 | 5 |
|---|---|---|---|---|---|---|
| Actinobacteria, Coriobacteriia, Coriobacteriales, Coriobacteriaceae | B | | | | | |
| Firmicutes, Bacilli, Bacillales, Bacillaceae | B | | | | | |
| Firmicutes, Bacilli, Bacillales, Bacillaceae, Bacillus | B | | | B | | |
| Firmicutes, Bacilli, Bacillales, Paenibacillaceae, Paenibacillus macerans | | | | | | |
| Firmicutes, Bacilli, Bacillales, Planococcaceae | | | | | | |
| Firmicutes, Bacilli, Bacillales, Planococcaceae, Planomicrobium | | | | | | |
| Firmicutes, Bacilli, Lactobacillales, Enterococcaceae, Enterococcus | | | | | | |
| Firmicutes, Bacilli, Lactobacillales, Enterococcaceae, Enterococcus casseliflavus | | | | | | |
| Firmicutes, Bacilli, Lactobacillales, Lactobacillaceae | B | | | | | |
| Firmicutes, Bacilli, Lactobacillales, Lactobacillaceae, Lactobacillus | B | | B | | | |
| Firmicutes, Bacilli, Lactobacillales, Lactobacillaceae, Lactobacillus reuteri | | | | | | |
| Firmicutes, Bacilli, Lactobacillales, Lactobacillaceae, Pediococcus | | | | | | |
| Firmicutes, Bacilli, Lactobacillales, Lactobacillaceae, Pediococcus acidilactici | | | | | | |
| Firmicutes, Bacilli, Lactobacillales, Leuconostocaceae | | | | A | | |
| Firmicutes, Bacilli, Lactobacillales, Leuconostocaceae, Weissella | | | | | | |
| Firmicutes, Clostridia, Clostridiales, Clostridiaceae | A | | | | | |
| Firmicutes, Clostridia, Clostridiales, Clostridiaceae, Clostridium | A | | | A | | |
| Firmicutes, Clostridia, Clostridiales, Clostridiaceae, Clostridium neonatale | | | | | | |
| Firmicutes, Clostridia, Clostridiales, Lachnospiraceae | | | | | | |
| Firmicutes, Clostridia, Clostridiales, Lachnospiraceae, [Ruminococcus] | | | | | | |
| Firmicutes, Clostridia, Clostridiales, Lachnospiraceae, [Ruminococcus] gnavus | | | | | | |
| Firmicutes, Clostridia, Clostridiales, Lachnospiraceae, [Ruminococcus] torques | | | | | | |
| Firmicutes, Clostridia, Clostridiales, Lachnospiraceae, Blautia | | | | | | |
| Firmicutes, Clostridia, Clostridiales, Lachnospiraceae, Blautia obeum | | | | | | |
| Firmicutes, Clostridia, Clostridiales, Lachnospiraceae, Blautia producta | | | | | | |
| Firmicutes, Clostridia, Clostridiales, Lachnospiraceae, Coprococcus | | | | | | |
| Firmicutes, Clostridia, Clostridiales, Lachnospiraceae, Dorea | | | | | | |
| Firmicutes, Clostridia, Clostridiales, Lachnospiraceae, Lachnospira | | | | | | |
| Firmicutes, Clostridia, Clostridiales, Ruminococcaceae | B | | B | | B | |
| Firmicutes, Clostridia, Clostridiales, Ruminococcaceae, Anaerotruncus | B | | B | | | |
| Firmicutes, Clostridia, Clostridiales, Ruminococcaceae, Butyricicoccus pullicaecorum | B | | | | A | |
| Firmicutes, Clostridia, Clostridiales, Ruminococcaceae, Oscillospira | | | B | | | |
| Firmicutes, Clostridia, Clostridiales, Ruminococcaceae, Ruminococcus | B | | | | | |
| Firmicutes, Erysipelotrichi, Erysipelotrichales, Erysipelotrichaceae | | | | | | |
| Firmicutes, Erysipelotrichi, Erysipelotrichales, Erysipelotrichaceae, [Eubacterium] dolichum | | | | | | |
| Firmicutes, Erysipelotrichi, Erysipelotrichales, Erysipelotrichaceae, Allobaculum | | | | | | |
| Firmicutes, Erysipelotrichi, Erysipelotrichales, Erysipelotrichaceae, Clostridium | | | | | | |
| Firmicutes, Erysipelotrichi, Erysipelotrichales, Erysipelotrichaceae, Coprobacillus | | | | | | |
| Proteobacteria, Betaproteobacteria | | | | | | |

FIG. 6B

| | | | | | |
|---|---|---|---|---|---|
| Proteobacteria, Gammaproteobacteria, Enterobacteriales, Enterobacteriaceae | | | A | | |
| Proteobacteria, Gammaproteobacteria, Enterobacteriales, Enterobacteriaceae, Escherichia, coli | | | | | |
| Proteobacteria, Gammaproteobacteria, Enterobacteriales, Enterobacteriaceae, Salmonella | B | B | | B | B |
| Proteobacteria, Gammaproteobacteria, Oceanospirillales, Halomonadaceae, Halomonas | | | | | |
| Tenericutes, Mollicutes, RF39 | | | | | |
| Unassigned | | | | | |

FIG. 6B (con't)

| Strains | SM1 | SM3 | SM4 | SM5 | Antagonistic to Salmonella |
|---|---|---|---|---|---|
| Acidovorax citrulli | | ■ | | ■ | ND |
| Agrobacterium rhizogenes strain K599 | | | | | ND |
| Clavibacter michiganensis michiganensis | | ■ | ■ | | ND |
| Erwinia amylovora strain MLJ90-15 | | | | | ND |
| Erwinia tracheiphila | | | | | ND |
| Pseudomonas syringae pv. lachrymans strain SM317-11 | | | | | ND |
| Serratia marcescens strain SM1794 | | | | ■ | ND |
| Xanthomonas cucurbitae strain SM622-11 | | | | | ND |
| Xanthomonas gardneri | | | | | ND |
| Xanthomonas perforans | | ■ | ■ | | ND |
| Bacillus subtilis strain BS1 | | | | | Yes |
| Bacillus subtilis strain G803 | | | | ■ | Yes |
| Bacillus amyloliquefaciens strain BA1 | ■ | | | | Yes |
| Enterobacter sp. strain 8CA | ■ | | ■ | | Yes |
| Lysobacter enzymogenes C3 | | | | | No |
| Mitsuaria strain H24L5A | | | | | No |
| Pseudomonas fluorescens strain SAM98-08 | | | | | No |
| Pseudomonas chlororaphis strain 14B11 | | | | | No |
| Pseudomonas chlororaphis strain 48B8 | | | | | No |
| Pseudomonas chlororaphis strain 48G9 | | | | | No |
| Pseudomonas protegens strain 12H11 | | | | | No |
| Streptomyces sp. strain S2 | | | | | No |

FIG. 14

METHODS TO CONTROL INFECTION USING NEW GENERATION SMALL MOLECULE GROWTH INHIBITORS

CROSS REFERENCE TO RELATED APPLICATIONS

This application is a continuation of U.S. patent application Ser. No. 16/955,603, filed Jun. 18, 2020, which is a national stage application filed under 35 U.S.C. § 371 of PCT/US2018/066767 filed Dec. 20, 2018, which claims the benefit of U.S. Provisional Patent Application Ser. No. 62/608,335 filed Dec. 20, 2017, which are is expressly incorporated herein by reference.

STATEMENT REGARDING FEDERALLY SPONSORED RESEARCH

This invention was made with government support under Grant No. 2013-67018-21240 awarded by the National Institute of Food & Agriculture, United States Department of Agriculture. The government has certain rights in the invention.

FIELD

The present invention relates to methods to control microbial growth, particularly bacterial growth, in animals and plants. The invention further relates to providing to animals and/or plants compositions containing certain small molecules which have excellent antimicrobial properties, low toxicity to host cells and normal flora, and additive or synergistic effects with other antibiotics.

BACKGROUND

Foodborne illnesses can result in major public health implications in the U.S. and around the world. According to recently published Centers for Disease Control and Prevention data, foodborne diseases account for approximately 8 million illnesses, and 9,000 deaths each year in the U.S. alone. The epidemiology of foodborne diseases is rapidly changing as newly recognized pathogens emerge and well-studied pathogens increase in prevalence or associate with new food vehicles. Apart from acute gastroenteritis, some foodborne diseases may cause chronic illness or disability. Listeriosis, for instance, can cause miscarriages or meningitis in patients with pre-existing chronic diseases. As meat and meat products are the major source of foodborne infection and the most important link between food-producing animals and humans, the study of foodborne pathogens isolated from meat and poultry is indispensable. In addition, plants and plant products are also important sources of microbial contaminations, such as *Salmonella Typhimurium*.

Microbial contamination can reduce the shelf life of foods and increase the risk of foodborne illness, and is a major worldwide public health concern. According to statistical data from the Center for Disease Control (CDC), five pathogen types account for over 90% of the estimated food-related deaths: *Salmonella, Listeria, Campylobacter, E. coli* 0157:H7, and *Vibrio*.

Non-typhoid *Salmonella* (NTS) are one of the most common causes of human food poisoning worldwide. *Salmonellosis* cases are prevalent following a physical contact with a contaminated host or the consumption of contaminated foods such as poultry products, which are the most common vector of *Salmonella* infections in humans (Painter et al., *Emerg Infect Dis*, 2013, 19:407-415; Rychlik at al., *Vet Res.*, 2014, 45; Antunes et al., *Clin Microbiol Infect*, 2016, 22:110-121). *Salmonella* can colonize at high density the gastrointestinal track (GI) of chickens within a few days after infection and without clinical signs of the pathogen (Antunes et al., *Clin Microbiol Infect*, 2016, 22:110-121). In some cases, a prolonged infection can lead to bacteremia followed by the contamination of other organs such as spleen, liver, and ovaries (Antunes et al., *Clin Microbiol Infect*, 2016, 22:110-121). Infected chickens can rapidly disseminate *Salmonella* through the whole population via persistent shedding of the pathogen in the contaminated feces or vertical transfer to the next generation via eggs (Foley et al., *Appl Environ Microbiol* 2011, 77:4273-4279). An early infection can result in the broad contamination of a farm environment and a high morbidity level (Foley et al., *Appl Environ Microbiol* 2011, 77:4273-4279; Mon et al., *Front Vet Sci*, 2015, 2).

Despite detailed knowledge about *Salmonella* infection in chickens, the *salmonellosis* incidence rate in humans has remained the same over the past fifteen years (www.food-protection.org/files/food-protection-trends/NovDec-14-McEntire.pdf). Since 1990, 53 poultry-associated *salmonellosis* outbreaks were reported in the U.S., causing 2,630 illnesses, about 387 hospitalizations, and 5 deaths (Basler et al., *Emerg Infect Dis*, 2016, 22:1705-1711). It was estimated that *Salmonella* associated with poultry cost up to $695 million in public health (Batz et al., *J Food Prot*, 2012, 75:1278-1291). A recent study showed that 97% of the tested chicken breasts harbored potential microbes coming from the host intestines that could cause food poisoning in human, and about 11%-19% of the carcasses were contaminated with *Salmonella*. Pre-harvest control methods (competitive exclusion, vaccination, drug therapy) are available to reduce post-harvest contaminations of the carcasses; however, their effects are limited or easily overcome by *Salmonella* due to a constant adaptation of *Salmonella* to antimicrobial management strategies (Foley et al., *Appl Environ Microbiol* 2011, 77:4273-4279). For example, 100,000 *Salmonellosis* cases are caused by multi-drug resistant *Salmonella* strains in the U.S. annually. Further, the genus *Salmonella* currently includes more than 2,400 different serotypes, complicating targeted treatment regimens. At present, *Salmonella* are resistant to two important groups of drugs (cephalosporins and fluoroquinolones). This is a primary reason why the development of novel, narrow spectrum antimicrobial treatment effective against *Salmonella* is necessary to counter *Salmonella* burden and improve public safety (Martens et al., *J Antibiot (Tokyo)*, 2017, 70:520-526).

*Campylobacter* bacteria are thin, curved, motile gram-negative rods. They are generally micro-aerophilic, though some strains are aerobic and anaerobic. Currently, *Campylobacter* species are recognized as the leading cause of foodborne gastroenteritis in the U.S. and one of the most frequent causes of acute bacterial enteritis worldwide (Mead et al., *Emerg. Infect. Dis.*, 1999, 5607-5625). Gastroenteritis caused by *Campylobacter* is an acute diarrheal disease that typically causes high fever, abdominal cramping, and diarrhea that last from several days to more than one week. *C. jejuni* and *C. coli* (clinically indistinguishable) are the most common species associated with diarrheal illness, causing more than 95% of *Campylobacter* enteritis (Harris et al., *Am J. Public Health*, 1986, 76:407-11). Reports of campylobacteriosis cases are continuously increasing in many parts of the world.

Shiga-toxin-producing *Escherichia coli* (STEC) was first recognized as an emerging human pathogen in 1982 when *E.*

*coli* 0157:H7 was implicated in two outbreaks of hemorrhagic colitis associated with consumption of uncooked beef (Wells et al., *J. Clin. Microbiol.,* 1983, 185:12-20). Human infection with STEC can lead to non-bloody diarrhea or bloody diarrhea, or more serious and fatal syndrome such as hemorrhagic colitis and hemolytic uremic syndrome. *E. coli* 0157:H7 causes approximately 73,000 illnesses and 60 deaths each year in the US. Antimicrobial therapy is one of the most effective ways to prevent and control bacterial diseases. Currently, the most commonly used antimicrobials are macrolides (erythromycin) and fluoroquinolones (ciprofloxacin) with tetracycline used as an alternative. However, as the use of antimicrobials for therapy and prophylaxis increase in both human and animal medicine, increasing numbers of bacteria have developed resistance to these antimicrobials.

As *Salmonella, Listeria, Campylobacter, E. coli*, and *Vibrio* are projected to remain top foodborne pathogens globally for the foreseeable future, and because several antibiotics are no longer effective treatments against them, a new generation of effective antimicrobials is critically needed. The compounds, compositions, and methods disclosed herein address these and other needs.

SUMMARY

Disclosed herein are methods of controlling bacterial growth or infections in animals and/or plants using certain small molecules which have excellent antimicrobial properties, low toxicity to host cells and normal flora, and additive or synergistic effects with other antibiotics.

Current antimicrobial treatments have become old and obsolete, and their effects are limited or easily overcome by foodborne pathogens such as *Salmonella*. Disclosed herein are methods for controlling an array of pathogenic microbes at low concentration. The methods include administering any one or more of four small molecules (SMs) identified as having excellent microbicidal properties. The methods are capable of controlling infection and growth of several *Salmonella* serotypes, including the human pathogen *S. typhimurium*, and numerous other bacterial zoonotic pathogens and/or phytopathogens. Further, the SMs administered in the methods have synergetic or additive antimicrobial effects with ciprofloxacin, cefepime, and meropenem against *Salmonella*, similar antimicrobial activity against biofilm-protected *Salmonella*, limited antimicrobial activity against beneficial bacteria (e.g., gut normal flora or plant-commensal bacteria), and little to no toxicity to many eukaryotic models. The methods increase survival of *Salmonella*-infected hosts, decrease infecting bacterial populations (e.g., *S. typhimurium* populations in cecal and systemic tissues), and have minimal impact on overall commensal microbiota (e.g., native cecal microbiota).

Disclosed herein are methods of treating a subject with a bacterial infection comprising administering to the subject an effective amount of at least one compound, or a derivative thereof, having the following formula:

SM1

SM3

SM4 or

SM5

Also disclosed are methods of preventing a bacterial infection in a subject comprising administering to the subject an effective amount of at least one compound, or a derivative thereof, having the following formula:

SM1
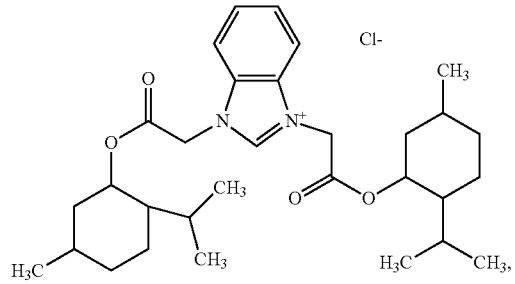

SM3
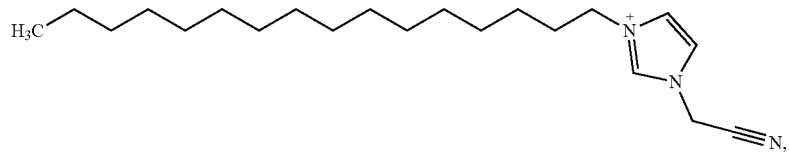

SM4
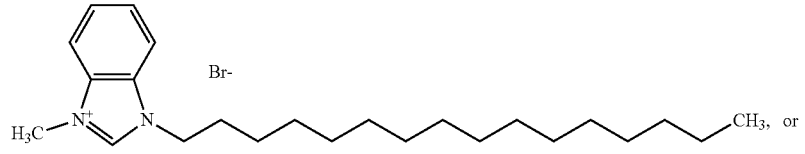

or

SM5
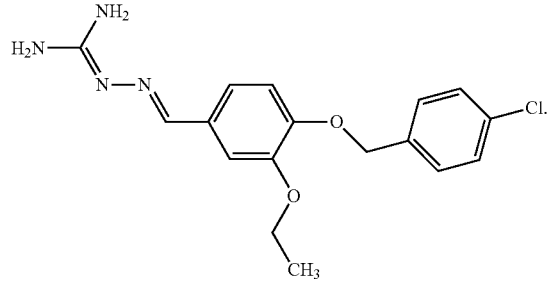

Also described are methods of inhibiting bacterial growth in a plant comprising contacting the plant with an effective amount of at least one compound, or a derivative thereof, having the following formula:

SM1
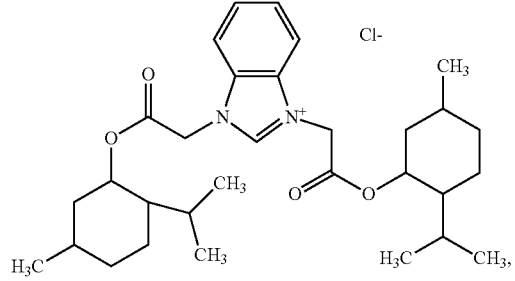

SM3
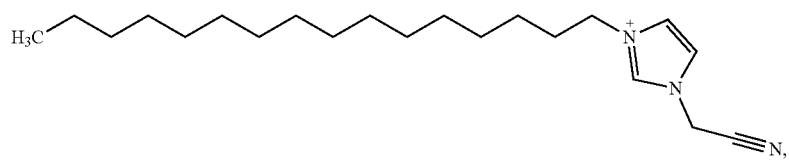

-continued

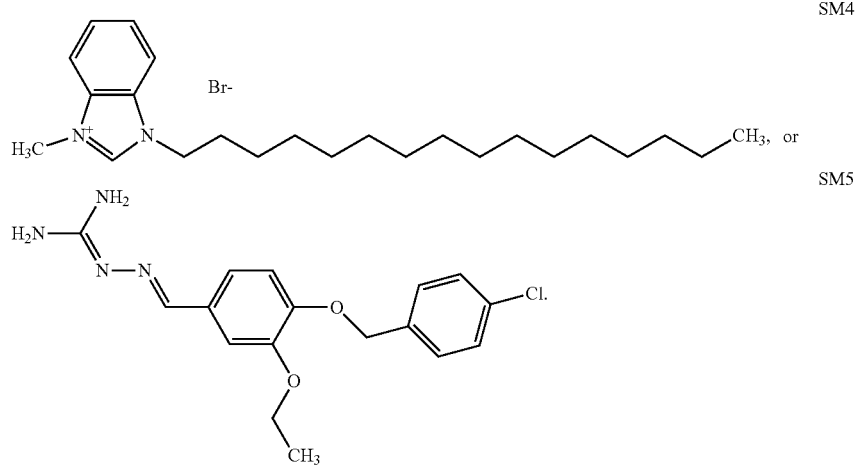

BRIEF DESCRIPTION OF THE DRAWINGS

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are explanatory only and are not restrictive of the disclosure.

The accompanying drawings, which are incorporated in and constitute a part of this specification, illustrate certain examples of the present disclosure and together with the description, serve to explain, without limitation, the principles of the disclosure.

FIGS. 1(A-E). Selection of potent *Salmonella* growth inhibitors.

FIGS. 2(A-E). Structural analysis of the selected 19 *S. typhimurium* inhibitors.

FIGS. 3(A-B). Toxicity of the selected four SMs on several eukaryotic models.

FIGS. 4(A-B). Preventive antimicrobial efficacy of SM treatment in *S. typhimurium*-infected *G. mellonella*. Larva were first treated with 12.5 μg SMs per larva (50 mg/kg), incubated for 2 hrs at 37° C. in the dark, then infected with $10^4$ CFU per larva, and further incubated at 37° C. in the dark for 72 hrs.

FIGS. 5(A-C). In vivo effects of SM administration in chickens.

FIGS. 6(A-B). Effect of SM treatments on microbiota relative abundance in chicken ceca. FIG. 6B: Microbiota diversity and relative abundance per treatment. Gray boxes: OTUs detected in chicken ceca; white boxes: OTUs not detected in chicken ceca. A and B indicate whether the OTUs were significantly lower or higher in abundance compared to the DMSO group, respectively (P<0.01); N: not infected, not treated chickens; D: DMSO treated chickens; 1-5: chickens treated with SM1, SM3, SM4, or SM5.

FIGS. 8(A-C). Stable chromosomal insertion of pUWGR4 plasmid into *S. typhimurium* LT2 did not affect growth rate.

FIGS. 9(A-C). Impact of SM treatment on microbiota alpha and beta diversities in chicken ceca. No differences in alpha diversity between SM-treated chickens and DMSO-treated chickens were detected (P>0.05); however, a distinct spatial separation was observed between the non-*Salmonella* challenged group and the *Salmonella* challenged groups using unweighted uniFrac values.

FIGS. 10(A-D). SM toxicity on tomato tissues at 200 μM.

FIG. 14. SM activity (200 μM) on plant-associated bacteria. Bacteria names in bold are plant pathogens. Bacteria names in unbolded font are beneficial bacteria for plants. White cells: bactericidal; gray cells: bacteriostatic; black cells: bacterial growth; ND: not determined.

DETAILED DESCRIPTION

Figure 1A:
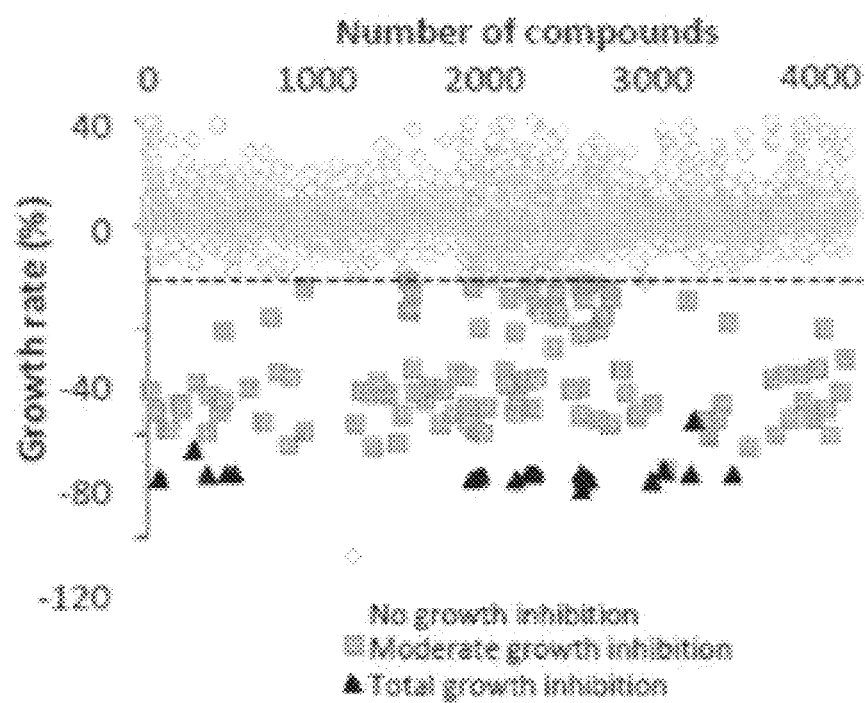
FIG. 1A: High-throughput screening of 4182 SMs against *S. typhimurium* WT at 200 μM. Negative value: growth inhibition; Positive value: growth stimulation compared to *S. typhimurium* growth not treated. The black line represents growth inhibition caused by 2% DMSO.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

The following definitions are provided for the full understanding of terms used in this specification. Unless defined otherwise, all technical and scientific terms used herein have the same meaning as commonly understood to one of ordinary skill in the art to which this disclosure belongs.

The term "comprising" and variations thereof as used herein is used synonymously with the terms "including," "containing," and variations thereof and are open, non-limiting terms. Although the terms "comprising," "including," and "containing" have been used herein to describe various embodiments, the terms "consisting essentially of" and "consisting of" can be used in place of "comprising," "including," and "containing" to provide for more specific embodiments and are also disclosed.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to the compound are discussed, specifically contemplated is each and every combination and permutation of the compound and the modifications that are possible unless specifically indicated to the contrary. Thus, if a class of compounds A, B, and C are disclosed as well as a class of compounds D, E, and F and an example of a combination compound, or, for example, a combination compound comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In some non-limiting embodiments, the terms are defined to be within 10% of the associated value provided. In some non-limiting embodiments, the terms are defined to be within 5%. In still other non-limiting embodiments, the terms are defined to be within 1%.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

For oral administration, oral compositions such as tablets and capsules may be in unit dose form, and may contain excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl phydroxybenzoate or sorbic acid, and if desired conventional flavoring or coloring agents. In some embodiments, the oral compositions can be mixed with feed product given to a subject (e.g., feedstock for poultry).

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both "therapeutically effective amounts" and "prophylactically effective amounts". An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

Derivatives of the herein disclosed compounds include salts. Pharmaceutically acceptable salts include "Pharmaceutically acceptable salts" includes derivatives of the disclosed compounds wherein the parent compound is modified by making an acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like. The pharmaceutically acceptable salts of can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable.

"Preventing" a disorder or unwanted physiological event in a subject refers specifically to the prevention of the occurrence of symptoms and/or their underlying cause, wherein the subject may or may not exhibit heightened susceptibility to the disorder or event. As used herein, preventing infection includes preventing or delaying the initiation of infection. The term further includes preventing a recurrence of one or more signs or symptoms of infection.

"Treat," "treating," "treatment," and grammatical variations thereof as used herein, include the administration of a composition with the intent or purpose of partially or completely delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Compositions and Methods for Animal Subjects

It is understood that the methods of the present disclosure can be used in combination with the various compositions, methods, products, kits, and applications disclosed herein.

Disclosed herein are methods of treating a subject with a bacterial infection. The methods comprise administering to the subject an effective amount of at least one compound, or a derivative thereof. The compound has the following formula:

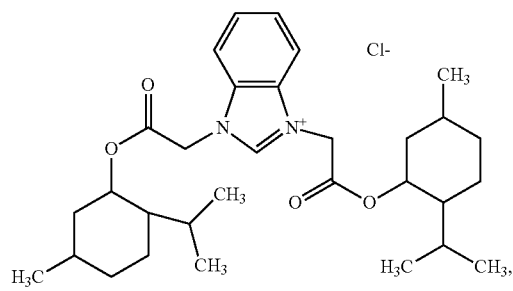
SM1

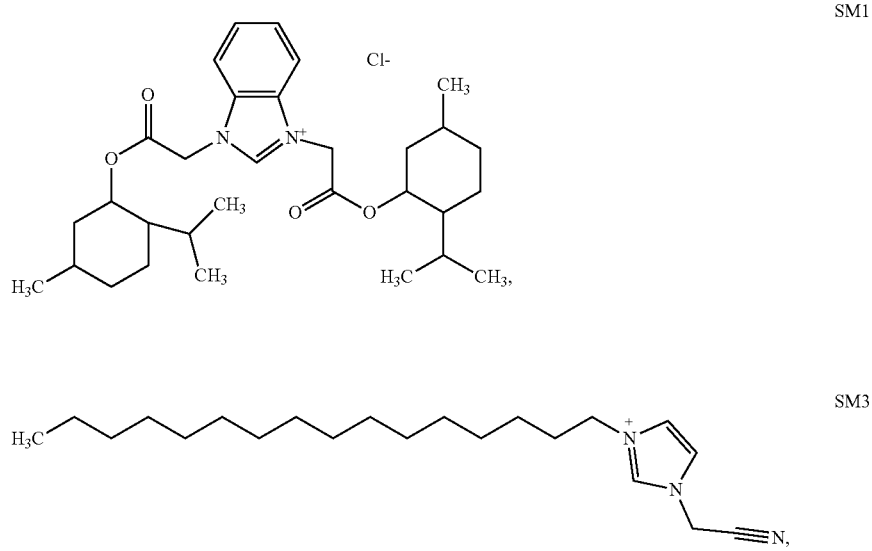
SM3

SM4

SM5

Administration of the at Least One Compound Thereby Treats the Infection.

Also disclosed herein are methods of preventing a bacterial infection in a subject comprising administering to the subject an effective amount of at least one compound, or a derivative thereof, having the following formula:

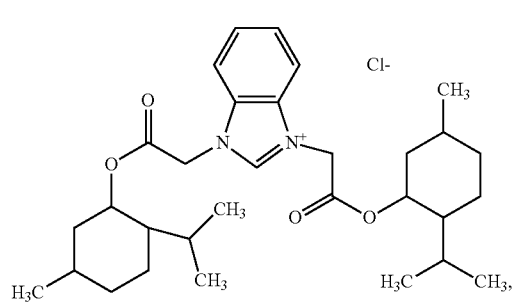
SM1

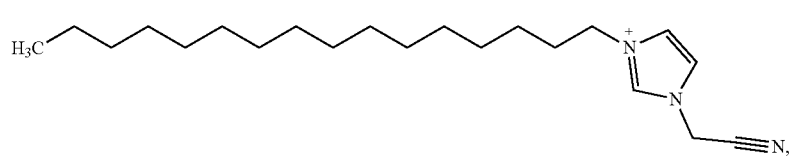
SM3

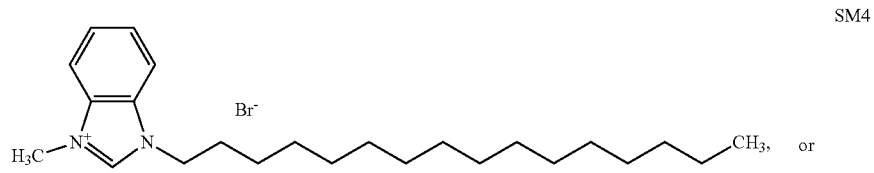
SM4

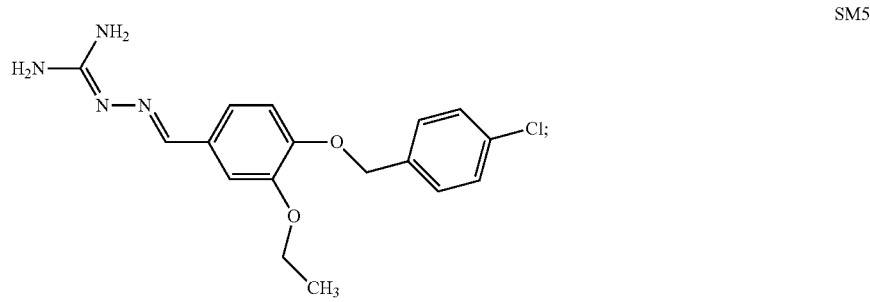
SM5

In some embodiments of the herein disclosed methods, the infection comprises *Salmonella, Campylobacter jejuni, Escherichia coli*, or *Mycoplasma gallisepticum*. In some embodiments, the infection comprises bacteria arranged in a biofilm. In some embodiments, the subject comprises a mammalian or avian subject, or in some particular embodiments, a human or a poultry subject. In some embodiments, the methods comprise administering 200 µg or less of the compound to the subject. In some embodiments, the methods further comprise administering an antibiotic (e.g., ciprofloxacin, cefepime, or Meropenem). In some embodiments, the compound and the antibiotic have a synergistic bactericidal effect. In some embodiments, the compound does not inhibit growth of at least one cecal microbiota organism (e.g., *Clostridium clostridioforme, Bacteroides thetaiotaomicron, Bifidobacterium adolescentis, Bifidobacterium longum, Enterococcus faecalis, Lactobacillus brevis*, or *Lactobacillus rhamnosus*). In some embodiments, the compound promotes growth of a cecal microbiota organism (e.g., Leuconostocaceae, *Lactobacillus*, or *Butyricicoccus pullicaecorum* species).

The disclosure is based in part on the identification of certain high-throughput screened small molecules which have excellent antimicrobial properties, low toxicity to commensal cecal microbiota and eukaryotic cells, and can have additive or synergetic activities with certain known antibiotics. The identified small molecules (SMs) are thus compounds which can be administered to treat and/or prevent a bacterial infection.

In some embodiments, the at least one compound can comprise 1,3-bis {2-[(2-isopropyl-5-methylcyclohexyl)oxy]-2-oxoethyl}-1H-3,1-benzimidazol-3-ium chloride (SM1); 1-(cyanomethyl)-3-hexadecyl-1H-imidazol-3-ium chloride (SM3); 1-hexadecyl-3-methyl-1H-3,1-benzimidazol-3-ium bromide (SM4); N''-{4-[(4-chlorobenzyl)oxy]-3-ethoxybenzylidene}carbonohydrazonic diamide (SM5), or a derivative of any of the foregoing. In some embodiments, the compound comprises 1-(3,6-dibromo-9H-carbazol-9-yl)-3-[(2-hydroxyethyl)(methyl)amino]-2-propanol (SM2) or a derivative thereof. In some embodiments, the compound comprises 1-[benzyl(methyl)amino]-3-[4-({[(5-chloro-2-thienyl)methyl]amino}methyl)phenoxy]-2-propanol (SM6), 2,4-dichloro-6-{[(2-fluoro-5-nitrophenyl)imino]methyl}phenol (SM7), 2,4-dichloro-6-{[(3-methoxyphenyl)imino]methyl}phenol (SM8), N-[1-(4-isobutylbenzyl)-3-piperidinyl]-2-(4-methyl-1,4-diazepan-1-yl)acetamide (SM9), ethyl 5-acetyl-2-amino-4-methyl-3-thiophenecarboxylate (SM10), 4-[1-(3-methoxyphenyl)cyclopentyl]phenol (SM11), 3-[3-(4-bromophenyl)-2-triazen-1-yl]-5-nitrobenzoic acid (SM12), 1-benzyl-N-[2-(2,4-dichlorophenyl)ethyl]-4-piperidinamine (SM13), 1-(1-azocanyl)-3-(2-methoxy-5-{[(4-methylbenzyl)amino]methyl}phenoxy)-2-propanol (SM15), 4-bromo-2-{[(3-methoxyphenyl)imino]methyl}phenol (SM16), 1-methyl-5-[(5-nitro-2-furyl)methylene]-2,4,6(1H,3H,5H)-pyrimidinetrione (SM17), 4-benzoyl-5-methyl-2-phenyl-2,4-dihydro-3H-pyrazol-3-one (SM18), 1-(9H-fluoren-9-yl)-4-(3-phenyl-2-propen-1-yl)piperazine (SM19), or a derivative of any of the foregoing. Derivatives of a compound include, but are not limited to, any salt, ester, acids, bases, solvates, hydrates, prodrugs, etc. Derivatives, modifications and pharmaceutically acceptable salts retain the functional properties described herein.

Also disclosed herein are compositions comprising an effective amount of at least one compound, or a derivative thereof, having the following formula:

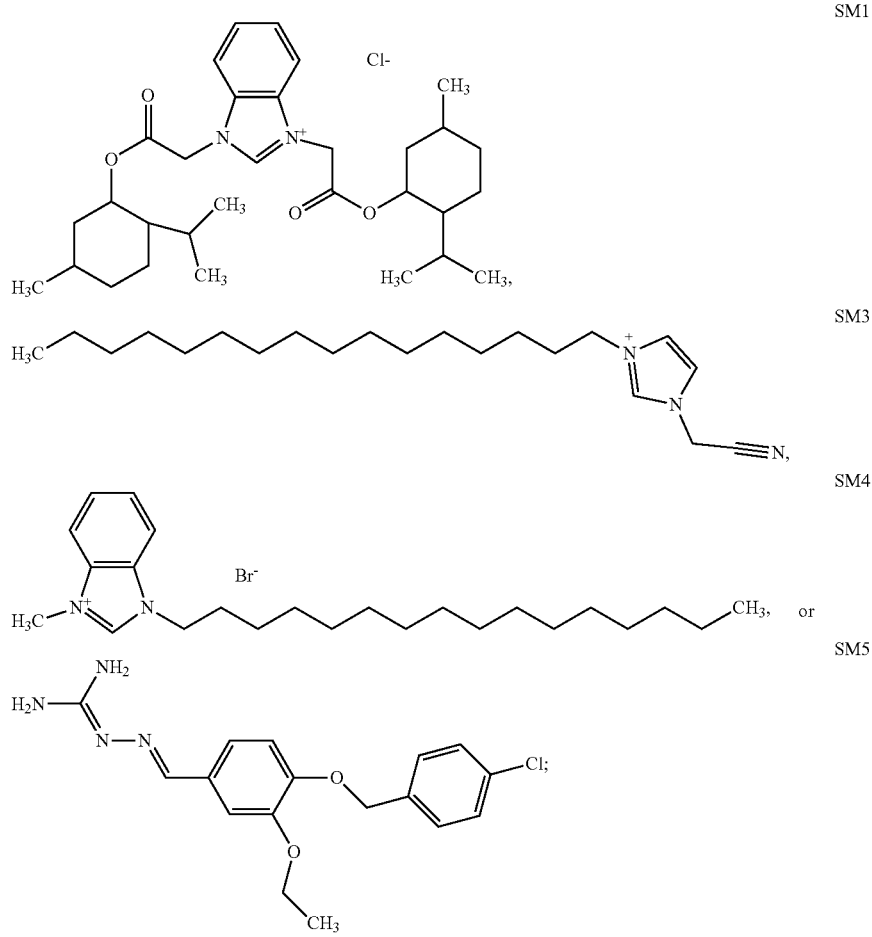
and
an additional antibiotic;
wherein the compound and the additional antibiotic exhibit synergism.
In some embodiments, the composition comprises an effective amount of at least one compound, or a derivative thereof, having the following formula:
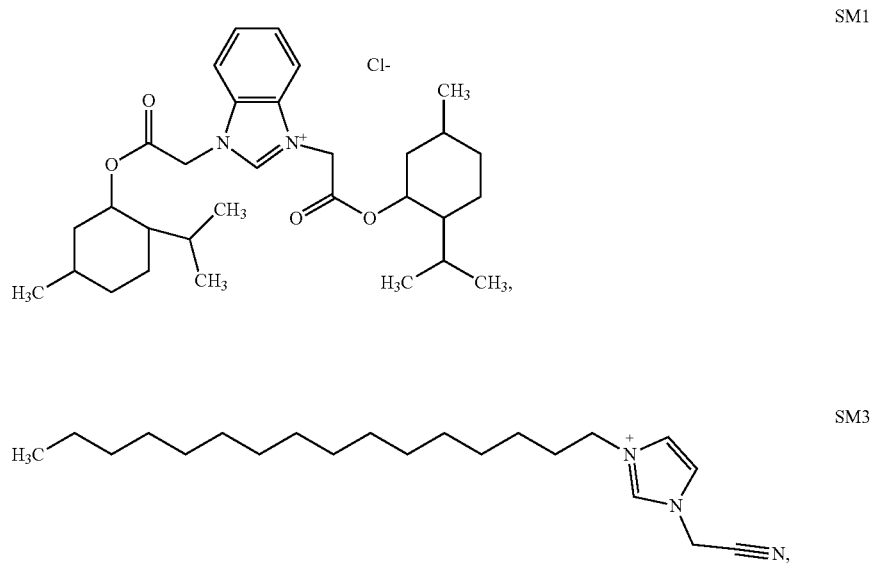

-continued

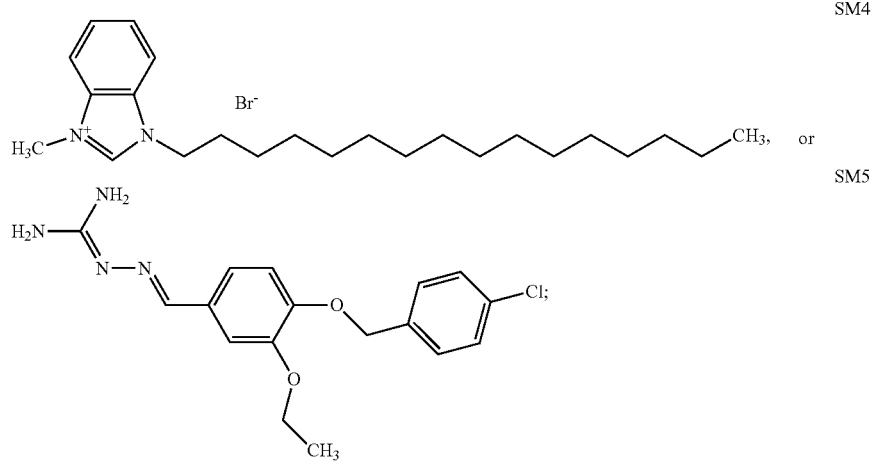

SM4 or

SM5 and
an additional antibiotic selected from ciprofloxacin, cefepime, or meropenem;
wherein the compound and the additional antibiotic exhibit synergism.

In one embodiment, the synergistic composition comprises SM1 and ciprofloxacin. In one embodiment, the synergistic composition comprises SM1 and cefepime. In one embodiment, the synergistic composition comprises SM1 and meropenem. In one embodiment, the synergistic composition comprises SM3 and ciprofloxacin. In one embodiment, the synergistic composition comprises SM3 and cefepime. In one embodiment, the synergistic composition comprises SM3 and meropenem. In one embodiment, the synergistic composition comprises SM4 and ciprofloxacin. In one embodiment, the synergistic composition comprises SM4 and cefepime. In one embodiment, the synergistic composition comprises SM4 and meropenem. In one embodiment, the synergistic composition comprises SM5 and ciprofloxacin. In one embodiment, the synergistic composition comprises SM5 and cefepime. In one embodiment, the synergistic composition comprises SM5 and meropenem.

The subject can be any human or animal subject. For example, the subject can be a mammal (e.g., a human, dog, cow, horse, mouse, rabbit, non-human primate, etc.). In some embodiments, the subject is a livestock or farm mammal (e.g., sheep, goat, cow, pig, etc.) or, alternatively, a human. The subject can also be a non-mammal animal such as an avian subject (a bird). In some embodiments, the avian subject can be livestock or farm bird, for example poultry. For example, the subject can be a chicken, turkey, quail, duck, emu, goose, ostrich, pigeon, pheasant, rhea, guineafowl, or the like. Other non-mammal animal subjects include insects such as a moth, fly (e.g., fruit fly), beetle, ant, spider, butterfly, mosquito, flea, mantis, termite, cricket, grasshopper, bee, caterpillar, centipede, etc. In some embodiments, the subject is at risk for a bacterial infection, particularly a Salmonella infection, for example by housing in quarters in close proximity to other animals which can be or are infected with a bacterial infection. The subject can be a male or female of any age, size, or other general classifiers.

The infection typically comprises a bacterial infection. The infection can be a bacterial species which is pathogenic to the subject, or which infects the subject and is pathogenic to a downstream consumer of food products made from the subject. For instance, certain Salmonella species can infect poultry and can be pathogenic to poultry. Treating poultry via the disclosed methods can help prevent spread of Salmonella infections to additional poultry animals, thereby avoiding significant loss of poultry livestock. Salmonella can additionally be pathogenic to humans and other livestock animals which have poultry products included in their feed. Thus, treating poultry via the disclosed methods can also prevent Salmonella infections (e.g., salmonellosis) in humans and pigs which consume poultry products.

In some embodiments, the bacterial infection comprises a pathogenic bacteria, for example, Acinetobacter baumannii, Actinobacillus actinomycetemcomitans, Agrobacterium tumefaciens, Aggregatibacter actinomycelemcomilans, Bacillus (e.g., cereus, anthracis), Bacteroides forsythus, Branhamella catarrhalis, Bordetella pertussis, Borrelia (e.g., burgdorferi, garinii, afzelii, recurrentis), Brucella (e.g., abortus, canis, melitensis, suis), Campylobacter (e.g., jejuni, coli), Candidatus liberibacter, Citrobacter diversus, Chlamydia (e.g., pneumoniae, trachomatis, psittaci), Clostridium (e.g., botulinum, difficile, perfringens, tetani), Corynebacterium diphtheriae, Enterobacter aerogenes, Enterococcus (e.g., faecium, faecalis), Edwardsiella tarda, Escherichia coli, Francisella tularensis, Fusobacterium nucleatum, Haemophilus influenzae, Helicobacter pylori, Klebsiella pneumoniae, Legionella pheumophila, Listeria monocytogenes, Mycobacterium (e.g., tuberculosis, leprae, ulcerans), Mycoplasma pneumoniae, Morganella morganii, Neisseria (e.g., meningitidis, gonorrhoeae), Propionibacterium, Proteus mirabilis, Porphyromonas gingivalis, Pseudomonas aeruginosa, Rickettsia, Salmonella species (e.g., Salmonella enterica), Serratia marcescens, Shigella (e.g., sonnei, boydii), Staphylococcus (e.g., aureus, epidermidis, saprophyticus), Streptococcus (agalactiae, pneumoniae, pyogenes), Treponema pallidum, Ureaplasma urealyticum, Veillonella parvula, Vibrio cholera, Yersinia (e.g., pestis, enterocolitica, pseudotuberculosis), or combinations thereof.

In some embodiments, the bacterial infection comprises Salmonella (e.g., salmonellosis). There are numerous pathogenic Salmonella species, and the serovars of Salmonella number in the thousands. In some embodiments, the Salmonella species comprises Salmonella enterica. In some embodiments, the Salmonella species comprises a subspecies of *Salmonella enterica* (e.g., subspecies *enterica, houtenae, enteritidis*, etc.). In some embodiments, the *Salmonella* species comprises a serovar of *Salmonella enterica* subspecies *enterica* (e.g., Albany, Anatum, Braenderup, *Choleraesuis, Dublin, Enteritidis,* Galliformes, Hadar, Heidelberg, *Infantis,* Javiana, Muenchen, Newport, Paratyphi, Saint-Paul, *Typhi, Typhimurium,* or combinations thereof). In some embodiments, the infection is selected from a group of a *Salmonella enterica* serovars consisting of Albany, Anatum, Braenderup, *Enteritidis,* Heidelberg, Javiana, Muenchen, Newport, Saint-Paul, or *Typhimurium.*

In some or further embodiments, the infection comprises *Campylobacter jejuni, Escherichia coli, Mycoplasma gallisepticum,* or combinations thereof. These bacterial species are capable of infecting poultry and other livestock animals and can cause common food-borne illnesses in humans. *E. coli* contains hundreds of serotypes largely defined by the lipopolysaccharide O antigen and the flagellin H antigen, but also defined by the capsule K antigen. Often, *E. coli* serotypes are referred to only by their O antigen designations. In some embodiments, the *E. coli* comprises Avian Pathogenic *E. coli* (APEC). In some embodiments, the *E. coli* comprises *E. coli* O1, O2, O8, O15, O18, O35, O78, O109, O115, or O157. In some embodiments, the *E. coli* comprises *E. coli* O1, O2, O8, O15, O18, O35, O78, O109, or O115.

The bacteria can be actively growing or in a stationary or dormant phase. In some embodiments, the bacteria are in the form of a biofilm. A biofilm is a complex aggregate of microorganisms such as bacteria, wherein the cells adhere to each other on a surface. The cells in biofilms are physiologically distinct from planktonic cells of the same organism, which are single cells that can float or swim in liquid medium. Biofilms are involved in, for example, urinary tract infections, middle ear infections, dental plaques, gingivitis, coatings of contact lenses, cystic fibrosis, and infections of joint prostheses and heart valves.

The at least one compound, or derivate thereof, having the formula of SM1, SM3, SM4, or SM5, can be administered according to an array of dosing schedules. The compound can be administered in at least one, at least two, at least three, at least four, at least five, at least six, at least seven, at least eight, at least nine, or at least ten dosages. The administering step can be performed daily, weekly, or as needed. The administering step can be performed prior to, concurrent with, or subsequent to administration of other agents to the subject. In some embodiments, the administering step is performed prior to, concurrent with, or subsequent to the administration of one or more additional diagnostic or therapeutic agents.

In methods to treat a subject, the administering step can be performed during or after disease symptoms occur. In situations in which a first subject has a suspected or confirmed infection, the administering step can be performed as a risk-mitigating step on a second subject at risk of contracting the infection (e.g., prophylactically).

In methods to prevent a bacterial infection in a subject, the administering step can be performed prophylactically before disease symptoms occur. Preventive administrations can be made with or without regard to confirmed infections or risk of infection. For example, the administering step can be performed with regard to the timing of an event related to the subject. Poultry can be slaughtered for production of products or consumables, and thus, the administration step can be used to ensure clearance of potential infectious bacteria. Thus, in some embodiments, the administering step can be performed within one month or less, within three weeks or less, within two weeks or less, within one week or less, within six days or less, within five days or less, within four days or less, within three days or less, within two days or less, within 24 hours or less, or within 12 hours or less from the time of slaughter.

The methods comprise administering at least one compound, or derivate thereof, having the formula of SM1, SM3, SM4, or SM5. Dosages are typically modified according to the specific organism to be administered (e.g., chicken or human), the type or extent of infection (e.g., *Salmonella* or *E. coli*), the characteristics of the subject (weight, gender, age, etc.), specifics and purity of the compound, route of administration, nature of the formulation, and numerous other factors. Due to relative non-toxicity to host cells, the amount of SM administered to the subject, in some embodiments, can be large (milligram or gram amounts). Thus, in some embodiments, the amount of compound administered to the subject comprises about 100 mg or less or 10 mg or less. Due to good antimicrobial effectiveness, smaller doses can also be administered. Thus, in some embodiments, the amount of compound administered to the subject comprises about 1 mg or less, about 750 µg or less, about 500 µg or less, about 400 µg or less, about 300 µg or less, about 200 µg or less, or about 100 µg or less. Dosage amounts can also be expressed in terms of dose per body weight of the subject. Generally, a suitable effective dose is in the range of about 0.01 to about 500 mg/kg body weight. In some embodiments, the amount of compound administered to the subject comprises from about 0.01 mg/kg to about 100 mg/kg body weight, from about 0.05 mg/kg to about 10 mg/kg body weight, from about 0.1 mg/kg to about 10 mg/kg body weight, from about 0.2 mg/kg to about 5 mg/kg body weight, or from about 0.5 mg/kg to about 2.5 mg/kg body weight. In some embodiments, the amount of compound administered to the subject comprises about 1 mg/kg+/−0.5 mg/kg body weight. Dosages above or below these ranges may be administered to any individual subject if desired.

The compound can be administered by any herein disclosed method of administration. One form of administration which is simple, easy, and convenient for poultry producers includes oral administration. The compound can be formulated in feed product or hydration product which is provided to poultry and/or other livestock animals. For example, the compound can be mixed with the ingredients of the feed or hydration product during the production thereof. Alternatively, the compound can be mixed into feed or hydration product after the production thereof, for example after feed or hydration products are distributed to a farm but before being fed to poultry. In some or further embodiments, the compound can be contacted with the surface of a feed product, for example by spraying, misting, submerging, etc.

In some embodiments, the methods reduce the number of infectious cells within the subject. In some embodiments, the methods reduce the number of bacteria in the subject by at least 50%. In some embodiments, the methods reduce the number of bacteria in the subject by at least 75%, at least 80%, at least 85%, at least 90%, at least 95%, or at least 99%. In some embodiments, the methods reduce the number of bacteria in the subject by at least 0.5 log cfus, at least 1.0 log cfus, at least 1.5 log cfus, at least 2.0 log cfus, at least 2.5 log cfus, at least 3.0 log cfus, at least 3.5 log cfus, at least 4.0 log cfus, at least 4.5 log cfus, or at least 5.0 log cfus. In some embodiments, the methods sterilize the infection in the subject.

In some embodiments, the methods further comprise administering an antibiotic. The antibiotic can be administered prior to, concurrent with, or subsequent to administration of the at least one compound, or derivative thereof. The dosage of the antibiotic can be a typical dosage regimen for the animal type and size. However, the dosage of the antibiotic can, in some embodiments, be administered at a level below such typical dosages when administered in combination with the herein disclosed compounds. This is a result of additive or synergistic effects which occur in some embodiments comprising administration of at least one compound, or derivative thereof, having a formula of SM1, SM3, SM4, or SM5, and an antibiotic. Thus, in some embodiments, the antibiotic can be administered in a dose that is 75% or less, 50% or less, 25% or less, 10% or less, 5% or less, 2% or less, 1% or less, 0.5% or less, or 0.1% or less of the typical dosage of the antibiotic for the subject.

Suitable antibiotics which can be administered in the methods include, for example, glycopeptides (e.g., vancomycin or teicoplanin); penicillins, such as amdinocillin, ampicillin, amoxicillin, azlocillin, bacampicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin; quinolones and fluoroquinolones such as ciprofloxacin, nalidixic acid, gemifloxacin, levofloxacin, moxifloxacin, norfloxacin, and ofloxacin; cephalosporins, such as cefepime, cefadroxil, cefazolin, cephalexin, cephalothin, cephapirin, cephradine, cefaclor, cefamandole, cefonicid, ceforanide, cefoxitin, cefuroxime, cefoperazone, cefotaxime, cefotetan, ceftazidime, ceftizoxime, ceftriaxone, and moxalactam; carbapenems such as imipenem; monobactams such as aztreonam; tetracyclines such as demeclocycline, tigilcycline, doxycycline, methacycline, minocycline, and oxytetracycline; aminoglycosides such as amikacin, gentamicin, kanamycin, neomycin, netilmicin, paromomycin, spectinomycin, streptomycin, and tobramycin; polymyxins such as colistin, colistimathate, polymyxin B; macrolides such as erythromycin, lincomycin, azithromycin, carbomycin, cethromycin, clarithromycin, dirithromycin, mitemcinal, oleandomycin, roxithromycin, spiramycin, telithromycin, tylosin; sulfonamides such as sulfacytine, sulfadiazine, sulfisoxazole, sulfamethoxazole, sulfamethizole, and sulfapyridine; trimethoprim, novobiocin, pyrimethamine, rifampin, quinolines, fluoroquinolines, or combinations thereof.

In some embodiments, the method comprising administering an antibiotic comprising ciprofloxacin, cefepime, meropenem, erythromycin, cefotaxime, nalidixic acid, or combinations thereof. In some embodiments, the method comprising administering an antibiotic comprising ciprofloxacin, cefepime, meropenem, or combinations thereof.

Compounds having antimicrobial activities can be effective against narrow or broad ranges of microbes. For example, an antimicrobial with a narrow range of susceptible microbes can kill target microbes but have reduced or no effectiveness against other pathogenic microbes which infect the subject. To the contrary, an antimicrobial with a broad range of susceptible microbes can kill numerous types of microbes, including beneficial commensal bacteria which may be part of the subject's normal flora. Alteration of gut bacteria diversity influences degradation of complex molecules, production of metabolites, modulates resistance of the host toward enteric pathogens, and/or modulates the conditions for colonization by enteric pathogens. Thus, it can be advantageous to administer a compound effective against pathogenic organisms, but which do not affect the organisms present in the subject's normal flora, particularly the large amount of commensal enteric bacteria.

In some embodiments, the compound does not inhibit growth of at least one enteric microbiota organism. In some embodiments, the compound does not inhibit growth of at least one cecal microbiota organism. In some embodiments, the at least one enteric or cecal microbiota organism comprises *Clostridium clostridioforme, Bacteroides thetaiotaomicron, Bifidobacterium adolescentis, Bifidobacterium longum, Enterococcus faecalis, Lactobacillus brevis, Lactobacillus rhamnosus*, or combinations thereof. In some embodiments, the overall composition of the gut bacteria population is substantially (<10%) unchanged by administration of the compound.

In some instances, administration of agents can facilitate growth of beneficial commensal bacteria. For instance, an antimicrobial agent can reduce or eliminate competing bacteria, thereby facilitating the growth of bacteria unaffected by the antimicrobial agent. In some embodiments, the compound promotes growth of at least one enteric microbiota organism. In some embodiments, the compound promotes growth of at least one cecal microbiota organism. In some embodiments, the at least one enteric or cecal microbiota organism comprises Leuconostocaceae, *Lactobacillus*, Butyricicoccus pullicaecorum, or combinations thereof.

Similar to the desired reduced toxicity or nontoxicity for normal flora microorganisms, it is advantageous if administered agents have little to no toxicity to host cells. In some embodiments, the compound is nontoxic to the cells of the subject at the administered levels. Nontoxicity can be determined in a number of ways, for instance by in vitro cell survival assays. In some embodiments, administration of the compound does not significantly affect growth development of the subject (e.g., weight gain). In some embodiments, a subject administered with the compound increases in weight more than a subject with the same infection but not administered with the compound.

Optionally, the at least one compound, or derivative thereof, having the formula of SM1, SM3, SM4, or SM5, can be formulated in a medicament. The compound can be formulated in any suitable medicament including, for example, but not limited to, solids, semi-solids, liquids, and gaseous (inhalant) dosage forms, such as tablets, pills, powders, liquid solutions or suspensions, suppositories, injectables, infusions, inhalants, hydrogels, topical gels, sprays, and the like. Optionally, the medicament comprises a pharmaceutically acceptable excipient and/or suitable diluent. Typically, the medicament comprises an effective dose of the at least one compound.

Compositions and Methods for Inhibiting Bacterial Growth in a Plant

Additionally disclosed herein are methods of inhibiting bacterial growth in a plant comprising contacting the plant with an effective amount of at least one compound, or a derivative thereof, having the following formula:

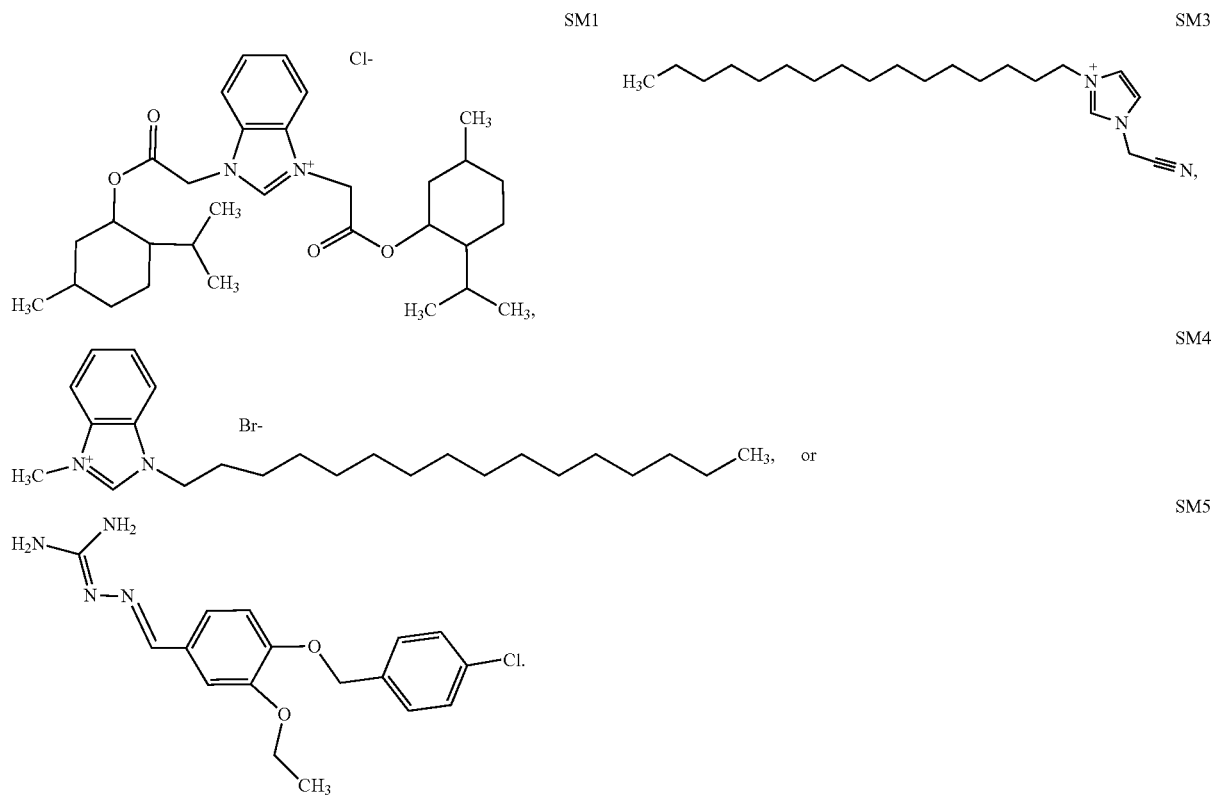

In some embodiments, the compound is contacted with a plant, plant seed, fruit, vegetable, or a leaf. In some embodiments, the plant comprises a tomato plant.

In some embodiments, the method inhibits the bacterial growth of *Salmonella*. Many *Salmonella* species can persist in plants and be transmitted to humans through contact with or consumption of contaminated plants or portions thereof (e.g., edible leaves, vegetables, fruits, etc.). There are numerous *Salmonella* species, and the serovars of *Salmonella* number in the thousands. In some embodiments, the *Salmonella* species comprises *Salmonella enterica*. In some embodiments, the *Salmonella* species comprises a subspecies of *Salmonella enterica* (e.g., subspecies *enterica, houtenae, enteritidis*, etc.). In some embodiments, the *Salmonella* species comprises a serovar of *Salmonella enterica* subspecies *enterica* (e.g., Albany, Anatum, Braenderup, *Choleraesuis*, Dublin, *Enteritidis*, Galliformes, Hadar, Heidelberg, *Infantis*, Javiana, Muenchen, Newport, Paratyphi, Saint-Paul, *Typhi, Typhimurium*, or combinations thereof). In some embodiments, the method inhibits the bacterial growth of one or more *Salmonella enterica* serovars. In some embodiments, the one or more *Salmonella enterica* serovars are selected from a group consisting of Albany, Anatum, Braenderup, *Enteritidis*, Heidelberg, Javiana, Muenchen, Newport, Saint-Paul, or *Typhimurium*.

The bacterial growth for which the method inhibits can be actively growing or in a stationary or dormant phase. In some embodiments, the bacterial growth for which the method inhibits can be in the form of a biofilm.

In some embodiments, the compound inhibits bacterial growth of at least one phytopathogen comprising *Acidovorax citrulli, Agrobacterium rhizogenes, Clavibacter michiganensis, Erwinia amylovora, Erwinia tracheiphila, Pseudomonas syringae, Serratia marcescens, Xanthomonas cucurbitae, Xanthomonas gardneri*, or *Xanthomonas perforans*. In some embodiments, the compound does not inhibit growth of at least one plant-commensal bacterial organism.

In some embodiments, the at least one compound can comprise 1,3-bis{2-[(2-isopropyl-5-methylcyclohexyl)oxy]-2-oxoethyl}-1H-3,1-benzimidazol-3-ium chloride (SM1); 1-(cyanomethyl)-3-hexadecyl-1H-imidazol-3-ium chloride (SM3); 1-hexadecyl-3-methyl-1H-3,1-benzimidazol-3-ium bromide (SM4); N″-{4-[(4-chlorobenzyl)oxy]-3-ethoxybenzylidene}carbonohydrazonic diamide (SM5), or a derivative of any of the foregoing. In some embodiments, the compound comprises 1-(3,6-dibromo-9H-carbazol-9-yl)-3-[(2-hydroxyethyl)(methyl)amino]-2-propanol (SM2) or a derivative thereof. In some embodiments, the compound comprises 1-[benzyl(methyl)amino]-3-[4-({[(5-chloro-2-thienyl)methyl]amino}methyl)phenoxy]-2-propanol (SM6), 2,4-dichloro-6-{[(2-fluoro-5-nitrophenyl)imino]methyl}phenol (SM7), 2,4-dichloro-6-{[(3-methoxyphenyl)imino]methyl}phenol (SM8), N-[1-(4-isobutylbenzyl)-3-piperidinyl]-2-(4-methyl-1,4-diazepan-1-yl)acetamide (SM9), ethyl 5-acetyl-2-amino-4-methyl-3-thiophenecarboxylate (SM10), 4-[1-(3-methoxyphenyl)cyclopentyl]phenol (SM11), 3-[3-(4-bromophenyl)-2-triazen-1-yl]-5-nitrobenzoic acid (SM12), 1-benzyl-N-[2-(2,4-dichlorophenyl)ethyl]-4-piperidinamine (SM13), 1-(1-azocanyl)-3-(2-methoxy-5-{[(4-methylbenzyl)amino]methyl}phenoxy)-2-propanol (SM15), 4-bromo-2-{[(3-methoxyphenyl)imino]methyl}phenol (SM16), 1-methyl-5-[(5-nitro-2-furyl)methylene]-2,4,6(1H,3H,5H)-pyrimidinetrione (SM17), 4-benzoyl-5-methyl-2-phenyl-2,4-dihydro-3H-pyrazol-3-one (SM18), 1-(9H-fluoren-9-yl)-4-(3-phenyl-2-propen-1- yl)piperazine (SM19), or a derivative of any of the foregoing. Derivatives of a compound include, but are not limited to, any salt, ester, acids, bases, solvates, hydrates, prodrugs, etc. Derivatives, modifications and pharmaceutically acceptable salts retain the functional properties described herein.

The plant can be any plant capable of being subject to bacterial growth on or within the plant. As used herein, the term "plant" is intended to encompass any and all plants in the plant kingdom. In some embodiments, the plant can be a subsistence, commercial, or cash crop (e.g., tomato, soybean, cotton, sugarcane, tobacco, pepper, tea, coffee, cocoa, wheat, rice, corn, potato, grape, legume, banana, orange, broccoli, lettuce, apple, mango, onion, peanut, olive, cucumber, yam, peach, sunflower, carrot, tangerine, almond, lemon, lime, walnut, strawberry, cauliflower, bean, bamboo, hemp, oil palm, coconut, etc.). In some embodiments, the subject is a fruiting plant (e.g., tomato, pepper, grape, strawberry, blueberry, cherry, blackberry, apricot, orange, apple, lemon, lime, fig, mango, watermelon, grapefruit, coconut, avocado, kiwi, olive, papaya, tangerine, pomegranate, guava, cantaloupe, cranberry, lychee, date, persimmon, quince, pomelo, pear, passion fruit, kumquat, jujube, boysenberry, banana, etc.). In some embodiments, the plant is a Solanaceae family plant. In some embodiments, the plant is a Solanaceae *Solanum* genus plant. In some embodiments, the plant is *Solanum lycopersicum* (tomato). In some embodiments, the plant is at risk for containing bacteria which can grow in the plant; for example, by growing in a field in close proximity to another plant which can contain or does contain bacterial growth. In some embodiments, the plant includes a fruit, a vegetable, or a seed produced by the plant. As used herein, bacterial growth "in" a plant includes bacterial growth occurring on a surface of the plant as well as bacterial growth occurring within the plant. In some embodiments, the bacterial growth in a plant comprises *Salmonella*. In some embodiments, the bacterial growth in a plant comprises a phytopathogen.

The bacterial growth for which the method inhibits can be that of any bacterial species capable of growth on a plant and susceptible to an effective amount of at least one compound, or a derivative thereof, having the formula of SM1, SM3, SM4, or SM5. In some embodiments, the method inhibits the bacterial growth of at least one phytopathogen. A phytopathogen is an organism pathogenic to one or more plants. A bacterial phytopathogen is a phytopathogen which is a bacterial organism. The bacterial phytopathogen can be a bacterial species which is pathogenic to the plant alone, or also to a downstream consumer of products made from the plant (e.g., edible or cosmetic products). For instance, *Serratia marcescens* can be pathogenic to certain melon plants (causing, e.g., cucurbit yellow vine disease). Treating melons via the disclosed methods can help prevent growth and spread of *S. marcescens* infections to additional susceptible plants, thereby avoiding significant loss of crop yields. *S. marcescens* can additionally be pathogenic to humans and other animals which contact or consume *S. marcescens*-contaminated products. Thus, treating plants via the disclosed methods can also prevent *S. marcescens* infections (e.g., urinary tract infection, conjunctivitis, meningitis) in humans and animals (e.g., livestock) which contact or consume plant products.

In some embodiments, the method inhibits the bacterial growth of at least one phytopathogen from at least one genus comprising Acidovorax, *Agrobacterium*, *Arthrobacter*, *Bacillus*, *Clavibacter*, *Clostridium*, *Corynebacterium*, *Erwinia*, *Leifsonia*, *Pantoca*, *Pseudomonas*, *Ralstonia*, *Rhizomonas*, *Rhizobacter*, *Rhodococcus*, *Serratia*, *Sphingomonas*, *Streptomyces*, *Xanthomonas*, *Xylella*, or combinations thereof. In some embodiments, the method inhibits the bacterial growth of at least one phytopathogen from at least one genus comprising *Acidovorax*, *Agrobacterium*, *Clavibacter*, *Erwinia*, *Pseudomonas*, *Serratia*, *Xanthomonas*, or combinations thereof.

In some embodiments, the method inhibits the bacterial growth of at least one phytopathogen comprising *Acidovorax citrulli*, *Agrobacterium* (e.g., *rhizogenes*, *tumefaciens*, *rubi*, *vitis*), *Candidatus Liberibacter asiaticus*, *Clavibacter* (e.g., *michiganensis*, *sepedonicus*), *Corynebacterium insidiosum*, *Dickeya* (e.g., *dadantii*, *solani*), *Erwinia* (e.g., *amylovora*, *stewartii*, *tracheiphila*), *Pectobacterium* (e.g., *atrosepticum* and *carotovorum*), *Pseudomonas* (e.g., *savastonoi*, *solanacearum*, *syringae*), *Ralstonia solanacearum*, *Serratia marcescens*, *Xanthomonas* (e.g., *axonopodis*, *campestris*, *cucurbitae*, *gardneri*, *oryzae*, *perforans*), *Xylella fastidiosa*, or combinations thereof. In some embodiments, the method inhibits the bacterial growth of at least one phytopathogen comprising Acidovorax *citrulli*, *Agrobacterium rhizogenes*, *Clavibacter michiganensis*, *Erwinia amylovora*, *Erwinia tracheiphila*, *Pseudomonas syringae*, *Serratia marcescens*, *Xanthomonas cucurbitae*, *Xanthomonas gardneri*, *Xanthomonas perforans*, or combinations thereof.

The at least one compound, or derivate thereof, having the formula of SM1, SM3, SM4, or SM5, can be contacted with a plant (including fruit, vegetables, or seeds, for example, tomatoes) according to an array of dosing schedules. The compound can be contacted with a plant in at least one, at least two, at least three, at least four, at least five, at least six, at least seven, at least eight, at least nine, or at least ten dosages. The contacting step can be performed daily, weekly, or as needed. The contacting step can be performed prior to, concurrent with, or subsequent to contacting other agents to the plant. In some embodiments, the contacting step is performed prior to, concurrent with, or subsequent to the contacting of one or more additional diagnostic or therapeutic agents.

In methods to treat a plant, the contacting step can be performed during or after disease symptoms occur. In situations in which a first plant has a suspected or confirmed infection, the contacting step can be performed as a risk-mitigating step on a second plant at risk of contracting the infection (e.g., prophylactically).

In methods to prevent bacterial growth or a bacterial infection in a plant, the contacting step can be performed prophylactically before disease symptoms occur. Preventive contacting can be made with or without regard to confirmed infections or risk of infection. For example, the contacting step can be performed with regard to the timing of an event related to the plant. Plants can be harvested for production of products and consumables, and thus, the contacting step can be used to ensure clearance of potential infectious bacteria. Thus, in some embodiments, the contacting step can be performed within one month or less, within three weeks or less, within two weeks or less, within one week or less, within six days or less, within five days or less, within four days or less, within three days or less, within two days or less, within 24 hours or less, or within 12 hours or less from the time of harvest.

The methods comprise contacting a plant with at least one compound, or derivate thereof, having the formula of SM1, SM3, SM4, or SM5. Dosages are typically modified according to the specific organism to be contacted (e.g., tomato plant or grape vine), the type or extent of bacterial growth (e.g., *Salmonella* or *Erwinia*), the characteristics of the plant (stage of development, size, etc.), specifics and purity of the compound, route of administration, nature of the formulation, and numerous other factors. In some embodiments, the amount of compound contacted to the plant comprises about 10 mg or less, about 1 mg or less, about 750 µg or less, about 500 µg or less, about 400 µg or less, about 300 µg or less, about 200 µg or less, about 100 µg or less, about 50 µg or less, or about 25 µg or less. In some embodiments, the amount of compound contacted to the plant comprises about 200 µg or less. Because the compound can be administered to a plant topically (e.g., by spraying, misting, submerging, etc.), the amount of the compound contacted to the plant can be expressed in terms of concentration in a liquid carrier. Due to relative nontoxicity to host cells, the concentration of compound contacted to the plant can comprise, in some embodiments, about 1 M or less or about 100 mM or less. Due to good antimicrobial effectiveness, the concentration of compound contacted to the plant can comprise, in some embodiments, about 10 mM or less, about 1 mM or less, about 800 µM or less, about 500 µM or less, or about 200 µM or less.

The compound can be contacted with the plant by any method suitable for applying a chemical compound to a plant. In some embodiments, the compound can be contacted with the plant by providing the compound in a liquid dispensed on or near the plant. For example, the compound can be formulated in a liquid that is sprayed or misted onto a plant or a portion of a plant (e.g., leaf, fruit or seed). In some embodiments, the plant or plant portion is submerged in a liquid formulation comprising the compound. In some embodiments, the compound can be contacted with the plant by combining the compound with a water source of an irrigation system, which is then used to irrigate the plant or field of plants.

The compound can, in some embodiments, be contacted with any portion of the plant and at any stage of growth of the plant. In some embodiments, the compound is contacted with any one or more portions of the plant comprising leaf, stem, flower, fruit (fruiting body), trunk, branch, root, or seed. In some embodiments, the compound is contacted with a seed, a seedling, an immature plant (a plant not yet bearing fruit), or a mature plant (a plant bearing fruit or having previously bore fruit). In some embodiments, the compound is contacted with the plant during or after planting (or transplanting) the plant into a position for eventual harvest. For example, the compound can be contacted with a plant which is planted in a crop field or in a greenhouse for commercial fruit, vegetable, leaf, or spice production. In some embodiments, the compound is contacted with the plant prior to planting (or transplanting) the plant into a position for eventual harvest. For example, the compound can be contacted with a plant seed or seedling which is later planted or transplanted for eventual harvest.

In some embodiments, the inhibition of bacterial growth comprises reducing the number of bacterial cells in the plant. In some embodiments, the methods reduce the number of bacterial cells in the plant by at least 50%. In some embodiments, the methods reduce the number of bacterial cells in the plant by at least 75%, at least 80%, at least 85%, at least 90%, at least 95%, or at least 99%. In some embodiments, the methods reduce the number of bacterial cells in the plant by at least 0.5 log cfus, at least 1.0 log cfus, at least 1.5 log cfus, at least 2.0 log cfus, at least 2.5 log cfus, at least 3.0 log cfus, at least 3.5 log cfus, at least 4.0 log cfus, at least 4.5 log cfus, or at least 5.0 log cfus. In some embodiments, the methods sterilize the bacterial cells in the plant. In some embodiments, the bacteria cells having a reduced number in the methods are bacteria cells of one or more phytopathogens. In some embodiments, the bacteria cells having a reduced number in the methods are bacteria cells of one or more zoonotic pathogens capable of bacterial growth in a plant (e.g., *Salmonella*). A zoonotic pathogen is a pathogen of animals such as humans.

In some embodiments, the compound does not inhibit growth of at least one plant-commensal bacterial organism. A plant-commensal bacterial organism is a bacterium which is beneficial for plants (e.g., facilitates plant growth) and does not cause disease in the plant. A plant-commensal bacterial organism may be found naturally in the environment near a plant (e.g., in soil or water sources) and naturally associate with the plant, or may be provided to the plant or soil extrinsically. In some embodiments, the at least one plant-commensal bacterial organism comprises *Bacillus subtilis, Bacillus amyloliquefaciens, Enterobacter, Lysobacter enzymogenes, Mitsuaria, Pseudomonas fluorescens, Pseudomonas chlororaphis,* or *Pseudomonas protegens, Streptomyces*, or combinations thereof. In some embodiments, the at least one plant-commensal bacterial organism comprises *Bacillus subtilis, Bacillus amyloliquefaciens, Enterobacter,* or *Pseudomonas chlororaphis*, or combinations thereof.

It is advantageous if contacted compounds have little to no toxicity to plant host cells. In some embodiments, the compound is nontoxic to the cells of the plant at the levels used for contacting.

Also disclosed herein are methods of preventing a bacterial infection in a plant comprising contacting the plant with an effective amount of at least one compound, or a derivative thereof, having the following formula:

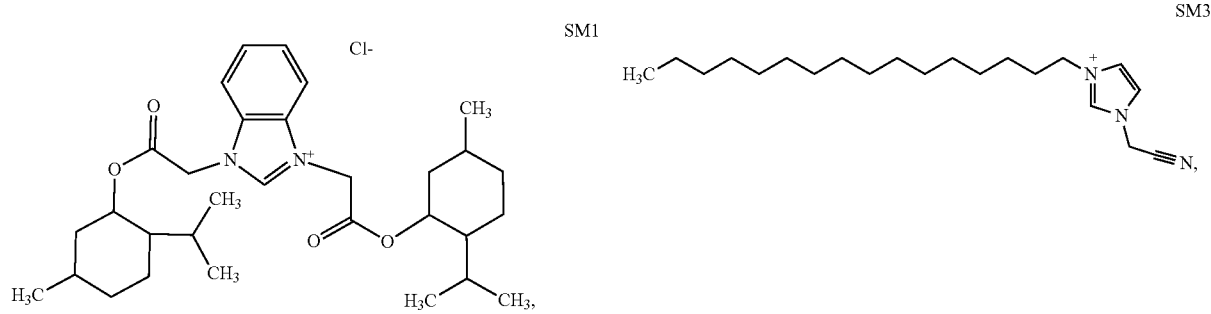

-continued

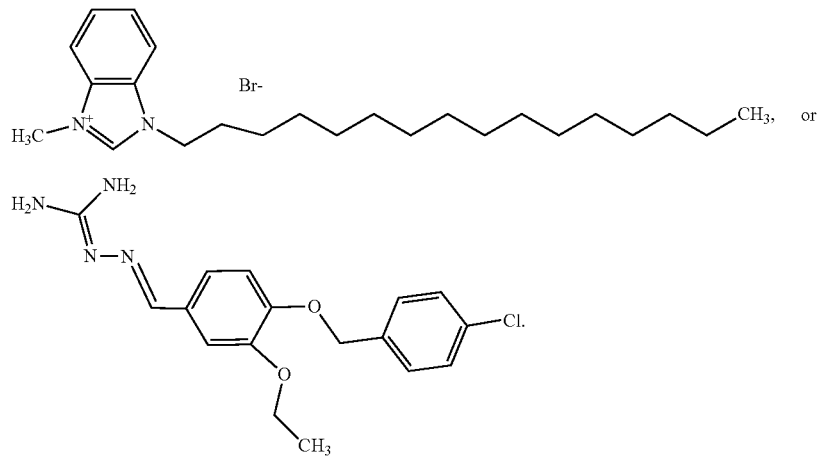

Also disclosed herein are methods of treating a plant with a bacterial infection comprising contacting the plant with an effective amount of at least one compound, or a derivative thereof, having the following formula:

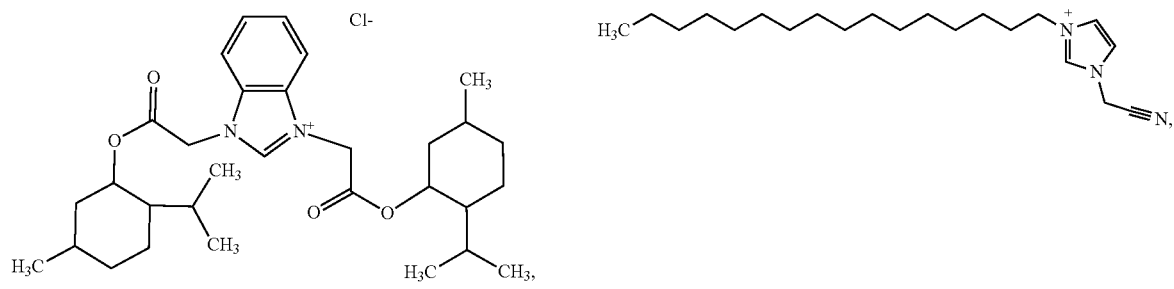

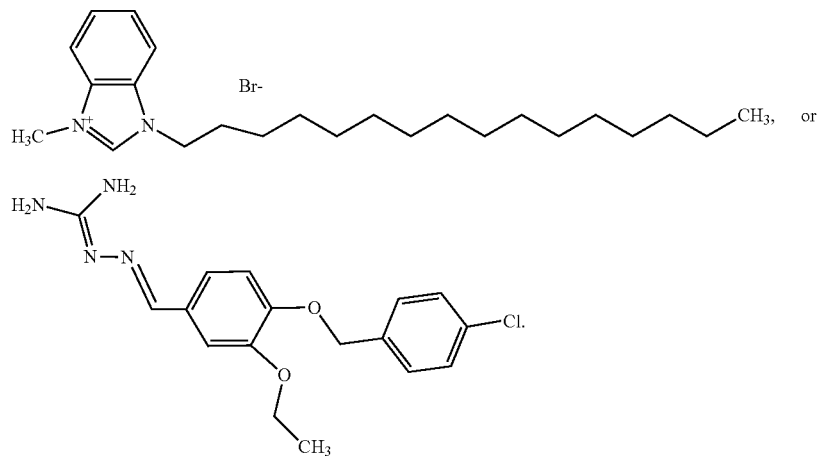

EXAMPLES

To further illustrate the principles of the present disclosure, the following examples are put forth so as to provide those of ordinary skill in the art with a complete disclosure and description of how the compositions and methods claimed herein are made and evaluated. They are intended to be purely for purposes of example and are not intended to limit the scope of the disclosure. These examples do not exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1. Control of *Salmonella* in Animal Models Using New Generation Small Molecule Inhibitors Current antimicrobial treatments have become old and obsolete, and their effects are limited or easily overcome by foodborne pathogens such as *Salmonella*. Advanced chemical technologies have made accessible a wide range of small molecules (SMs) with encouraging chemical properties for antimicrobial treatment; however, few studies have been performed with them. This study screened in high throughput a pre-selected library of 4182 SMs to identify growth inhibitors against *Salmonella enterica*. 128 growth inhibitors identified, of which five novel SMs were selected based on their in vitro potency against numerous *Salmonella* serotypes. Of these, four cidal SMs were identified with a broad antimicrobial activity at low concentration against several *Salmonella* serotypes and other avian-pathogens. These four SMs had synergetic or additive antimicrobial effects with ciprofloxacin, cefepime, and Meropenem against *Salmonella*, similar antimicrobial activity against biofilm-protected *Salmonella*, limited antimicrobial activity against twelve beneficial gut bacteria, and no toxicity to most eukaryotic models tested. Moreover, they successfully increased longevity of *G. mellonella* (wax moth) larvae survival by reducing the population of internalized *S. typhimurium*, and also decreased *S. typhimurium* load in ceca and in systemic tissues of infected broilers. Further, metagenomic analysis showed SM4 and SM5 were effective in controlling *Salmonella* in chickens with minimal impact on chicken cecal microbiota.

Without being bound to any one particular theory, SM4 and SM5 treatments in chicken may have increased producers of short chain fatty acid metabolites and thereby potentially enhanced the production of butyrate, a well-characterized molecule for its anti-*Salmonella* properties and health benefits on the host. This study demonstrated new generation SMs applicable as antimicrobials in animal production against foodborne pathogens.

Materials and Methods

Prokaryotic-eukaryotic models and culture conditions: *Salmonella enterica* subsp. *enterica* serovar Typhimurium LT2 strain (*S. typhimurium* wild-type; WT) was used as the primary strain for the identification of growth inhibitors. Additional *Salmonella* serotypes and beneficial-commensal gut bacteria were used for activity spectrum characterization. Three cell lines were used to evaluate the cytotoxicity and *Salmonella* clearance ability of the SMs: Caco-2 cell line (human colonic carcinoma; American Type Culture Collection, Rockville, MD); HD-11 cell line (chicken macrophages, CVCL_4685); and THP-1 cell line (human macrophages, ATCC® TIB-202TM). A kanamycin resistant *S. typhimurium* strain (*S. typhimurium* Kan$^R$) was created for the clearance efficacy studies on infected *Galleria mellonella* larva and broiler chickens to increase the accuracy of the colony counting. Details about the organism's growth conditions are displayed in Table 1:

TABLE 1

Organisms and Growth Conditions

| Organisms | Growth Conditions |
| --- | --- |
| Bacterial strains | |
| *Bacteroides thetaiotaomicron* | MRS broth, 37° C., anaerobic for 4-5 days |
| *Bifidobacterium adolescen-s, lac-s* Bb12, *longum* | MRS + Cysteine broth, 37° C., anaerobic for 24 hrs |
| *Clostridium clostridioforme* | BHI + 5% Horse blood, 37° C., anaerobic for 7 days |
| *Enterococcus faecalis* | MRS broth, 37° C., anaerobic for 18 hrs |
| *Escherichia coli* G58-1, Nissle strain | LB broth, 37° C., aerobic for 12 hrs |
| *Lactobacillus acidophilus, brevis, rhamnosus* GG | MRS broth, 37° C., anaerobic for 2 days |
| *Salmonella* Albany, Anatum, Braenderup, Enteritidis, Heidelberg, Javiana, Muenchen, Newport, Saint-Paul, Typhimurium | Adjusted M9 minimal broth, 37° C., aerobic for 12 hrs |
| *Salmonella* Typhimurium KAN$^R$ mutant | Adjusted M9 minimal broth, 37° C., aerobic for 12 hrs |
| *Streptococcus bovis* | MRS broth, 37° C., anaerobic for 18 hrs |
| Eukaryotic organisms | |
| Caco-2 cells | MEM + 20% FBS + 1% NEAA + 1 mM sodium pyruvate |
| HD-11 cells (CVCL_4685) | IMEM + 2 mM glutamine + 10% FBS |
| THP-1 cells(ATCC*TIB-202TM) | RPMI 1640 + 10% FBS + 2 mM Glutamine + 100 nM PMA |
| Sheep red blood cells | None |
| Chicken red blood cells | None |
| *Galleria mellonella* (wax moth) fifth instar larva stage | Petri dish + filter paper |
| Broiler chickens | Metallic cage, at 27° C. |

SM library: A library of 4182 bioactive small molecules (SMs) obtained from ChemBridge (San Diego, CA, USA) was used. Additional details about the SM library are described in (9). The SMs were suspended into 100% dimethyl sulfoxide (DMSO) and stored at −80° C. in 96-well plate sealed with aluminum tape.

Creation of *S. typhimurium* Kan$^R$ mutant: The *S. typhimurium* Kan$^R$ strain was created using pUWGR4 plasmid as described in (10). Preparation of the *S. typhimurium* WT competent cells was performed following a protocol provided by Bio-rad (#3112_54). Then, 2 μl of transposable kanamycin gene construction and 100 μl of the competent cells were transferred to an ice-cold electroporation cuvette (Eurogentech #CE-0002, 2 mm gap). Cells were transformed with a MicroPulser™ (Biorad) at 2,400 V, 25 μF, and 400Ω. Immediately after electroporation, 900 μl SOC media was add to the product of the electroporation, and transferred into a 1.5 ml Eppendorf® tube to be incubated at 30° C., 150 rpm for 90 min. The suspension was streaked on XLT-4 agar plates supplemented with 50 μg/ml kanamycin and incubated up to three days at 37° C. A colony polymerase chain reaction (PCR) assay was performed to confirm the presence of the Kan$^R$ gene (837 base pairs). The PCR program included an initial 5 min denaturation step at 95° C., followed by 30 cycles of denaturation, annealing, and elongation with 30 sec at 94° C., 40 sec at 45° C., and 60 sec at 72° C. respectively. Amplification was completed with a final elongation step at 72° C. for 2 min. Products of the reaction were analyzed on 1% agarose gel.

In vitro stability of insertion: The in vitro stability of the pUWGR4 insertion was tested as described (11). Briefly, an overnight bacterial suspension of Kan$^R$ and WT *S. typhimurium* were normalized at 0.01 OD$_{600}$ (approximately 5×10$^6$ CFU/ml) into fresh Luria broth (LB) medium. 100 μL bacterial suspension were transferred into four wells of a sterile, non-treated, flat bottom 96-well plate and incubated into a Sunrise™ Tecan kinetic microplate reader (Tecan US, Inc., San Jose, CA, USA) for 12 hrs at 37° C. Every 15 min, the optical density was measured at 600 nm after 30 seconds of agitation at normal intensity (approximately 200 rpm). After the first 12 hrs of incubations, bacterial suspensions were normalized at 0.01 OD$_{600}$ in fresh LB medium and the plate was incubated following the same steps described above. The procedure was repeated ten times in total. Between passages, the bacterial population was monitored via spectrometric reads at 600 nm. At the end of the ten passages, bacterial suspensions were serial ten-fold diluted, plated on XLT-4 agar plate with and without kanamycin (50 μg/ml), and incubated at 37° C. for 24 hrs. Colony counts obtained between strains and growth conditions were compared together.

Identification of *S. typhimurium* growth inhibitors: The 4182 small molecules (SMs) were screened at 200 μM against *S. typhimurium* WT using HTS assay in a 96-well plate format. An overnight *Salmonella* suspension was normalized at 0.05 OD$_{600}$ (approximately 3.5×10$^7$ CFU/ml) with an adjusted M9 minimal broth medium (12.7 mM Na$_2$HPO$_4$ 7H$_2$O; 22 mM KH$_2$PO$_4$; 18.7 mM NH$_4$Cl; 2 mM MgSO$_4$; 0.1 mM CaCl$_2$; 0.4% glucose; 0.05% casamino acids). 100 μL of the suspension plus 2 μl of SMs (200 μM) were transferred into each well of a sterile, non-treated, flat bottom 96-well plate. Bacteria alone (negative control, NC), 2% DMSO plus bacteria (DMSO control), 20 μg/ml chloramphenicol or 50 μg/ml kanamycin plus bacteria (positive controls, PC), and M9 medium only were used as control. Plates were incubated in a Sunrise™ Tecan kinetic microplate reader for 12 hrs at 37° C. and the optical density (OD) was measure at 600 nm as described above. Percentage of inhibition=(OD$_{600\ SM}$−OD$_{600\ NC}$)/(OD$_{600\ NC}$)×100. SMs were identified as growth inhibitors if their inhibition value after incubation was above 20% (value representing the inhibition level monitored with the DMSO controls). Cultures from wells showing no turbidimetric increase were transferred onto a XLT4 agar plate. Plates were incubated at 37° C. for 36 hrs. As used herein, SMs that displayed 100% growth inhibition and no growth on XLT4 agar plate were considered as bactericidal at 200 μM, while SMs were considered as bacteriostatic agents if they displayed 100% growth inhibition but growth on XLT4 agar plate.

SM activity spectrum: The 128 selected SMs were tested for antimicrobial effects on nine different serotypes frequently implicated in foodborne gastroenteritis outbreaks. Later in the study, the four best SMs were tested against twelve beneficial/commensal gut bacteria. Both screens were performed at 200 μM as described in the primary screening. Growth conditions for each strain are described in Table 1.

MIC and MBC determination: The selected 19 SMs were serial diluted with final SM concentrations ranging between 400 μM to 2.5 μM. Screens were performed as described in the primary screen. The lowest SM concentration with a static effect was considered as the minimal inhibitory concentration (MIC) and the lowest SM concentration with a cidal effect was considered as the minimal bactericidal concentration (MBC).

Antimicrobial resistance studies: Single step and sequential passage resistance assays were performed as described (9). The MIC of the selected five SMs against *S. typhimurium* WT was used as reference for lethal (2×MIC) and sub-lethal (0.75×MIC) doses.

Evaluation of antimicrobial resistance to SMs following a single passage with a lethal dose: SMs were mixed into 1 ml of molten adjusted M9 agar medium at a final concentration of 2×MIC and transferred to one well of a sterile, treated, flat bottom 24-well plate. The medium was allowed to solidify overnight in the dark at room temperature. The next day, 100 μl of *S. typhimurium* bacteria (approximately 109 CFU) was transferred onto the adjusted M9 agar containing 2×MIC of SMs. *S. typhimurium* WT growth in 2% DMSO, 20 μg/ml chloramphenicol, or 50 μg/ml kanamycin, and adjusted M9 medium only were used as controls. The plate was sealed with parafilm and incubated for 15 days in the dark at 37° C. After 15 days, 100 μl of LB broth was added to the wells of 24-well plate showing no colonies in order to resuspend the potential surviving bacteria and transferred into a 5 ml tube. After 12 hrs of incubation at 37° C., 150 rpm, tubes showing an increase in density and any colonies that grew on the agar were selected for MIC and MBC determination.

Evaluation of antimicrobial resistance to SMs following sequential passages at sub-lethal dose: *S. typhimurium* WT was challenged with of 0.75×MIC of SMs (concentration allowing at least 70% growth inhibition) as described in the primary screening. The plate was incubated in the dark at 37° C., 175 rpm for 12 hrs. After this first passage, the plate was centrifuged for seven min at 4500 rpm. Supernatant was replaced with a fresh adjusted M9 broth media amended with 0.75×MIC of the corresponding SM. This procedure was repeated fourteen times. Following the 15th passage, a dose-response assay was performed on the remaining alive *S. typhimurium* bacteria as describe previously.

Antimicrobial susceptibility testing on biofilm-protected *S. typhimurium* using the MBEC™-HTP assay: The antimicrobial efficacy of the four SMs was tested once the *S. Typhimurium* WT was protected by the for a biofilm matrix. The experiment was performed as described by the manufacturer (innovotech.ca/MBEC_HTPInstructions_Rev1.pdf). Briefly, 150 μl of an overnight suspension of *S. typhimurium* WT normalized at 0.05 OD$_{600}$ in LB medium was transferred into each well of a sterile, non-treated, flat bottom 96-wells plate. The plate was covered using the lid containing the pegs (innovotech; 19111), sealed with parafilm, and incubated for 36 hrs at 37° C. After incubation, the lid was soaked for 30 sec into a 96-wells plate containing 175 μl of sterile water and transferred into a new 96-wells plate containing 200 μl of adjusted M9 medium supplemented with 0.2×MBC to 4×MBC of SMs. *S. typhimurium* WT challenged with 1% DMSO or a specific concentration of kanamycin (between 0.4×MBC to 4×MBC) were used as controls. The plate was incubated for 18 hrs at 37° C., 110 rpm in the dark. After incubation, the lid was transferred into a new 96-wells plate containing 200 µl of sterile water and sonicated for 60 min at room temperature (Aquasonic model 50HT, VWR). Then the supernatant was ten-fold serial diluted, plated in agar plate, and incubated at 37° C. for 36 hrs. The lowest SM concentration giving a complete clearance was considered as the minimum biofilm eradication concentration (MBEC).

Combined antimicrobial study between antibiotics and small molecules (SMs): The antimicrobial efficacy of several antibiotics commonly used to control *Salmonella* was studied once combined with the selected four SMs. A total of six antibiotics (Cefotaxime, Cefepime, Ciprofloxacin, Erythromycin, Nalidixic acid, and Meropenem) were tested on *Salmonella* in minimal growth condition. 100 µL of a *S. typhimurium* WT suspension normalized at 0.05 $OD_{600}$ in an adjusted M9 minimal broth medium was transferred in each well of a sterile, non-treated, flat bottom 96-well plate. A specific concentration of SMs and antibiotics ranging between 0.2×MBC and 1×MBC was added to each well. The MBC of each antibiotic were pre-determined as described previously. Bacteria challenged with only SMs or antibiotics at the same concentrations were used to determine the ATB-SM combination effects. Bacteria alone (negative control), supplemented with 2% DMSO (DMSO control), or 50 µg/ml kanamycin (positive control), and adjusted M9 medium only were used as control. Plates were incubated in a Sunrise™ Tecan kinetic microplate reader for 12 hrs at 37° C. and the optical density (OD) was measure at 600 nm as described above. After challenging, survival was recorded following plating of the bacterial suspension on agar plate and incubated at 37° C. for 36 hrs. The ATB-SM combination effect was calculated as described in Doern CD, 2014 (12).

Cytotoxicity of the selected four SMs in cell lines: Cytotoxicity of the SMs was tested as described (9). Briefly, a sterile, treated, flat bottom 96-well plate was seeded with 150 µl of suspended Caco-2 cells (approximately $1.4 \times 10^5$ cells per well) and incubated at 37° C. in humidified 5% $CO_2$ incubator. Once a confluent monolayer was formed, cells were washed three times with 1× phosphate-buffered saline (PBS) and grown in 150 µl of appropriate broth medium supplemented with 2 µl of SMs (200 µM). After 24 hrs of incubation at 37° C. in humidified 5% $CO_2$ incubator, cytotoxicity levels were determined using the Pierce™ Lysine Dehydrogenase Cytotoxicity Assay Kit (ThermoFisher Scientific). For this experiment 2% DMSO and 10× lysis buffer were used as control. The cytotoxicity level was calculated based on the kit instructions.

Hemolytic activity of the selected four SMs in RBCs: The hemolytic activity of the most potent SMs was demonstrated as previously described (13). Briefly, 200 µl of 10% sheep red blood cells (RBCs; LAMPIRE Biological Laboratories, Pipersville, PA) suspension was incubated with 1 µl of SMs (200 µM) for one hour at 37° C. in a sterile, non-treated, flat bottom plate 96-well. After incubation, the plate was centrifuged at 4000 rpm for 5 min at 4° C., then placed on ice for five min. 100 µL of the supernatant was transferred into a new sterile, treated, flat bottom 96-well plate, and the OD was measured at 540 nm. For this experiment, 2% DMSO (negative control) and 0.1% Triton-100X (positive control) were used. % Hemolysis=$(OD_{540\ SM}-OD_{540\ DMSO})/(OD_{540\ 1\times triton}-OD_{540\ PBS}) \times 100$. Similar experiment was performed with chicken RBCs (OARDC, Ohio).

Toxicity of the selected four SMs on *Galleria mellonella* larva: *Galleria mellonella* larvae (fifth instar stage) were incubated for 12 hrs at 37° C. in the dark. After incubation, only larvae with a white phenotype and a body weight ranging between 225 mg to 275 mg were selected for the injection. Fifteen larvae per group were inoculated in one of the last pro-leg with 12.5 µg of SMs (8.5 µl) using a PB600-1 repeating dispenser (Hamilton, Reno, NV) attached to 300 µl insulin syringe, 31-gauge, 8 mm needle length (ReliOn®, Bentonville, AR). SMs were diluted into a buffer mix (30% DMSO plus 10 mM $MgSO_4$). Larvae were placed inside a plastic petri dish and incubated for 3 days in the dark at 37° C. Every 12 hrs of interval, the larva survival was monitored. Non-treated larvae, larvae treated with the buffer mix, and larvae treated with 12.5 µg of chloramphenicol were used as control. At least two independent experiments were conducted.

Effect of the four SMs on *S. typhimurium* intracellular survival in cells lines: The ability of four SMs to clear *S. typhimurium* WT in vivo was evaluated using three cell lines (Caco-2 cells, HD11, and THP-1 cells). The *Salmonella* intracellular survival as assessed as described (13). A multiplicity of infection "MOI" of 10 was used. Infected cells were treated with 1 µl of SMs (final concentration ranged between 100 µM and 6.25 µM) at 37° C. for 24 hrs in humidified, 5% $CO_2$ incubator. Following incubation, cells were washed once with 150 µl of 1×PBS, lysed with 0.1% Triton-100X, serial ten-fold diluted in 1×PBS, and plated on agar plate. Plates were incubated at 37° C. for 24 hrs to determine the intracellular survival. Cells not infected and not treated, and cells infected and treated with 2% DMSO were used as controls.

Effect of the selected four SMs on *S. typhimurium* intracellular survival in *G. mellonella* larvae: Wax moths were selected as mentioned previously in the toxicity assay section. First, the virulence of both $Kan^R$ and WT *S. typhimurium* strains in *G. mellonella* was assessed. Briefly, a *S. typhimurium* suspension normalized at approximately $10^6$ CFU/ml in 10 mM $MgSO_4$ was used as the inoculum. Larvae were infected with 8.5 µl of inoculum (approximately $3.5 \times 10^4$ bacteria per larva) and incubated for three days in the dark at 37° C. in a plastic petri dish. Survival rate was monitored every 12 hrs. The bacterial quantification was performed once the larvae were considered dead (dark pigmentation or no reaction to a mechanical stimulus) or after the 72 hrs of incubation. Larvae were washed once with 70% ethanol, twice with sterile distilled water for 30 sec each, and transferred individually into an Eppendorf® tubes containing 1 ml of 1×PBS to be homogenized. The mixture was serial diluted, plated on XLT-4 agar plate supplemented with 50 µg/ml kanamycin, and incubated for 36 hrs at 37° C. Larvae not treated and larvae treated with the buffer mix were included as controls. At the end of the experiment, mortality rate and internalized *Salmonella* population were compared between the two *S. typhimurium* strains. Once it was confirmed that the virulence of both $Kan^R$ and WT *S. typhimurium* strains were identical in *G. mellonella* larvae, the clearance abilities of the four SM was performed as described above. SM and *S. typhimurium* were injected into two different pro-legs and at different time points as described (14). First, the larvae were treated with a SM, then incubated for 2 hrs at 37° C. in a plastic petri dish, and infected with approximately $3.5 \times 10^4$ of $Kan^R$ *S. typhimurium* bacteria per larva. Summary of treatments are described in Table 2.

TABLE 2

Wax moth treatments.

| Groups | Doses | S. Typhimurium injection* |
|---|---|---|
| SM1 | 12.5 µg | Yes |
| SM3 | 12.5 µg | Yes |
| SM4 | 12.5 µg | Yes |
| SM5 | 12.5 µg | Yes |
| CK | 12.5 µg chloramphenicol | Yes |
| Negative control | DMSO | Yes |
| DMSO control | DMSO | No |
| Larva control | None | No |

CK: chloramphenicol.

Effect of selected SMs on the survival of S. typhimurium in one-week-old SFP chickens: One-week-old Salmonella-free chickens were orally inoculated with approximately $10^4$ $Kan^R$ S. typhimurium bacteria. A rectal swab was collected to confirm the intestinal colonization by Salmonella at one day post-inoculation (DPI). At 3 DPI, chickens were treated orally twice a day for five days with a specific treatment of approximately 920 µg/kg SMs per dose. Details of the treatment groups are described in Table 7. Feeders were taken off one hour before the treatment and put back one hour after the treatment. Following the five days of treatment, chickens were euthanized and tissues were aseptically collected (ceca, liver, and spleen). One of the cecum was immediately stored at −80° C. after sampling for microbiota studies. Ceca, spleens, and livers tissues were suspended in 2, 3, and 5 mL of 1×PBS respectively and grinded. 1 mL of the undiluted homogenized tissue mix was enriched in 9 mL of tetrathionate broth (TTB) medium for 18 hrs at 37° C. The rest of the homogenized tissues were serial ten-fold diluted, plated on XLT4 agar plate supplemented with 50 µg/ml kanamycin, and incubated for 36 hrs at 37° C. Bacterial counts were compared with the DMSO control group.

DNA extraction and sequencing: Microbiota diversity and abundance were investigated using the second cecum directly stored in −80° C. Genomic DNA was extracted using the PureLink Microbiome DNA Purification Kit (Life Technologies, Invitrogen Corp.), combined with RNAse treatment (10 units/hour). About 0.15 g to 0.20 g of cecum content was processed according to manufacturer's instructions. After quality control with electrophoresis and nanodrop, extracted DNA samples were subjected for 16S rRNA V4-V5 variable region sequencing. As a first step of targeted sequencing, amplicon libraries were prepared by using Phusion® High-Fidelity PCR Kit (New England Biolabs Inc, Ipswich, MA) in a 96-well plate. 25 µL of PCR reactions were prepared using 5 µl (5×) of PCR buffer, 4 µl (5 ng/µl) of DNA sample, and 2.5 µl (2 µM) primer, 0.5 µl (10 mM) dNTPs, 0.2 µl of enzyme, and nuclease free water to final volume. The barcoded primers targeted the V4-V5 variable region. The following PCR conditions were used for amplifications: initial denaturation was at 96° C. for 2 min, and 25 cycles of 96° C. for 30 sec, 55° C. for 30 sec, 72° C. for 30 sec, with final extension of 72° C. for 5 min. Following PCR amplification, PCR products were cleaned using AMPure XP PCR (Beckman Coulter Inc, Beverly MA). Sample concentrations were measured, and equal concentration of all samples were pooled into one flow cell and sequenced using Illumina MiSeq 300-base, paired-end kit at the Molecular and Cellular Imaging Center (Ohio Agricultural Research & Development Center, Wooster, OH).

Bioinformatics analyses: After sequencing, a quality control of the raw reads was performed using FastQC (Babraham Bioinformatics, Cambridge, USA). Only nucleotides with a base sequence quality having a median quality score above 25 and lower quartile median quality score above 10 were used for further analysis. Trimmomatic was used for trimming and removal of NexteraPE-PE adapter sequences (15). Details concerning the parameters used are described in mcbl.readthedocs.io/en/latest/mcbl-tutorials-AD-clean.html. The resulting forward and reverse sequences were merged using Pandaseq (github.com/neufeld/pandaseq). During this step, any sequences with less than 0.7 threshold overlap was removed and primers used for amplification were trimmed. Controls containing only water and the extractions buffers used for the DNA extraction steps were analysis to confirm lack of contaminants. Then samples were processed using Quantitative Insights Into Microbial Ecology (QIIME) software version 1.9 (16). Operational Taxonomy Units (OTUs) were determined by clustering reads against Greengenes 16S reference dataset (2013-08 release) at a 97% identity using open picking reference OTU (pick_open_reference_otus.py) method using default parameters, except setting minimum OTU size to 10. Microbial diversity was studied after rarefication of the sequences based on the lowest number of sequences among the samples tested. Alpha and beta diversities were analyzed using the core analysis package (core_diveristy_analyses.py), which included the comparison of the phylogenetic diversity and richness, principal coordinate analysis, and relative abundance studies (summarize_taxa_through_plots.py). Identification of microbial difference between different diets was performed using linear discriminant analysis (LDA) in the Galaxy/Hutlab website (huttenhower.sph.harvard.edu/galaxy/).

Chemical structure analysis of the small molecules (SMs): The physic-chemical properties of each SM were obtained through Chembridge©; San Diego, CA. Structural analysis of the SMs was performed using PubChem Compounds (National Center for Biotechnology Information; Rockville Pike, MD) and ChemMine website (Backman et al., 2011; Bolton et al., 2008). SMs were clustered based on their structural similarities. A tanimoto score was calculated from a two-dimensional (2D) structure fingerprint using a single linkage algorithm.

Statistical analysis: All in vitro experiments other than the primary screening and the chicken experiment were performed twice with at least three biological duplicates. Growth curves and bacterial counts were compared by one-way ANOVA, followed by Student T test using JMP PRO 12 software (Cary, NC 27513). Statistical analysis for G. mellonella survival rates was performed in GraphPad Prism 5 software (GraphPad, Inc., CA, USA) using the Kaplan-Meier estimator. Microbiota data were analyzed in the Galaxy|Hutlab interface using a Kruskall-Wallis test combined with a pairwise Wilcoxon test and JMP PRO 12 software. For each statistical analysis, a p-value ≤0.01 was considered as significant.

Results

A large-scale HTS of 4182 small molecules (SMs) was performed at 200 µM against S. typhimurium WT in a 96-well plate format in order to identify growth inhibitors. A total of 128 SMs inhibited S. typhimurium WT growth between 20% to 100% when Salmonella was grown in minimal nutrient condition for 12 hrs (FIG. 1A).

Figure 1B:
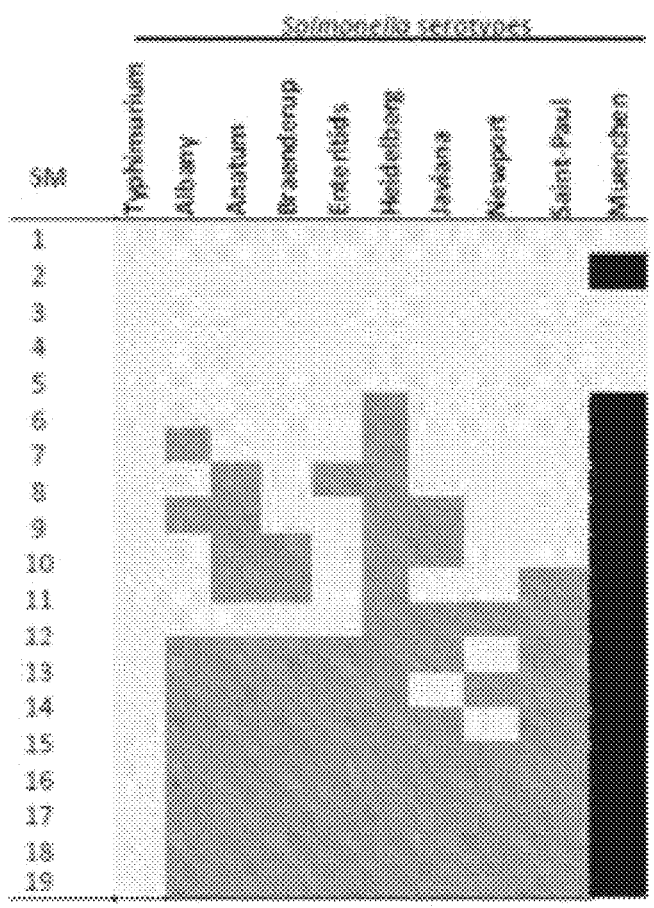
FIG. 1B: Activity of 19 *S. typhimurium* growth inhibitors against additional *Salmonella* serotypes. Light grey cells: total growth inhibition; dark grey cells: bacterial growth observed; black cells: not determined.
Figure 1C:
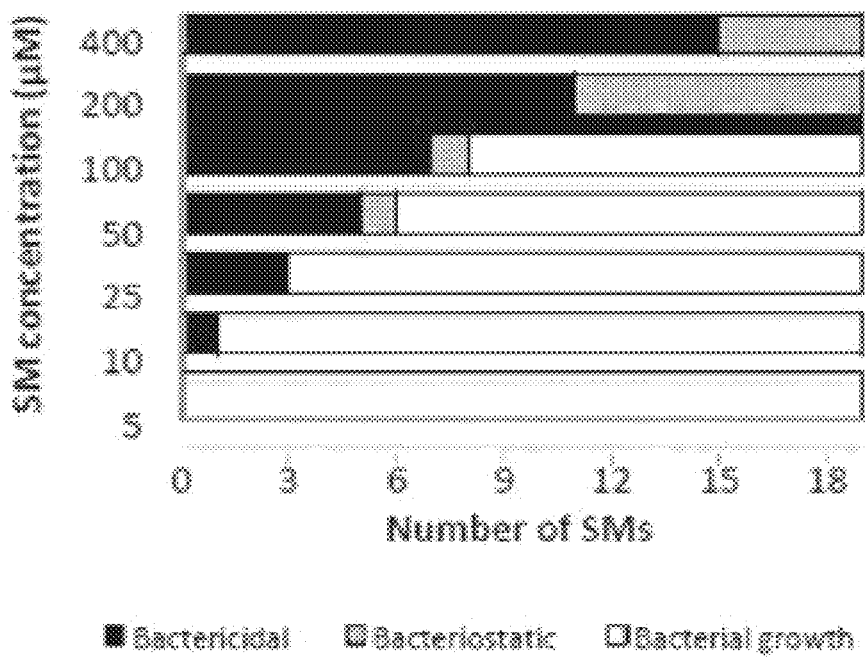
FIG. 1C: Dose-response assays of the selected 19 SMs against *S. typhimurium* WT.
Figure 1D:
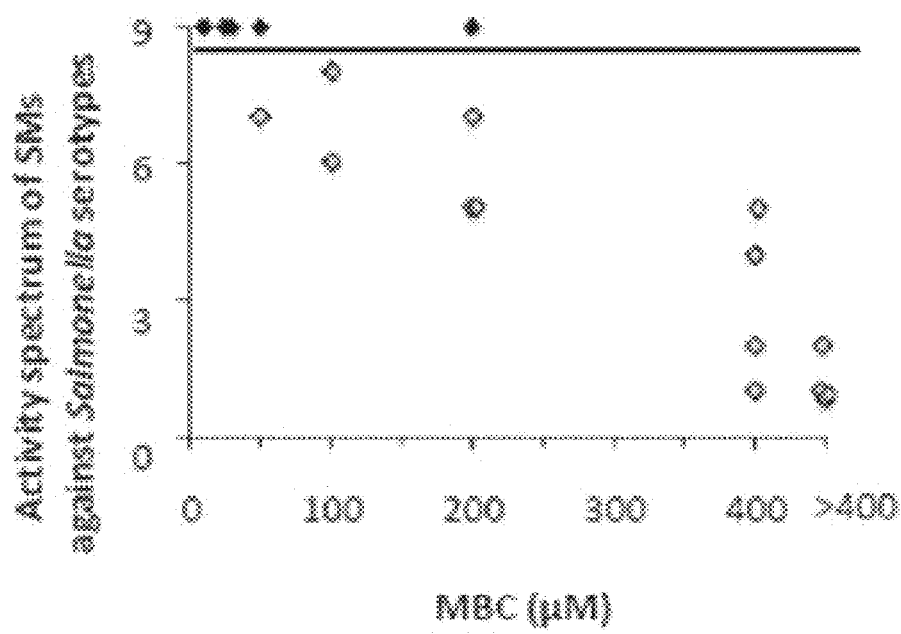
FIG. 1D: Plot of the selected 19 SMs based on their minimal bactericidal concentration (MBC) and spectrum of activity against several *Salmonella* serotypes at 200 μM. The black line represents a cut off of nine serotypes killed per SM.

Five small molecules (SMs) were bactericidal to diverse Salmonella serotypes: The spectrum of activity was evaluated with the 128 SMs against nine additional Salmonella serotypes, with the top 19 performers shown in FIG. 1B. Chemical details of the 19 SMs are listed in Table 3. *S. typhimurium* WT and S. Newport were the two serotypes with the highest number of SMs that completely inhibited the bacterial growth at 200 µM (n=19 and 18, respectively), while S. Anatum and S. Heidelberg had the lowest amount (n=8 SMs for both). Among the 19 SMs that completely inhibited *S. typhimurium* WT growth, bactericidal SMs had a broader spectrum of activity than the bacteriostatic SMs. Five SMs (SM1 to SM5) had a cidal effect against the nine *Salmonella* serotypes tested. Further, the dose-response assay performed with these 19 SMs identified fifteen bactericidal SMs against *S. typhimurium* WT at a concentration between 400 µM to 10 µM, and four SMs were bacteriostatic at 400 µM (FIG. 1C). The comparison of antimicrobial specificity and efficacy revealed that the five SMs active against all *Salmonella* serotypes (SM1 to SM5) possessed the lowest minimal bactericidal concentrations (MBCs) among the 19 SMs (FIG. 1D; the five black diamonds located above the black line).

TABLE 3

Chemical information of selected 19 SMs.

| Compound number | ChemBridge | Chemical name | Chemical class | Effect on S. Typhimurium at 200 µM |
|---|---|---|---|---|
| 1 | 5217485 | 1,3-bis{2-[(2-isopropyl-5-methylcyclohexyl)oxy]-2-oxoethyl}-1H-3,1-benzimidazol-3-ium chloride | Imidazole | Bactericidal |
| 2 | 5236864 | 1-(3,6-dibromo-9H-carbazol-9-yl)-3-{(2-hydroxyethyl)(methyl)amino]-2-propanol | Carbazole | Bactericidal |
| 3 | 5472505 | 1-(cayanomethyl)-3-hexadecyl-1H-imidazol-3-ium chloride | Imidazole | Bactericidal |
| 4 | 5476471 | 1-hexadecyl-3-methyl-1H-3,1-benzimidazol-3-ium bromide | Imidazole | Bactericidal |
| 5 | 6149508 | N''-{4-[(4-chlorobenzyl)oxy]-3-ethoxybenzylidene} carbonohydrazonic diamide | Methoxybenzyl-amine | Bactericidal |
| 6 | 74494968 | 1-[benzyl(methyl)amino]-3-[-4-({[(5-chloro-2-thienyl)methyl]amino}methyl)phenoxy]-2-propanonol | Methoxybenzyl-amine | Bactericidal |
| 7 | 5375237 | 2,4-dichloro-6-{[(2-fluoro-5-nitrophenyl)imino]methyl}phenol | Benzamide | Bactericidal |
| 8 | 5375470 | 2,4-dichloro-6-{[(3-methoxyphenyl)imino]methyl}phenol | Phenyl-imino-methyl-phenol derivatives | Bactericidal |
| 9 | 48965560 | N-[1-(4-isobutylbenzyl)-3-piperidinyl]-2-(4-methyl-1,4-diazepan-1-yl)acetamide | Piperidine | Bactericidal |
| 10 | 5149535 | ethyl 5-acetyl-2-amino-4-methyl-3-thiophencerboxylate | Thiophene | Bacteriostatic |
| 11 | 5142944 | 4-[1-(3-methoxpenyl)cyclopentyl]phenol | Cyclopentyl-phenol | Bacteriostatic |
| 12 | 5511895 | 3-[3-(4-bromophenyl)-2-triazen-1-yl]-5-nitrobenzoic acid | Benzamide | Bacteriostatic |
| 13 | 5453817 | 1-benzyl-N-[2-{2,4-dichlorophenyl)ethyl]-4-piperidinamine | Piperidine | Bacteriostatic |
| 14 | 5102124 | Not produced anymore by ChemBridge | Unknown | Bacteriostatic |
| 15 | 81977255 | 1-(1-azocanyl)-3-(2-methoxy-5-{[(4-methylbenzyl)amino]methyl}phenoxy)-2-propanol | Methoxybenzyl-amine | Bacteriostatic |
| 16 | 5375462 | 4-bromo-2-{[(3-methoxyphenyl)imino[methyl]phenol | Phenyl-imino-methyl-phenol derivatives | Bacteriostatic |
| 17 | 5809863 | 1-methyl-5-[(5-nitro-2-furyl)methylene]-2,4,6(1H,3H,5H)-pyrimidinetrione | Pyrimidine | Bacteriostatic |
| 18 | 5133155 | 4-benzoyl-5-methyl-2-phenyl-2,4-dihydro-3H-pyrazol-3-one | Imidazole | Bacteriostatic |
| 19 | 5237087 | 1-(9H-fluoren-9-yl)-4-(3-phenyl-2-propen-1-yl)piperazine | Piperazine | Bacteriostatic |

Only the five SMs active against all *Salmonella* serotypes (SM1 to SM5) were selected for further dose-response studies against other serotypes. Results are displayed in Table 4. Minimal inhibitory concentrations (MICs) were identical to minimal bactericidal concentrations MBCs for a given serotype and thus, the values reported in Table 4 can be considered either a MIC value or a MBC value; however, some variations in MIC and MBC were observed between serotypes and between SMs.

TABLE 4

Dose-response of SMs 1-5.

| Salmonella serotypes | MIC/MBC (µM) | | | | |
|---|---|---|---|---|---|
| | SM1 | SM2 | SM3 | SM4 | SM5 |
| Typhimurium | 50 | 100 | 25 | 10 | 25 |
| Albany | 100 | 200 | 25 | 10 | 100 |
| Anatum | 100 | 200 | 25 | 10 | 50 |
| Braenderup | 100 | 200 | 25 | 10 | 50 |
| Enteritidis | 100 | 200 | 25 | 10 | 50 |
| Heidelberg | 100 | 200 | 50 | 25 | 50 |
| Javiana | 100 | 200 | 25 | 10 | 50 |
| Newport | 100 | 200 | 50 | 25 | 50 |
| Saint-Paul | 100 | 200 | 50 | 10 | 50 |
| Muenchen | 100 | ND | 50 | 25 | 50 |

ND: not determined.

*S. typhimurium* WT developed resistance mechanisms against SM2 following a single exposure at a lethal dose (2×MIC) in solid medium and also a repeated exposure at sub-lethal dose (0.75×MIC) in liquid medium for 15 passages at 37° C. Resistant bacteria were able to grow in a minimal growth condition with 400 µM of SMs, which represent 4×MBC; however, these bacteria displayed similar sensitivity to the other four SMs, suggesting that SM2 probably has a different target in *Salmonella* than the other four SMs. SM2 was not selected for further study.

Antimicrobial efficacy of the four SMs was also tested on biofilm-protected *Salmonella* using the MBEC™-HTP assay. After 18 hrs incubation with SMs having concentrations ranging from 0.2×MBC to 4×MBC, SM1 and SM5 displayed similar antimicrobial efficacy whether *S. typhimurium* WT was protected or not by a biofilm. However, SM4 and SM5 had enhanced clearance efficacy by killing *Salmonella* even at 0.6×MBC and 0.4×MBC, respectively. These results could to be explained by the structural composition of both SMs, discussed further below.

Figure 1E:
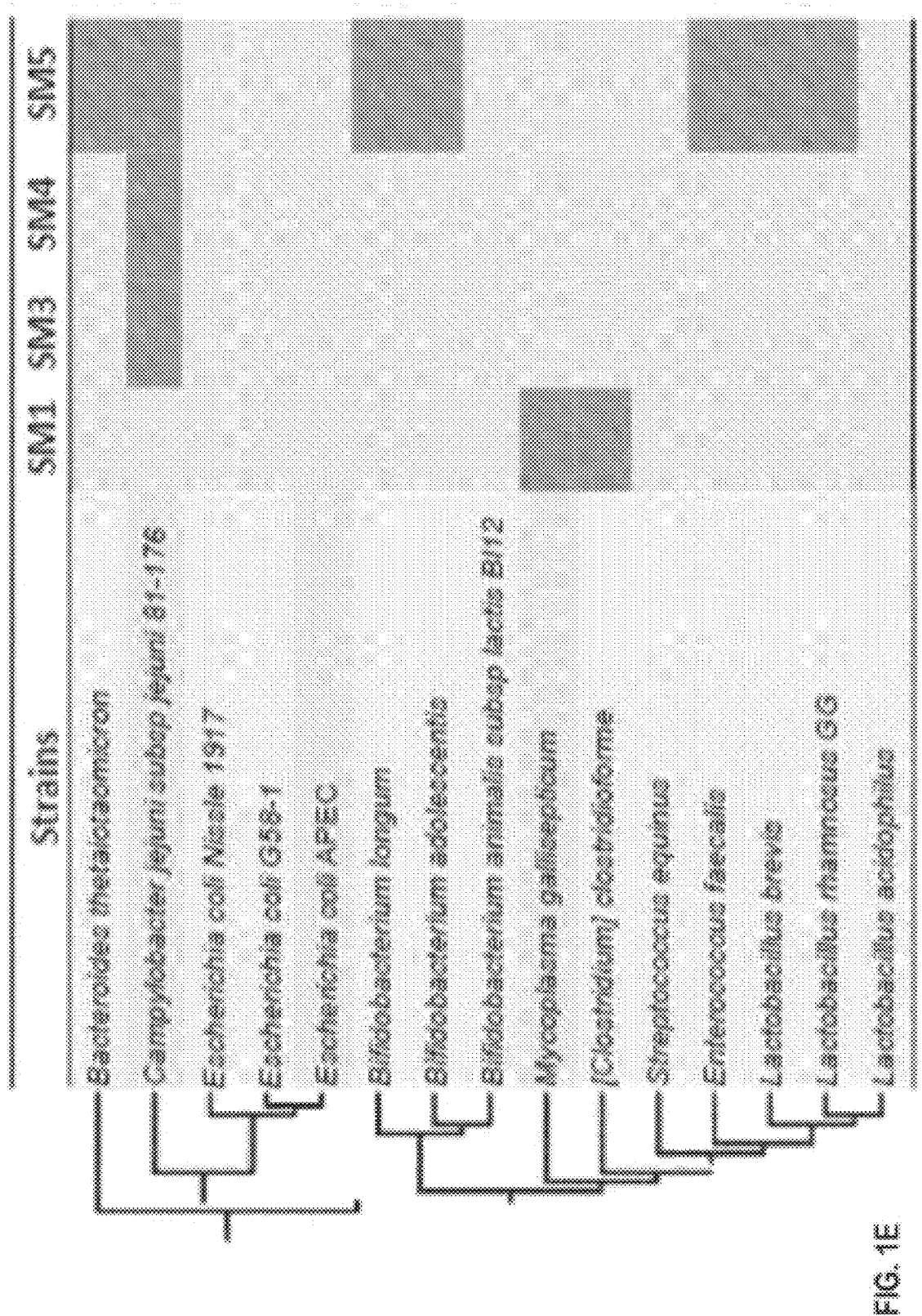
FIG. 1E: Activity spectra of the selected four SMs at 200 μM each on several avian-pathogens (*Campylobacter jejuni, Escherichia coli* APEC, and *Mycoplasma gallisepticum*) and beneficial gut bacteria (remaining species). *E. coli* APEC refers to Avian Pathogenic *E. coli* and includes *E. coli* O1, O2, O8, O15, O18, O35, O78, O109, and O115. Light grey cells: cidal effect; dark grey cells: bacterial growth observed. Left side: phylogenetic tree based on NCBI taxonomic ID built with PhyloT software.

The selected four SMs were tested on twelve beneficial-commensal gut bacteria at 200 µM (FIG. 1E). SM3 and SM4 had a broad spectrum of activity by killing all twelve strains tested; while SM1 had no growth inhibition effect on *C. clostridioforme* and SM5 had no effect on *B. thetaiolaomicron, B. adolescentis, B. longum, E. faecalis, L. brevis*, and *L. rhamnosus* GG at 200 µM. These four SMs were also growth inhibitors of other avian pathogens at 200 µM (unpublished data, FIG. 1E). SM1 had bactericidal effects against *C. jejuni* 81-176; SM3 and SM4 were lethal to several Avian Pathogenic *E. coli* (O1, O2, O8, O15, O18, O35, O78, O109, and O115); and *M. gallisepticum* was killed by SM3, SM4, and SM5. The antimicrobial activity seemed not to be influenced by the taxonomic classification, however the SM5 bacterial target may be less present in prokaryotes than the drug target of the other three SMs.

Figure 2A:
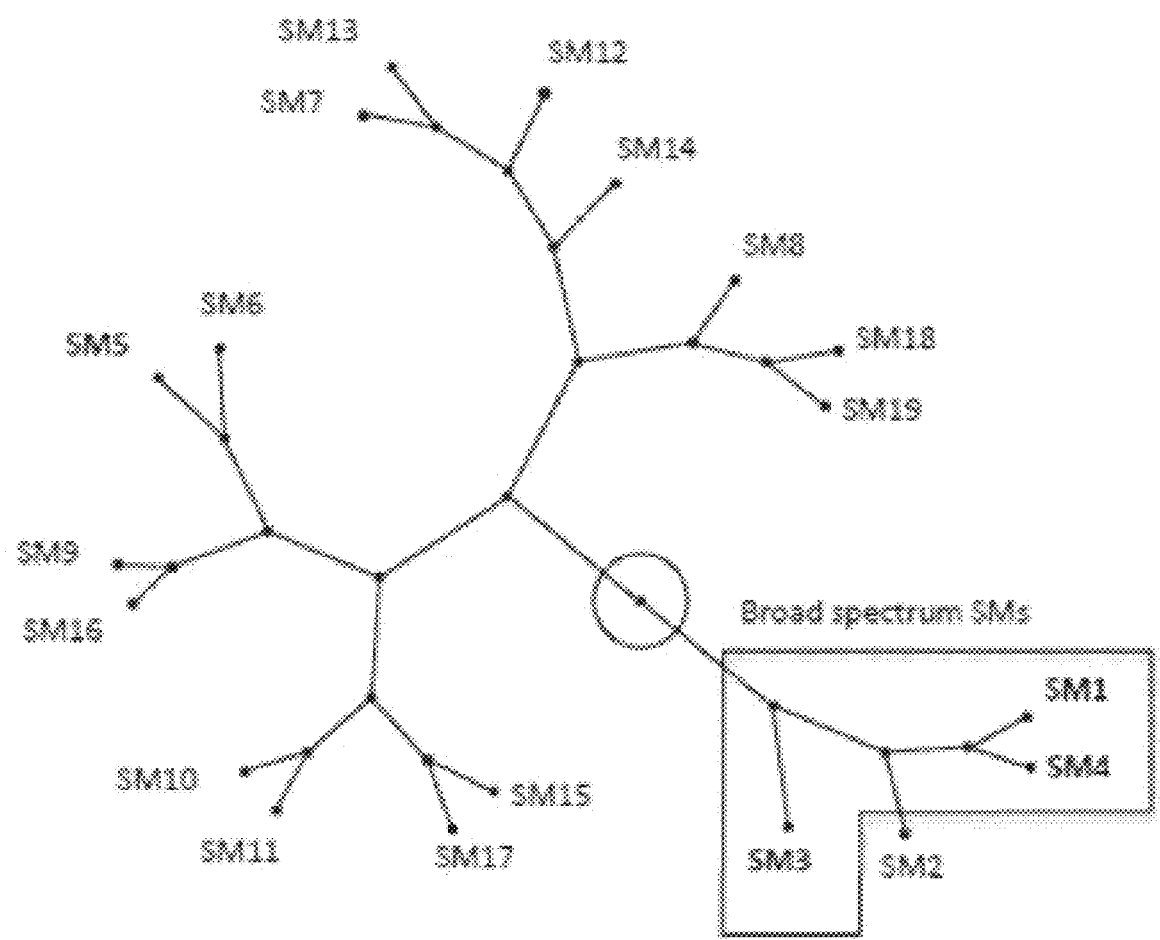
FIG. 2A: Constellation plot of the selected 19 SMs based on their 2D structural similarities. In bold: SMs effective against nine *Salmonella* serotypes. Framed SMs: SMs with a broad antimicrobial activity spectrum against most of the bacteria tested. The circle is the root of the tree. SMs were clustered based on their chemical group. Serial number: PubChem ID.
Figure 2B:
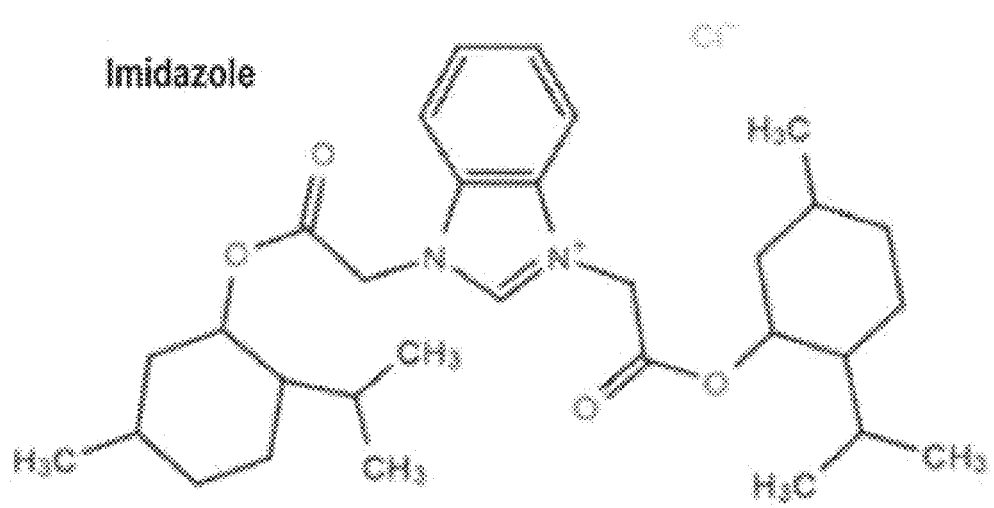
FIG. 2B: Chemical structure of SM1.
Figure 2C:
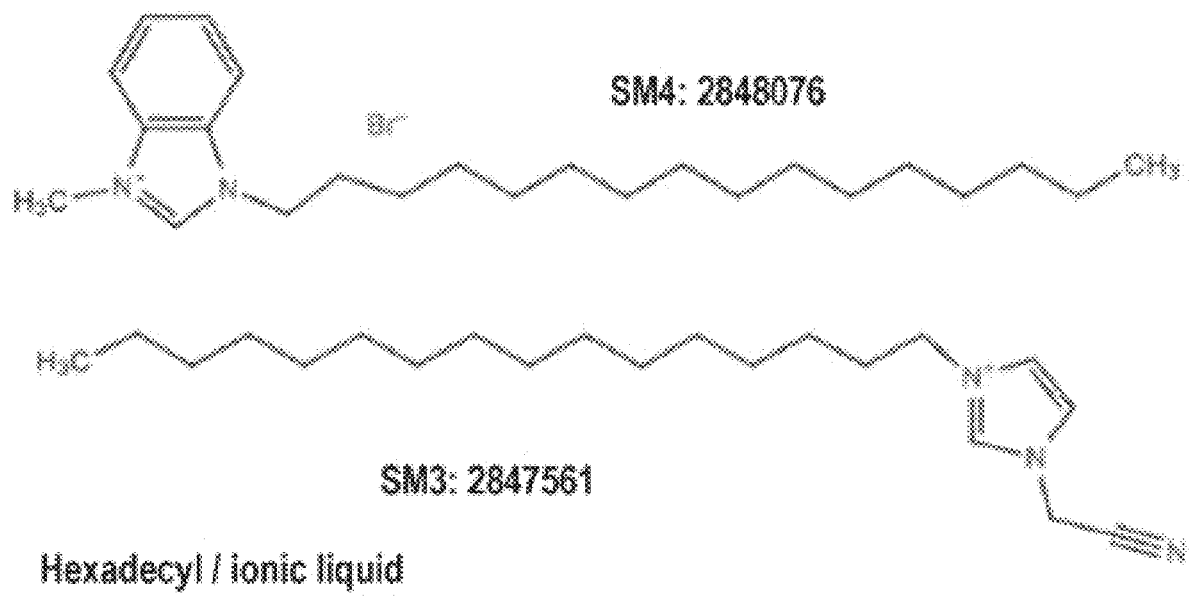
FIG. 2C: Chemical structure of SM3 and SM4.
Figure 2D:
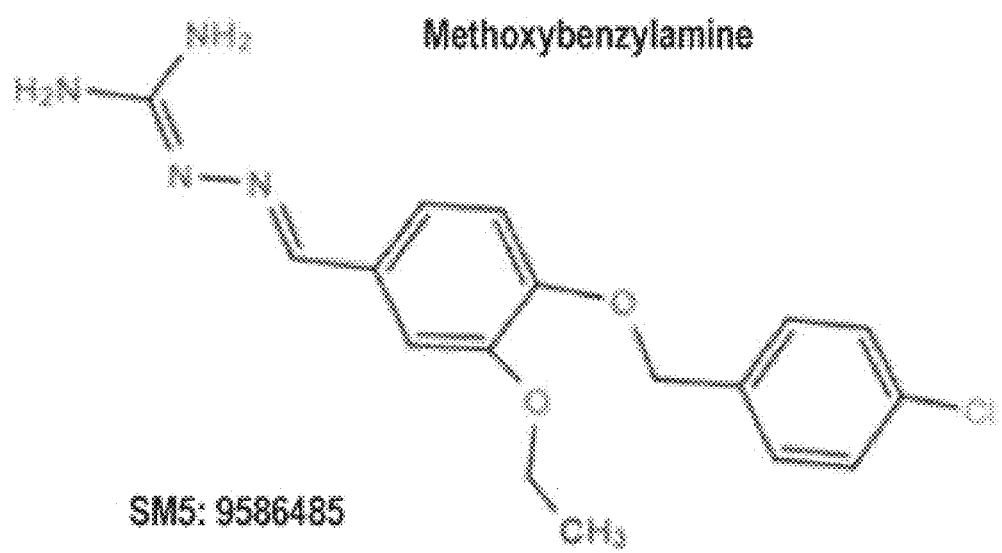
FIG. 2D: Chemical structure of SM5.
Figure 2E:
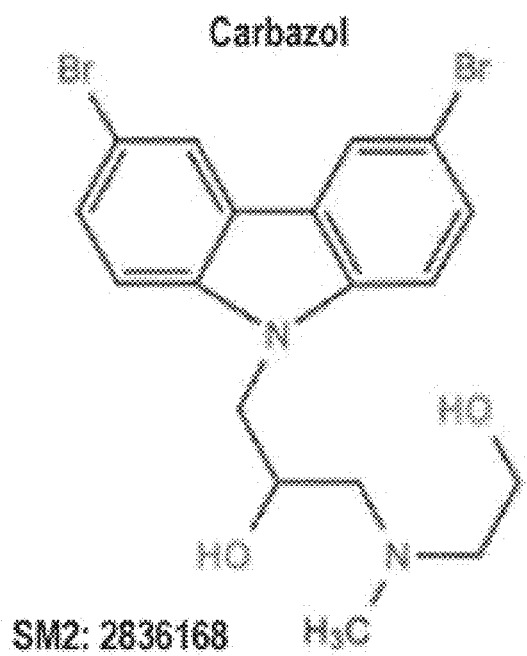
FIG. 2E: Chemical structure of SM2.

Structure-activity relationship (SAR) analysis: Structural analysis of the 19 SMs inhibiting completely *S. typhimurium* WT growth separated the SMs into 3 clusters based on a 2D Tanimoto score (n=4, 8, and 7) (FIG. 2A). The two bigger groups had a homogenous distribution of the SMs bacteriostatic and bactericidal SMs; however, the small group was composed only of the broad spectrum SMs (SM1, SM2, SM3, SM4) and SM5 was in the group of 8 SMs. The results suggested that SM2, SM3, and SM4 have a common 2D structure that seems to explain the scope of their antimicrobial activity. The structure of SM1 included an imidazole (FIG. 2B), the structure of SM3 and SM4 included a hexadecyl/ionic liquid (FIG. 2C), and the structure of SM5 included a methoxybenzylamine (FIG. 2D).

Figure 13:
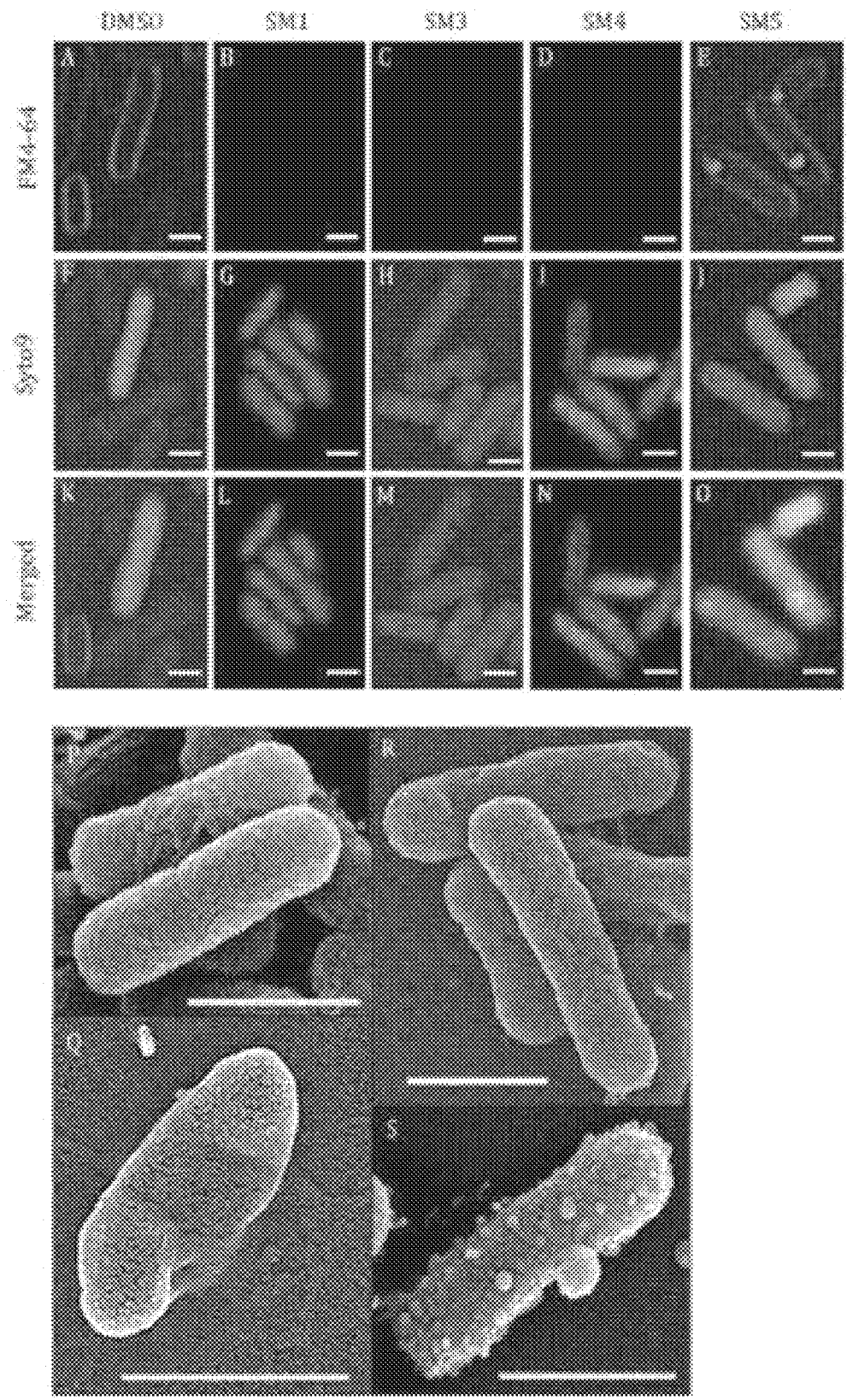
FIG. 13. Confocal and scanning electron microscopy (SEM) analyses of *Salmonella enterica* subsp. *Enterica* serotype *Typhimurium* after challenge with five times the minimal bactericidal concentration of small molecules (5×MBC of SMs) for 3 hrs. (A-O) Confocal microscopy: (A-E) *S. typhimurium* cell membrane stained with FM4-64; (F-J) *S. typhimurium* nucleic acids stained with SYTO9; (K-O) Merged pictures of the FM4-64 and SYTO9 staining. (P-S) SEM: (P) 1% dimethyl sulfoxide (DMSO) treated *Salmonella*; (Q) SM1 treated *Salmonella*; (R) SM4 treated *Salmonella*; (S) SM5 treated *Salmonella*; Bar: 1 μm.

SMs exhibited antimicrobial activity by affecting cell membrane integrity of *S. typhimurium*: Confocal microscopy analysis of *S. typhimurium* challenged individually with a lethal dose of each of the four SMs revealed an alteration of the membrane phenotype when stained with FM4-64 compared to the 2% DMSO treated control (FIG. 13). No signal was detected from the FM4-64 staining when bacteria were treated with SM1, SM3, and SM4 (FIG. 13B-D) compared to the DMSO control (FIG. 13A). On the other hand, bacteria treated with SM5 displayed a stained cell membrane; however, a bright red spot was detected within every bacterium (FIG. 13E). No distinct modification of the phenotype was observed in bacteria treated with any of the four SMs after staining with the nucleic acid stain SYTO9 (FIG. 13G-J) compared to the DMSO control (FIG. 13F).

To further support the observation obtained with confocal microscopy, the same samples were analyzed using scanning electron microscopy (SEM; FIG. 13P-S). SM1-, SM4-, and SM5-treated cells displayed significant alterations of the cell surface (FIGS. 13Q,R and S, respectively) compared to the 2% DMSO control (FIG. 13P) consistent with the confocal microscopy results (FIG. 13B-E). Further, the FM4-64 stained red spots observed with SM5-treated cells in confocal microscopy (FIG. 13E) appear to be outer membrane vesicles of approximately 100 to 300 nm diameter (FIG. 13S). Smaller outer membrane vesicles of approximately 20 to 70 nm were also observed covering the surface of the bacteria. SM1-treated cells were distorted (FIG. 13Q), while 1% DMSO-treated cells were cylindrical with no deformation (FIG. 13P), suggesting that SM1 might also weaken and disrupt the cell wall conformation of *S. typhimurium* in addition to disrupting the cell membrane. The cell surface of SM4-treated bacteria looked roughened and crumpled (FIG. 13R). No SEM analysis was performed with SM3 due to limitation in compound availability; however, given that SM3 and SM4 have very similar chemical structures, SM3 is likely to possess a phenotype similar to that of SM4. These observations strongly suggest that the SMs alter *Salmonella* cell membrane and cell wall integrity. These conclusions were further supported by measuring the crystal violet uptake and leakage of materials assessed at 260 nm after 1 hr of treatment with a lethal dose of SMs. SM5-treated cells had an increase in permeability (2.32-fold) accompanied by a more abundant quantity of 260 nm-absorbing material (5.25-fold) compared to the 1% DMSO-treated cells. These results were very similar to those for cells treated with 0.25 M of ethylenediaminetetraacetic acid (EDTA), supporting the effect on *S. typhimurium* cell membrane by SM5. However, SM1-, SM3-, and SM4-treated cells displayed an increase in 260 nm-absorbing material (2.18, 7.17, and 15.95-fold, respectively) compared to the 1% DMSO control, and showed a reduction of crystal violet uptake (1.88, 4.46, and 2.01-fold, respectively) in the treated cells compared to the 1% DMSO control. These results might be explained by the disruption of cell membranes by SM1, SM3, and SM4, as observed by confocal microscopy (FIG. 13B-D), allowing less material to be stained by crystal violet.

Figure 3A:
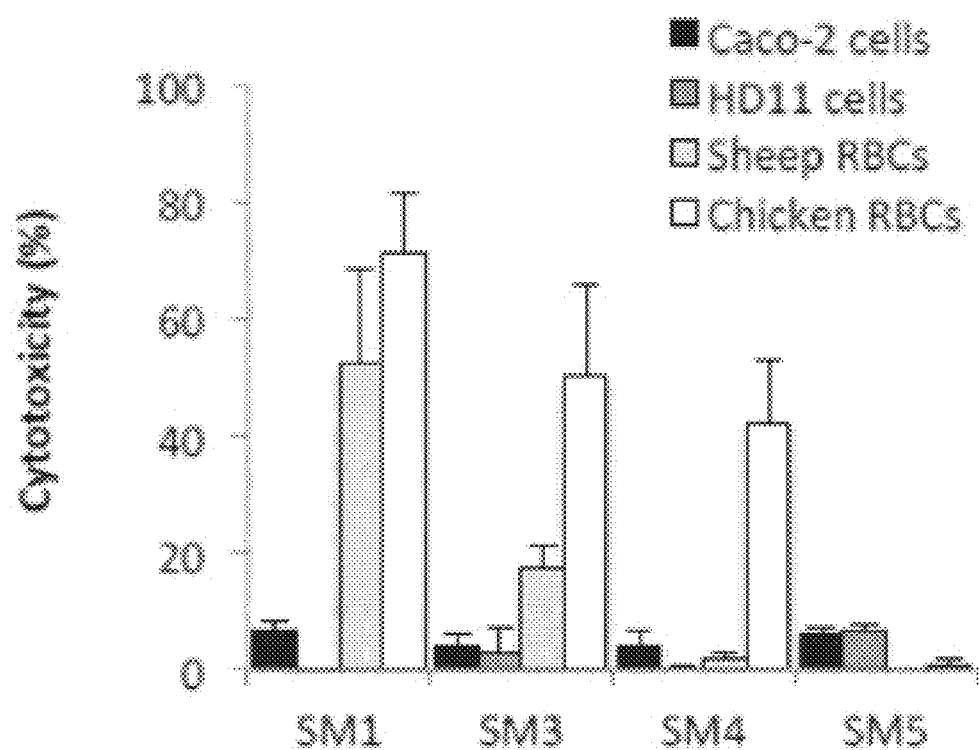
FIG. 3A: Toxicity of the selected four SMs on Caco-2 cells and HD11 cells 24 hours post-treatment with 200 μM SMs, and toxicity (hemolytic activity) on red blood cells (chicken and sheep RBCs) 2 hours post-treatment with 200 μM SMs. Data were normalized with a 0.1% triton-100× control. Bar: standard deviation; N=8.

Synergetic effect of SMs 1 and 3-5 on antibiotics against *S. typhimurium*: Out of six antibiotics tested, three antibiotics (ciprofloxacin, cefepime, and Meropenem) had a synergetic or additive effect with one of the four SMs tested (Tables 5A and 5B). SM1 displayed the best results. For examples, ciprofloxacin alone had a $MBC_{alone}$ of 0.0625 µg/ml against *S. typhimurium* WT, but once combine with SM1 ciprofloxacin, $MBC_{combined}$ was reduced by 62.5-fold (0.001 μg/ml) when 40 μM of SM1 was added. Similar trends were observed with Nalidixic acid (up to 70% reduction in MBC when combined with SM1), Cefepime (up to 90% reduction in MBC when combined with SM1), and Meropenem (up to 80% reduction in MBC when combined with SM1). The presence of SM had no effect on Erythromycin and Cefotaxime MBCs.

toxicity levels were below 10% in Caco-2 human epithelial cells and below 18% with HD11 chicken macrophage cells for the four SMs (FIG. 3A). After one-hour treatments on sheep and chicken red blood cells (RBCs) with 200 μM of SMs, SM5 displayed a hemolytic activity lower than 1% for both RBCs; while SM3 and SM4 had a hemolytic activity

TABLE 5A

Antimicrobial synergy data

| ATB | $MBC_{Alone}$ | [SM1] | $MBC_{Comb1}$ | [SM3] | $MBC_{Comb3}$ | [SM4] | $MBC_{Comb4}$ | [SM5] | $MBC_{Comb5}$ |
|---|---|---|---|---|---|---|---|---|---|
| Cipro | 0.0625 | 40 | 0.001 | 15 | 0.004 | 7.5 | 0.004 | 20 | 0.004 |
| Cipro | 0.0625 | 20 | 0.004 | 10 | 0.006 | 10 | 0.006 | | |
| Cipro | 0.0625 | 5 | 0.006 | 5 | 0.008 | | | | |
| Erythro | 200 | 50 | 200 | 25 | 200 | 10 | 200 | 25 | 200 |
| Cefo | 3.2 | 50 | 3.2 | 25 | 3.2 | 10 | 3.2 | 25 | 3.2 |
| Nal Acid | 16 | 40 | 4.8 | 25 | 16 | 10 | 16 | 25 | 16 |
| Nal Acid | 16 | 30 | 8 | | | | | | |
| Cefepime | 2 | 20 | 0.2 | 20 | 0.4 | 10 | 0.4 | 25 | 2 |
| Cefepime | 2 | 10 | 1.2 | 15 | 0.8 | 1.25 | 1.6 | | |
| Cefepime | 2 | 5 | 1.6 | 2.5 | 1.2 | | | | |
| Mero | 0.2 | 20 | 0.04 | 20 | 0.08 | 10 | 0.2 | 25 | 0.2 |
| Mero | 0.2 | 10 | 0.08 | 15 | 0.16 | | | | |
| Mero | 0.2 | 5 | 0.16 | | | | | | |

SM numbers in brackets refer to concentration of SM (μM). $MBC_{Alone}$ refers to Minimum Bactericidal Concentration (MBC) of the antibiotic by itself (no SM). $MBC_{Combx}$ refers to the MBC of the antibiotic+SM combination, wherein X refers to the specific SM (1, 3, 4, 5). MBCs are reported in μg/mL. ATB: Antibiotic; Cipro: ciprofloxacin; cefo: cefotaxime; Erythro: erythromycin; Nal Acid: nalidixic acid; Mero: meropenem. For reference, $MBC_{Alone}$ of SM1, SM3, SM4, and SM5 (in μM) is 50, 25, 10, and 25 μM, respectively.

below 18% in sheep RBCs and below 49% in chicken RBCs; and SM1 had high activity for both RBCs (>50%) (FIG. 3A).

Figure 3B:
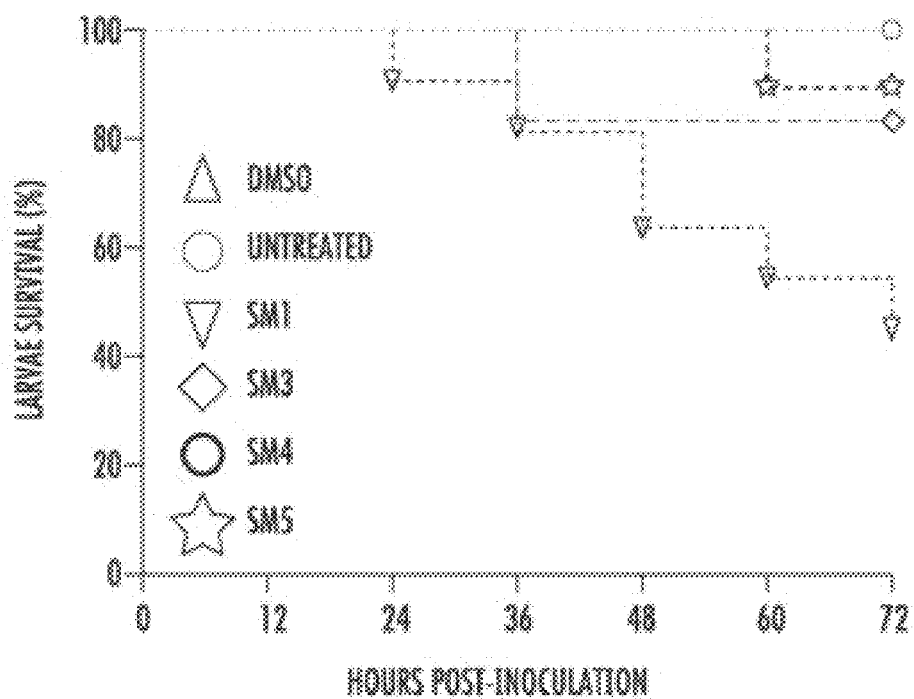
FIG. 3B: *G. mellonella* larva survival rate after single injection with 12.5 μg per larva (50 mg/kg) of the selected four SMs. Larvae were incubated at 37° C. in the dark. Survival rate was monitored every 12 hours for 72 hours.

Additional toxicity studies were performed in G. mellonella larvae model (FIG. 3B). After 72 hrs post-inoculation (HPI) following a single treatment with 12.5 μg, the larvae survival rate ranged between 100% and 64%. SM4 had no lethal effect in the larva over the 72 HPI, SM1 treatment led to a chronic death of the larvae over time, and SM3 and SM5 treatments killed only a few larvae. In conclusion, SM3,

TABLE 5B

Antimicrobial synergy results

| ATB | $MBC_{Alone}$ | [SM1] | $SM1_R$ | [SM3] | $SM3_R$ | [SM4] | $SM4_R$ | [SM5] | $SM5_R$ |
|---|---|---|---|---|---|---|---|---|---|
| Ciprofloxacin | 0.0625 | 40 | Add | 15 | Add | 7.5 | Add | 20 | Add |
| Ciprofloxacin | 0.0625 | 20 | Syn | 10 | Syn | 10 | Ind | | |
| Ciprofloxacin | 0.0625 | 5 | Syn | 5 | Syn | | | | |
| Erythromycin | 200 | 50 | Ind | 25 | Ind | 10 | Ind | 25 | Ind |
| Cefotaxime | 3.2 | 50 | Ind | 25 | Ind | 10 | Ind | 25 | Ind |
| Nalidixic Acid | 16 | 40 | Ind | 25 | Ind | 10 | Ind | 25 | Ind |
| Nalidixic Acid | 16 | 30 | Ind | | | | | | |
| Cefepime | 2 | 20 | Syn | 20 | Add | 10 | Ind | 25 | Ind |
| Cefepime | 2 | 10 | Add | 15 | Add | 1.25 | Add | | |
| Cefepime | 2 | 5 | Add | 2.5 | Add | | | | |
| Meropenem | 2 | 20 | Add | 20 | Ind | 10 | Ind | 25 | Ind |
| Meropenem | 0.2 | 10 | Add | 15 | Ind | | | | |
| Meropenem | 0.2 | 5 | Add | | | | | | |

SM numbers in brackets refer to concentration of SM (μM). $MBC_{Alone}$ refers to Minimum Bactericidal Concentration (MBC) of the antibiotic by itself (no SM). ATB: Antibiotic; $SMX_R$ refers to the results of synergy testing for each SM, wherein X refers to the specific SM (1, 3, 4, 5); Add: Additive effect of the combined Antibiotic+SM; Syn: Synergistic effect of the combined Antibiotic+SM; Ind: Indifferent effect (no combinatorial effect) of the combined Antibiotic+SM.

The four SMs possessed low toxicity on eukaryotic models: After 24 hrs of treatment with 200 μM of SMs, cytotoxicity levels were below 10% in Caco-2 human epithelial SM4, and SM5 did not show any signs of toxicity in most eukaryotic models tested.

The four SMs cleared internalized S. typhimurium in several eukaryotic models: The S. typhimurium clearance efficacy of the selected four SMs (SMs 1 and 3-5) on infected cell lines varied depending on the SMs tested and the cell line used (Table 6). SM3 and SM4 cleared internalized Salmonella at 50 μM and 25 μM respectively in the three cell lines, while SM1 and SM5 efficacy fluctuated between 12.5 μM and 100 μM depending on the cell lines tested.

TABLE 6

Dose-response of *S. Typhimurium*-infected cells treated with SMs.

| SMs | Caco-2 cells | | HD11 cells | | THP-1 cells | |
|---|---|---|---|---|---|---|
| | MBC (μm) | IC 50% (μm) | MBC (μm) | IC 50% (μm) | MBC (μm) | IC 50% (μm) |
| SM1 | 25 | 12.5 < X < 25 | 12.5 | X < 6.25 | 100 | X < 50 |
| SM3 | 50 | 12.5 < X < 25 | 50 | X < 25 | 50 | 25 < X < 50 |
| SM4 | 25 | 12.5 < X < 25 | 25 | 12.5 < X < 25 | 25 | 12.5 < X < 25 |
| SM5 | 12.5 | 6.25 < X < 12.5 | 25 | X < 12.5 | 50 | X < 25 |

Cell types are listed at the top of the table. MBC: minimum bactericidal concentration; IC 50%: Inhibitory Concentration of SM required to inhibit 50% of bacterial growth compared to untreated controls; X: concentration, as defined by column headings.

Figure 8A:
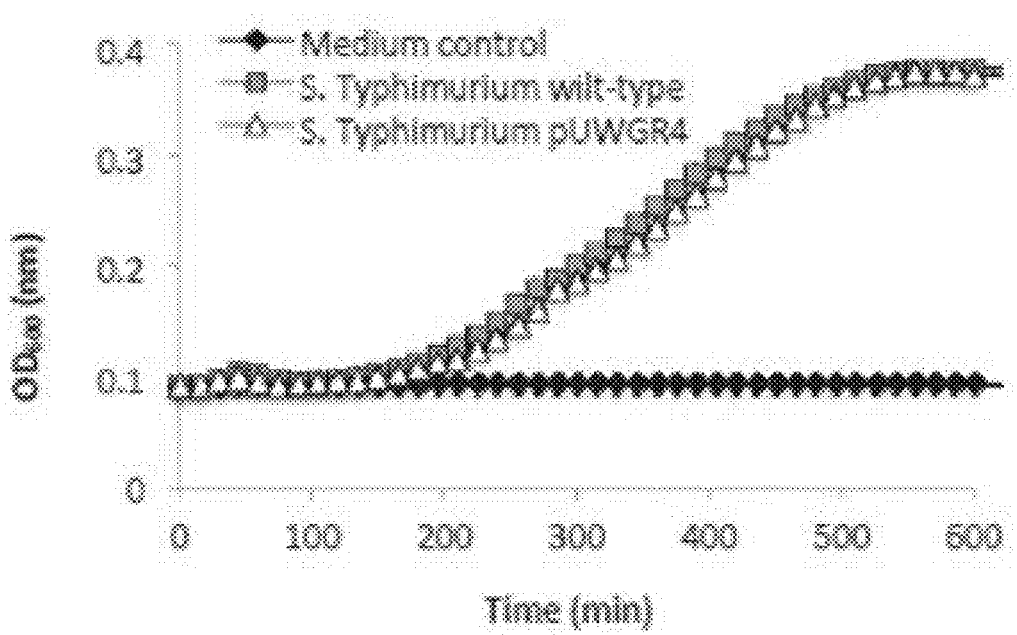
FIG. 8A: Growth curve of *S. typhimurium* strains for 12 hrs at 37° C. in a TECAN sunrise plate reader. Turbidimetric measurement was recorded every 15 min at 600 nm.
Figure 8B:
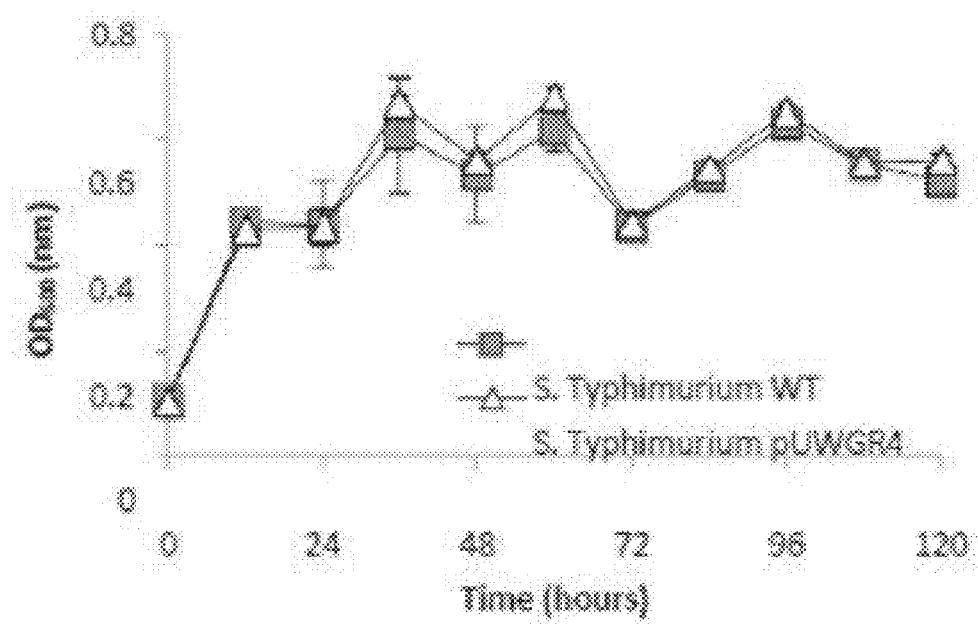
FIG. 8B: Stability test. Turbidimetric measurement at 600 nm between 12 hours passages.
Figure 8C:
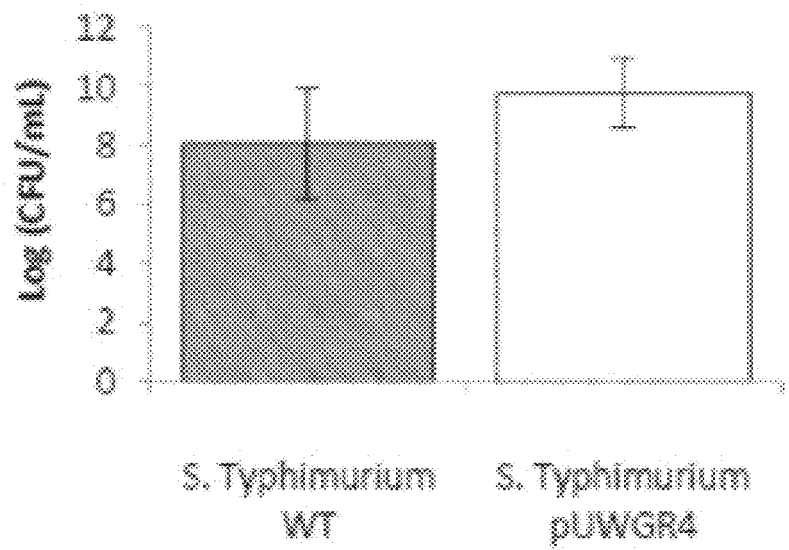
FIG. 8C: Bacterial quantification after ten passages. Statistical analyses were performed using Student T test; P>0.05. Bar: standard deviation; N=16.

The in vivo clearance efficacy of the four SMs was also tested in *Salmonella*-infected *G. mellonella* larvae. For this experiment, a *S. typhimurium* strain harboring a $Kan^R$ plasmid (hereinafter "*S. typhimurium* $Kan^R$") was used as inoculum. Preliminary data showed that *S. typhimurium* $Kan^R$ displayed similar short-term growth (FIG. 8A), stability (FIG. 8B), and long-term growth (FIG. 8C) as *S. typhimurium* WT. Further, preliminary data showed that *S. typhimurium* $Kan^R$ displayed similar bacterial quantity and larva survival profile compared to *S. typhimurium* WT when injected in *G. mellonella* (data not shown). Further, the antimicrobial efficacy of the four SMs was similar between the $Kan^R$ and WT *S. typhimurium* strains.

Figure 4A:
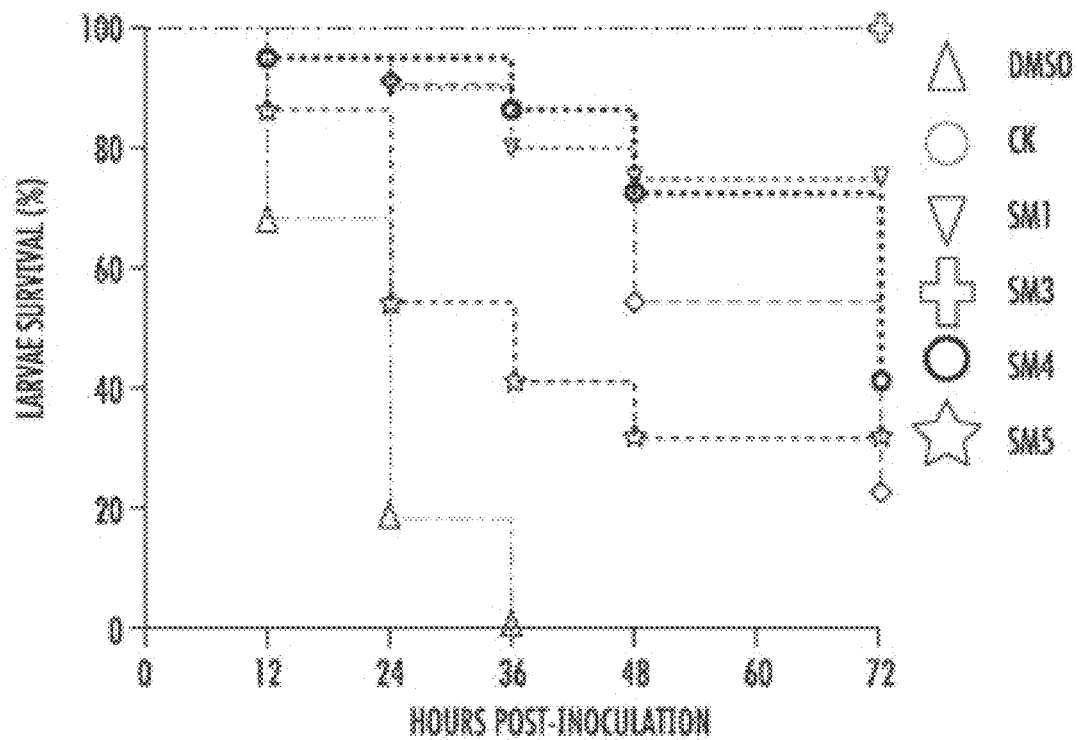
FIG. 4A: *G. mellonella* larva survival rate. Survival rate was monitored every 12 hours for 72 hrs. Infected larva treated with chloramphenicol control (CK) had 100% survival.
Figure 4B:
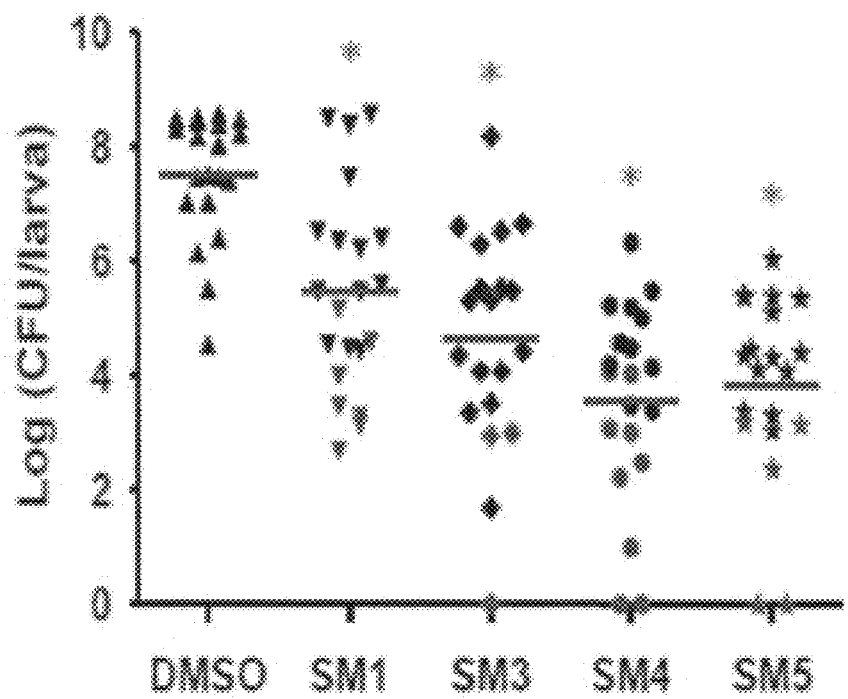
FIG. 4B: Bacterial quantification of *Salmonella* inside larvae following death of larva or, if alive, after 72 hours of incubation. Light black dot: larva still alive after 72 hrs post-inoculation (HPI); Black dot: larvae dead before 72 HPI. N=20; Black line: mean; *: internalized *Salmonella* population significantly lower in larva compared to DMSO control (P<0.01).
Figure 7:
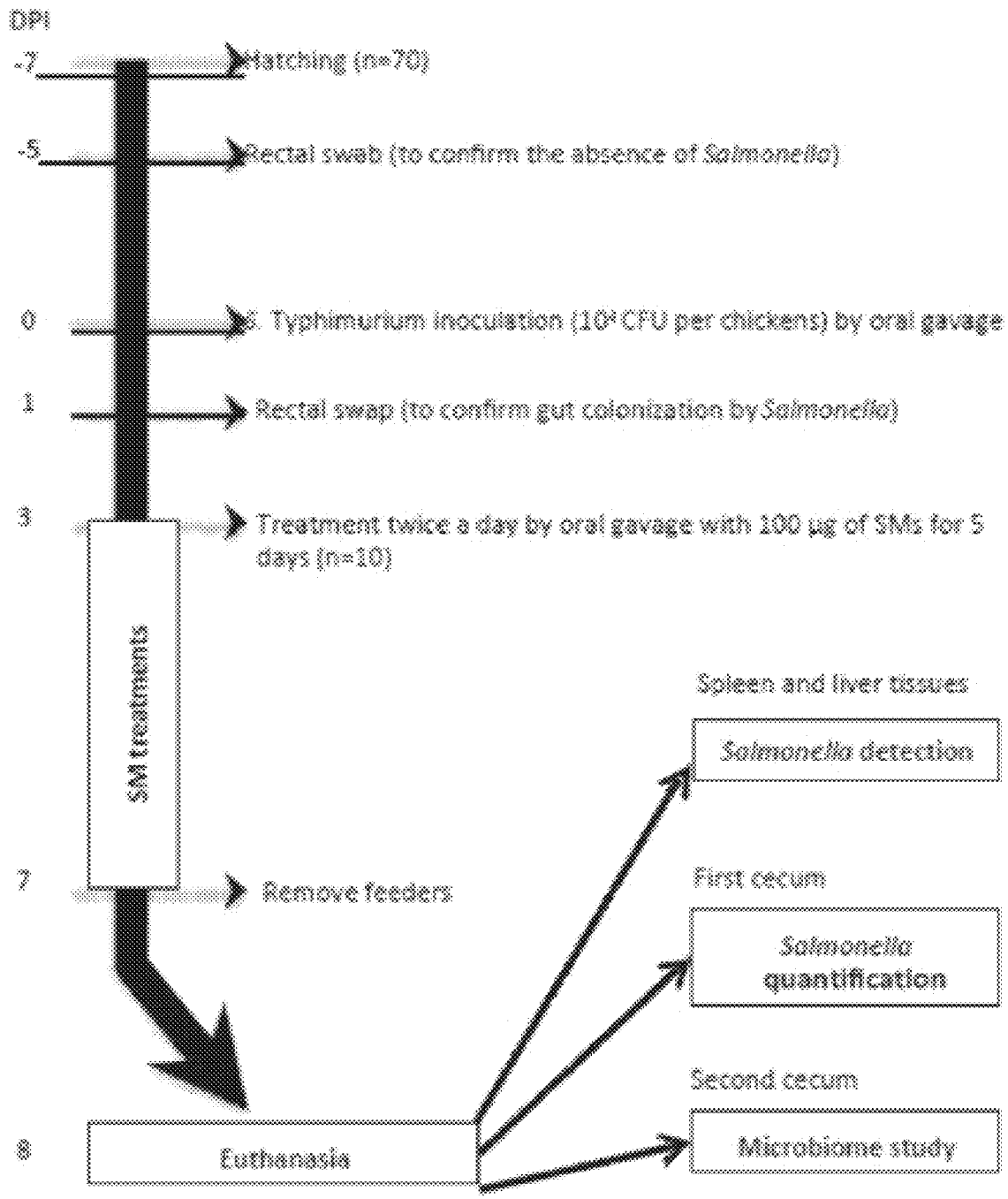
FIG. 7. Experimental design of the *Salmonella* clearance study in one-week-old infected broiler chickens. *Salmonella*-free chickens were orally infected with $10^4$ *S. typhimurium* units per chickens (0 DPI). After confirmation of the intestinal colonization by *Salmonella* (1 DPI), ten chicks per treatment were treated twice a day for five days with 100 μg of SMs (3 DPI to 7 DPI). Ceca, liver, and spleen tissues were collected at 8 DPI. DPI: days post-inoculation.

*S. typhimurium* took approximately 24 to 36 hrs to kill *G. mellonella* when larvae were infected in the pro-leg with $8.5 \times 10^4$ bacteria per larva, which was the minimal bacterial concentration needed to assure repeatable data and a slow larva death (data not shown). By consequence, these results showed only a short time window was available to study the efficacy of the SMs on *Salmonella* inside the larvae, as shown in the protocol in FIG. 7. However, the larva survival rate was significantly increased compared to the DMSO control group when the larvae were pretreated with 12.5 μg of SMs per larva 2 hrs before infection, (P<0.01) (FIG. 4A). At 24 hours post-inoculation (HPI), only 20% of the infected larva pretreated with DMSO were still alive, while larvae pretreated with the SMs showed between 55% to 95% survival. At 72 HPI, between 25% and 75% of the larvae were still alive depending on the treatment, while all larvae from the DMSO group were dead by 36 HPI. Moreover, infected larva treated with the SMs displayed a significant reduction in abundance of internalized *Salmonella* (up to 4.1-log reduction) compared to the infected untreated controls (P<0.01) (FIG. 4B). The SM treatment increased the longevity and decreased the morbidity of infected wax moth larvae.

Figure 5A:
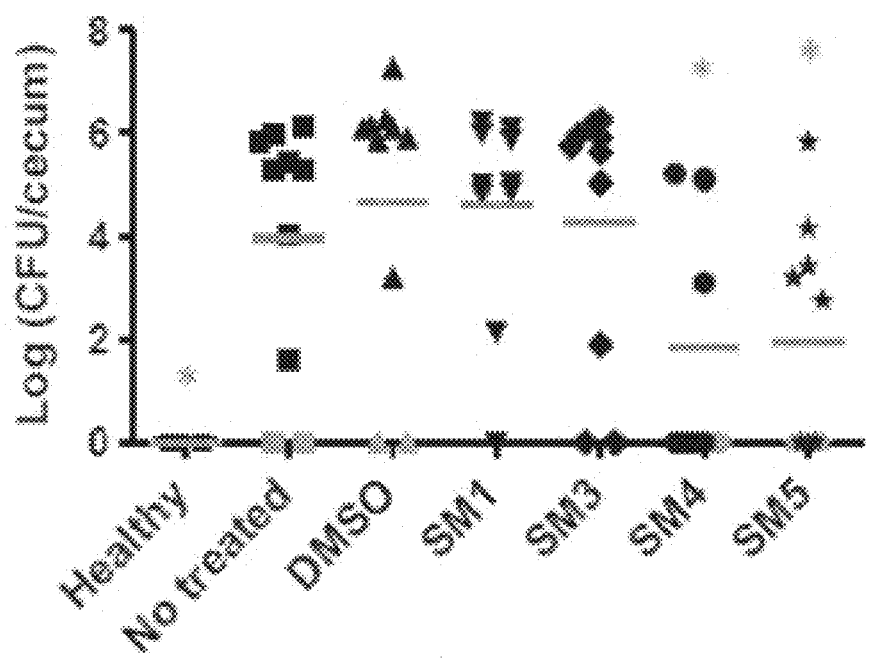
FIG. 5A: Antimicrobial efficacy of SM treatment on *Salmonella* infection in chicken ceca. Black line: average; Orange dots represent ceca samples that were detected positive for *Salmonella* after enrichment in tetrathionate broth; N=10; *: *Salmonella* population significantly lower in ceca compared to DMSO control (P<0.01).
Figure 5B:
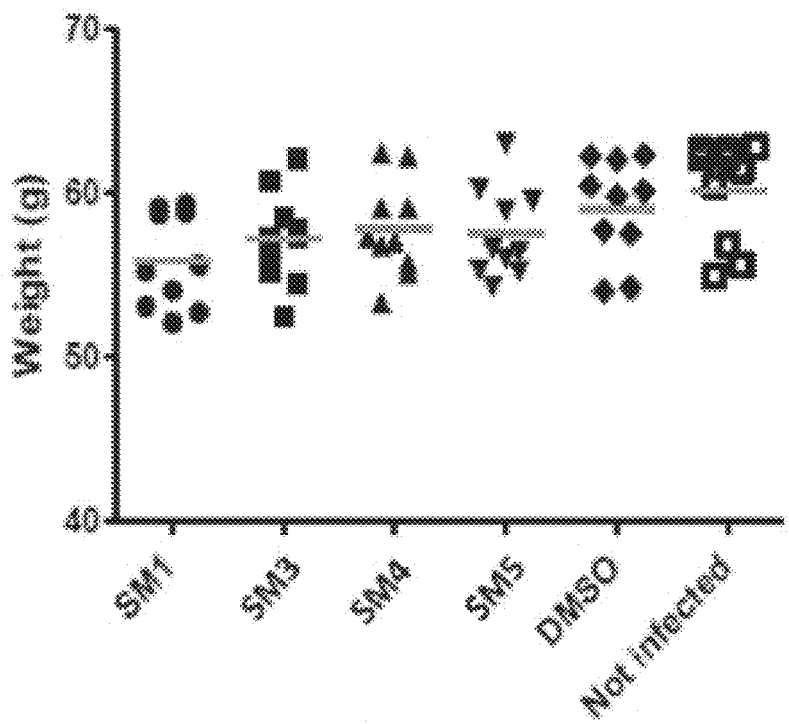
FIG. 5B: Body weight of *Salmonella*-infected chickens before SM treatments.
Figure 5C:
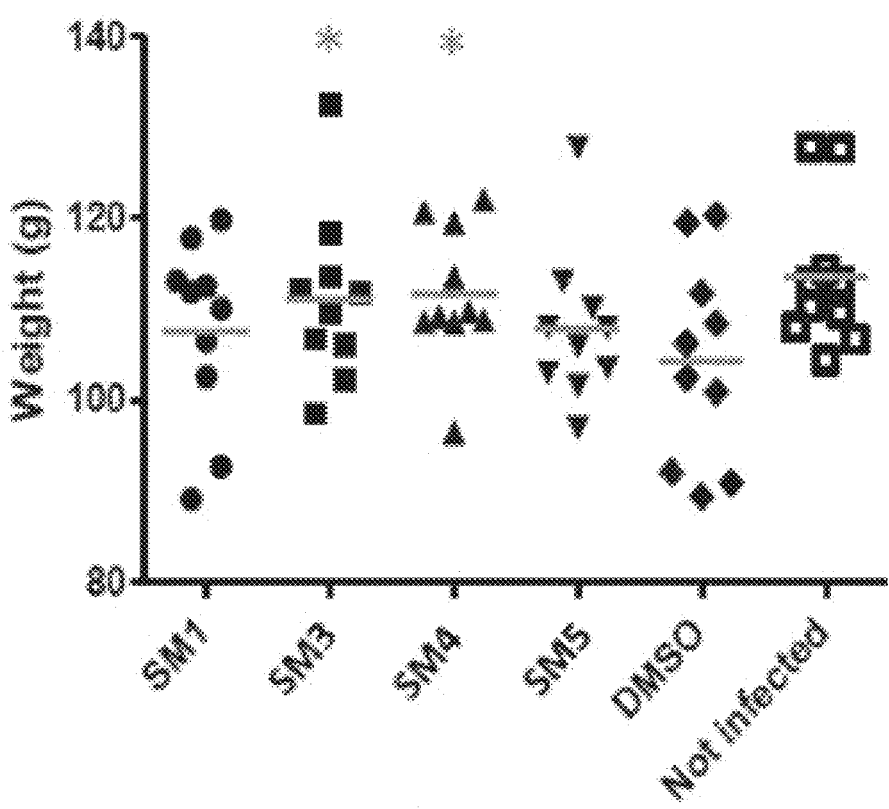
FIG. 5C: Body weight of *Salmonella*-infected chickens after SM treatments. For FIGS. 5B and 5C, *: chicken weight is significantly higher than weight of chickens treated with DMSO only (Student T test; P<0.1). Black line: mean; n=10. Weight measurements recorded before treatment were of ten-day-old chickens. Weight measurements recorded after treatment were of fourteen-day-old chickens.

SM4 and SM5 reduced *S. typhimurium* load in ceca and systemic spreading of *Salmonella* in broiler chickens: After five days of treatment with 200 μg of SMs per day according to Table 7, one-week-old infected broiler chickens treated with SM4 and SM5 displayed a 2.6-log reduction in *Salmonella* population inside the ceca (FIG. 5A) as well as a reduction in the proportion of *Salmonella*-positive tissues (Table 8) compared to DMSO group. However, chickens treated with SM1 and SM3 did not show any reduction in the cecal colonization by *Salmonella* or its systemic translocation. These results confirm that the SM4 and SM5 were effective against *Salmonella* in chicken. Further, *Salmonella*-infected chickens treated with SMs grew more in body weight compared to infected chickens treated only with DMSO control (FIGS. 5B and 5C), further demonstrating efficacy and non-toxicity of the SMs in chickens.

TABLE 7

Chicken treatment protocol (n = 10).

| Groups | Treatment | *S. Typhimurium* inoculation* | Treatment protocol |
|---|---|---|---|
| SM1 | 100 μg | Yes | Twice daily for 5 days |
| SM3 | 100 μg | Yes | Twice daily for 5 days |
| SM4 | 100 μg | Yes | Twice daily for 5 days |
| SM5 | 100 μg | Yes | Twice daily for 5 days |
| DMSO control | DMSO | Yes | Twice daily for 5 days |
| Negative control | None | Yes | No treatment |
| Positive control | None | No | No treatment |

TABLE 8

Chicken tissues positive for *Salmonella*.

| Groups | Ceca | Spleens | Livers |
|---|---|---|---|
| SM1 | 90% | 50% | 40% |
| SM3 | 80% | 50% | 60% |
| SM4 | 40% | 20% | 30% |
| SM5 | 70% | 30% | 40% |
| DMSO | 100% | 40% | 40% |

Figure 9A:
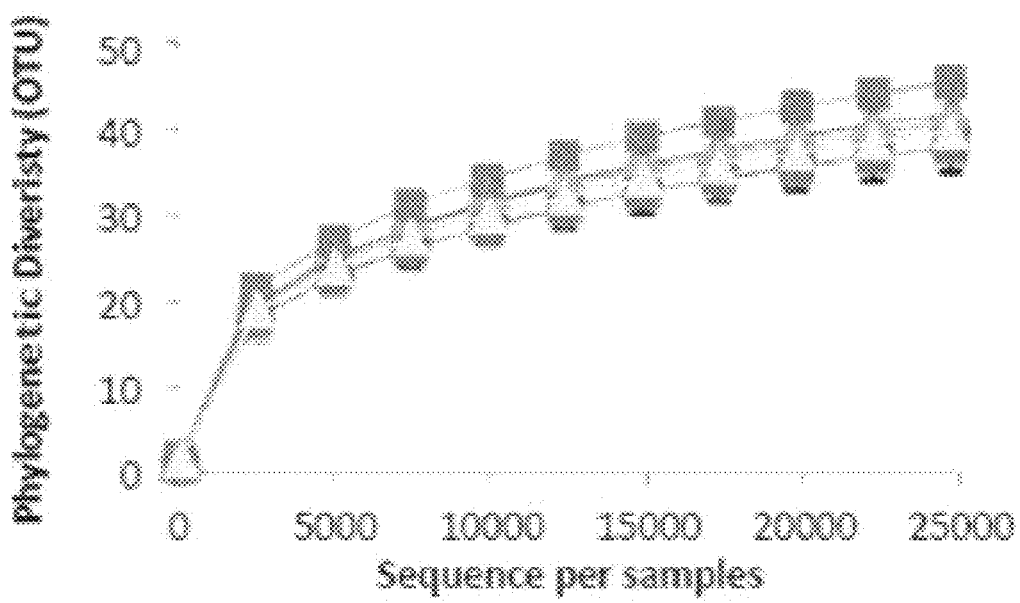
FIG. 9A: phylogenetic diversity used to measure alpha diversity.
Figure 9B:
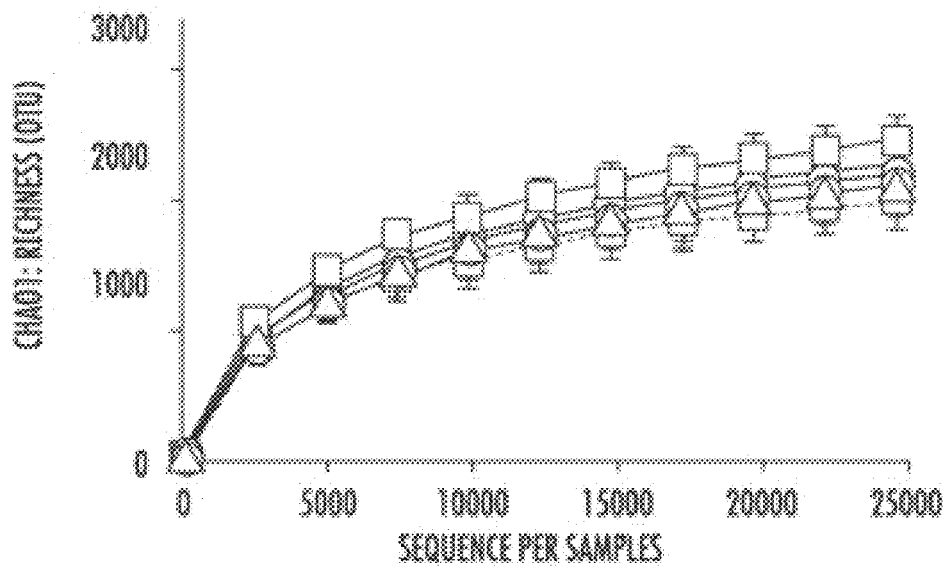
FIG. 9B: Chao1 (richness) used to measure alpha diversity. A depth of 24,700 sequences was used to study the microbiota diversity. Bar: standard deviation.
Figure 9C:
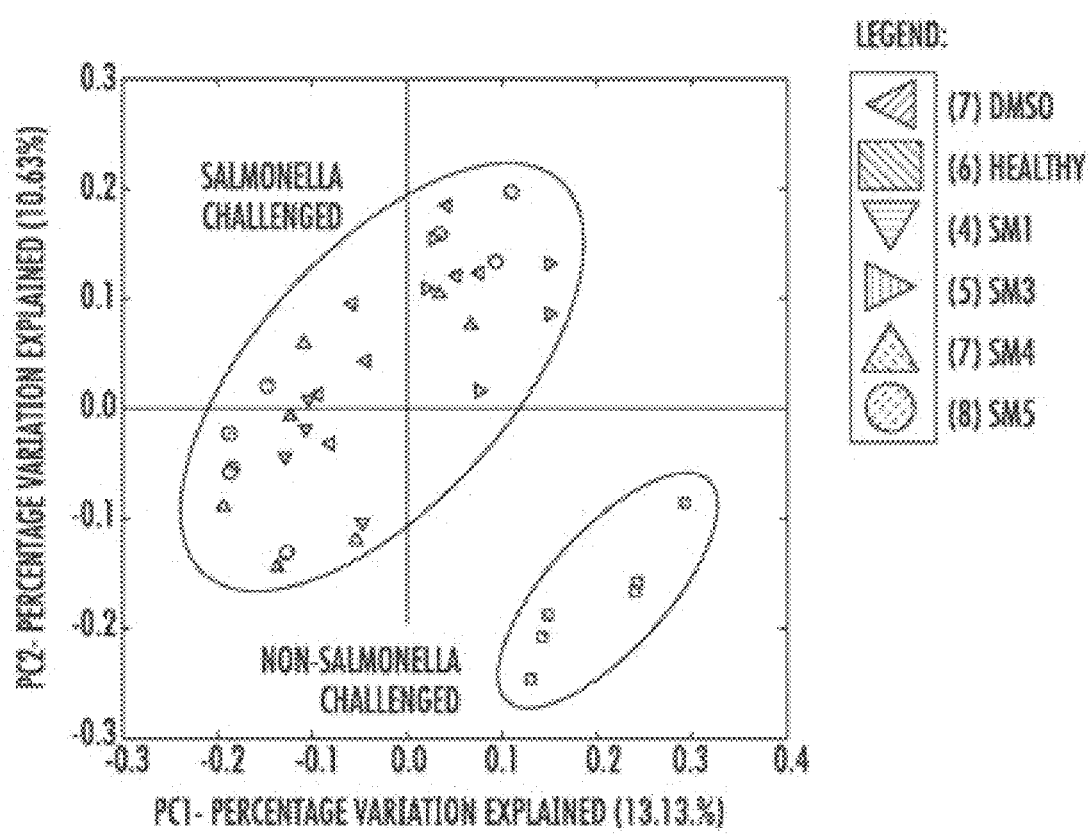
FIG. 9C: Principal coordinate analysis (PCoA) of unweighted uniFrac values. PC: principal coordinate. Each dot represents one cecum sample. The three figures share the same legend.
Figure 10A:
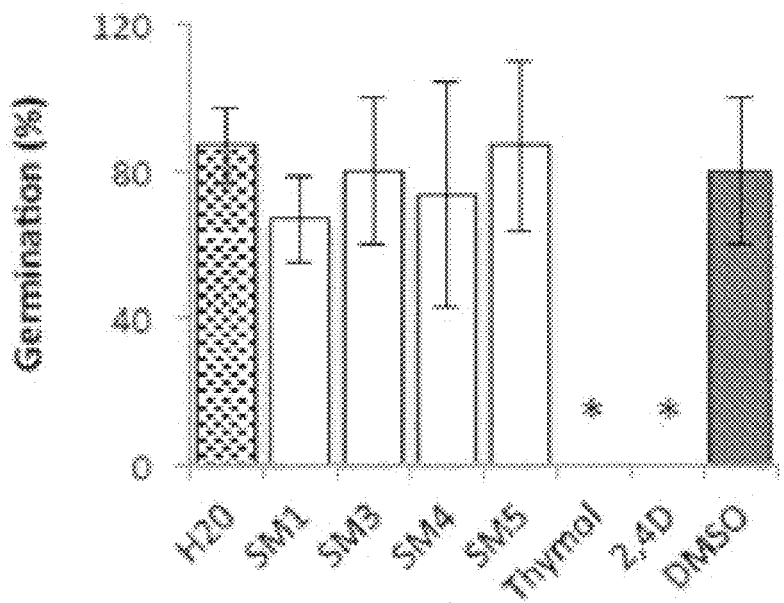
FIG. 10A: SM toxicity on tomato seed germination. Seeds were grown in water agar containing 200 μM of an SM. Bar: standard deviation. *: seed germination rate significantly lower than DMSO control (P<0.01); N=20.
Figure 10B:
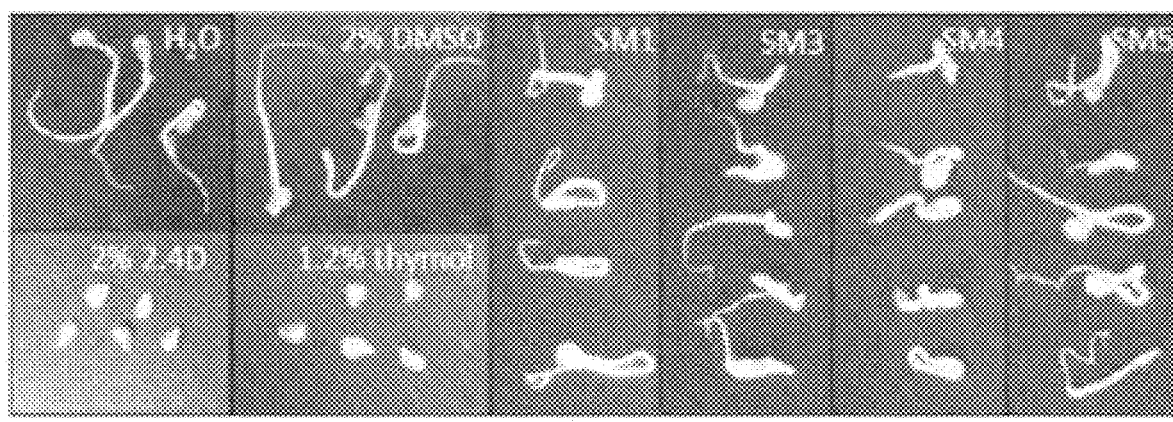
FIG. 10B: Photographs showing phenotypic aspect of tomato seeds treated with 200 μM of SMs for five days.
Figure 10C:
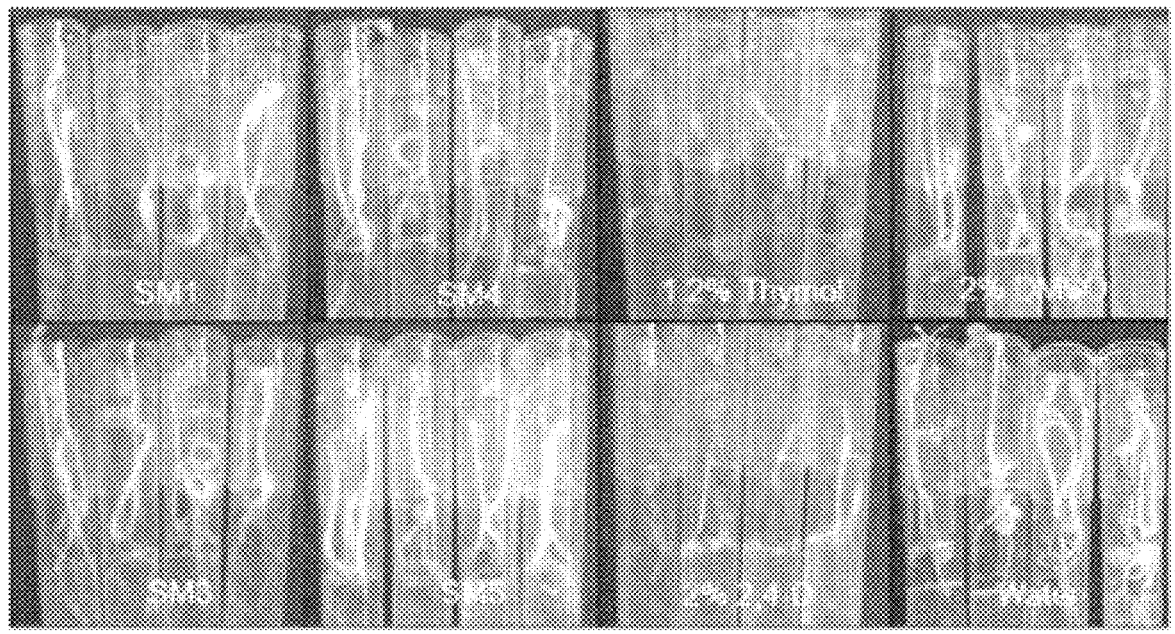
FIG. 10C: Photographs showing phenotypic aspect of ten-day-old tomato seedlings treated with 200 μM of SMs for five days.
Figure 10D:
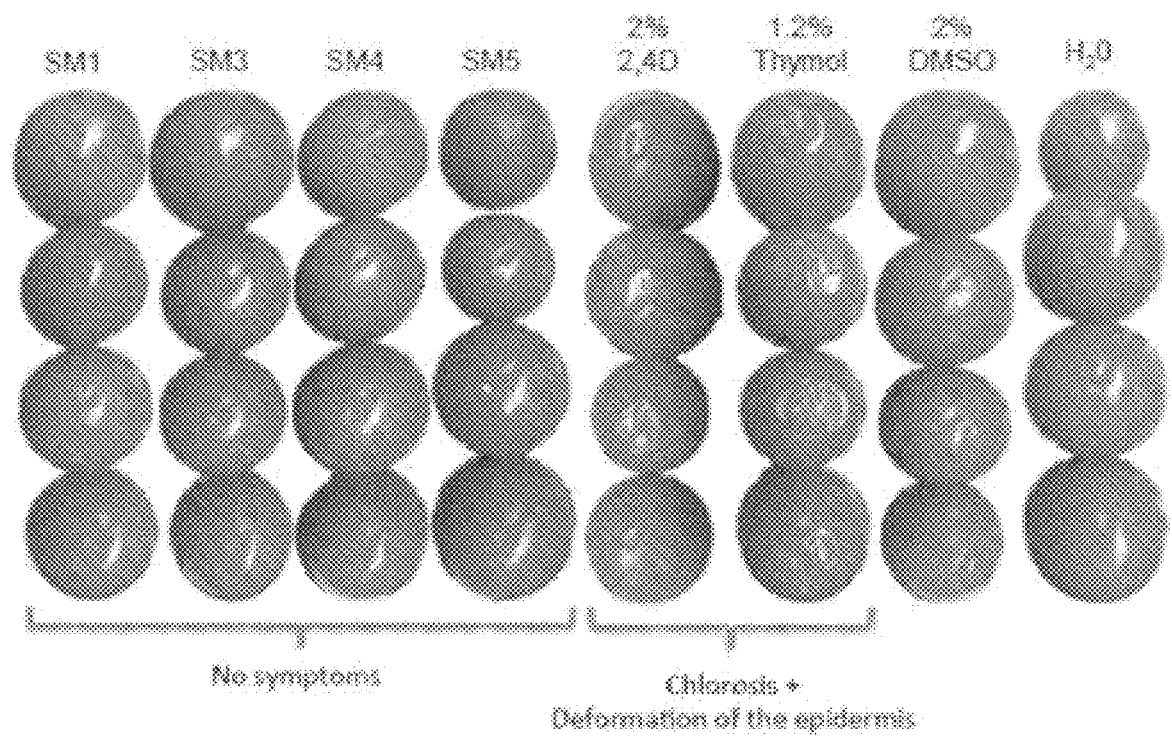
FIG. 10D: SM toxicity on ripened tomato fruits. The herbicides 2,4-D (2,4-Dichlorophenoxyacetic acid) and Thymol were used as controls.
Figure 11A:
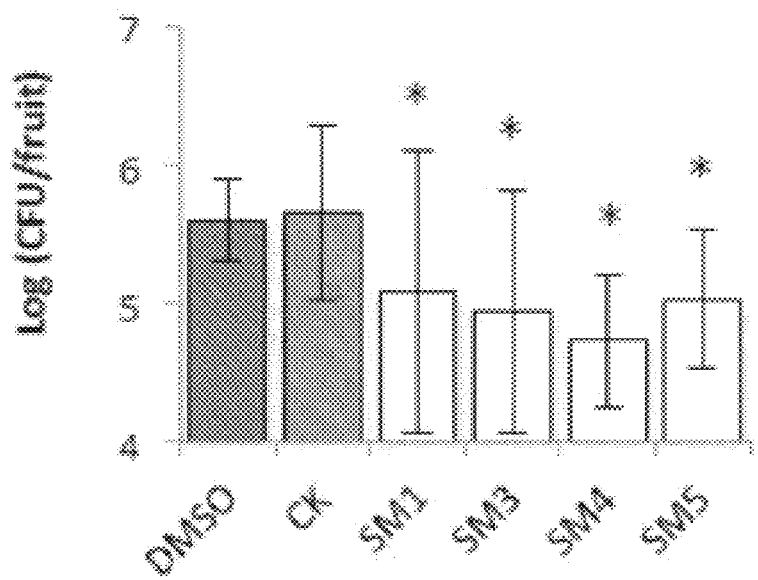
FIGS. 11(A-D). Persistence of wild-type *S. typhimurium* in tomato fruits after SM preventive or curative treatment. *Salmonella* abundance in GM (FIG. 11A) and RP (FIG. 11B) following preventive treatment with 2×MBC of SMs (SM1=100 μM; SM3=50 μM; SM4=20 μM; SM5=50 μM). *Salmonella* abundance in GM (FIG. 11C) and RP (FIG. 11D) following curative treatment with 2×MBC SMs. *Salmonella* levels in fruits were determined by homogenizing the tissues in a whirl-pak bag containing sterile water. Homogenized materials were serially diluted in sterile water, plated on agar plates, and colony forming units were determined after 24 hrs of incubation at 37° C. Bars: standard deviation; GM: green mature fruit stage; RP: ripened fruit stage; CK: chloramphenicol (2×MBC, 16 μg/ml). *: *Salmonella* population significantly lower than DMSO control (P<0.05); N=15. MBC: minimal bactericidal concentration.
Figure 11B:
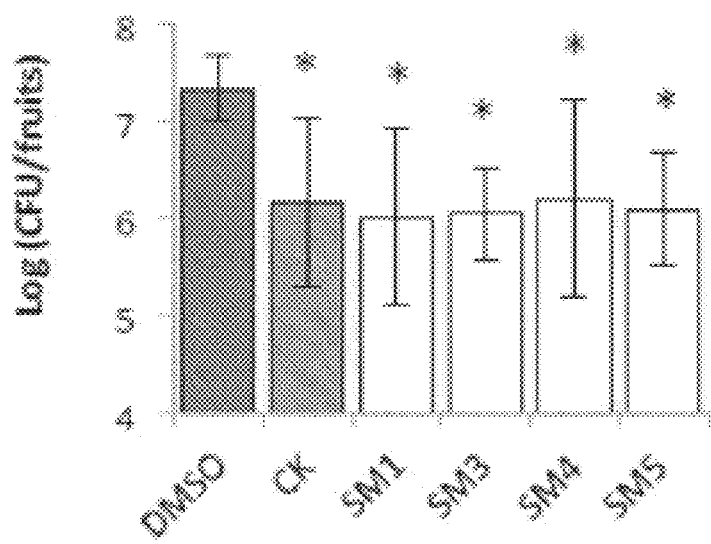
Figure 11C:
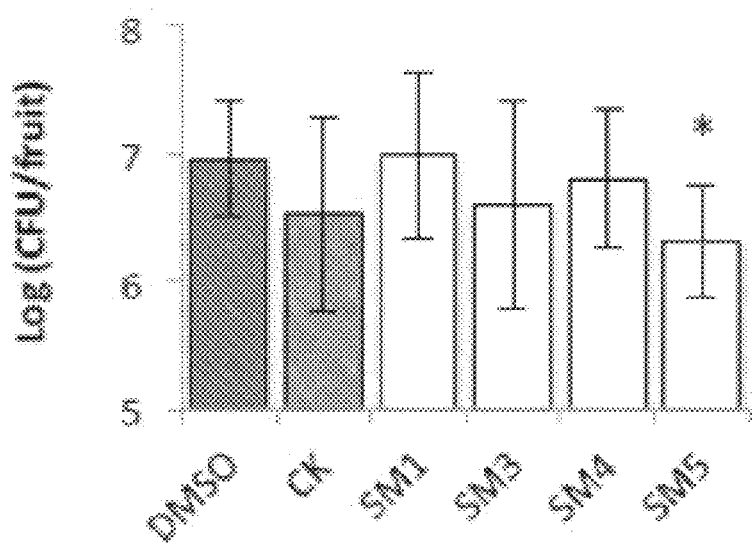
Figure 11D:
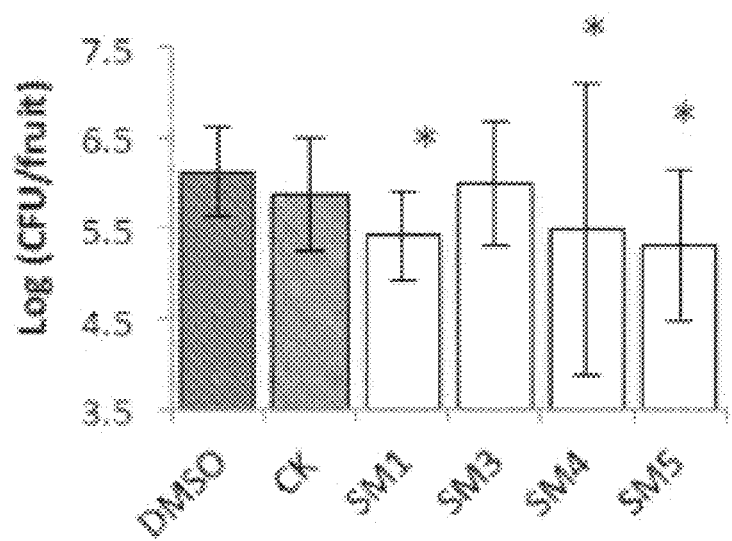
Figure 12A:
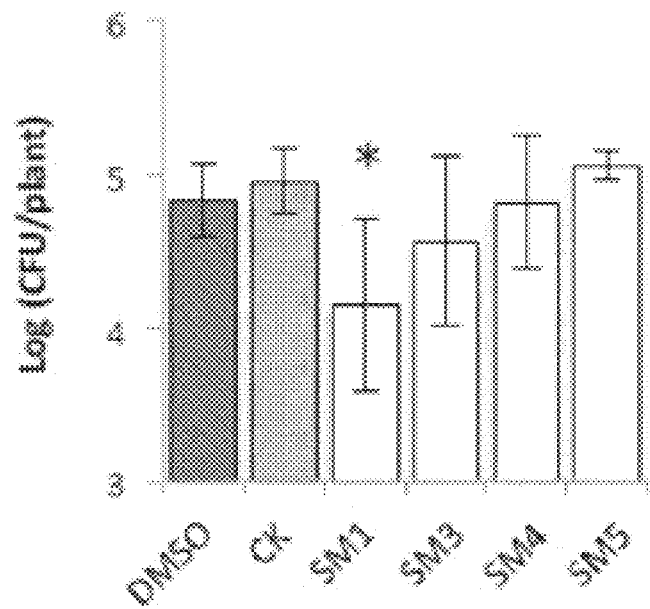
FIGS. 12(A-C). Persistence of wild-type *S. typhimurium* in three-week-old tomato seedlings after treatment with 2×MBC of SMs. SM treatment was performed at -1 DPI (preventative treatment) and 4 DPI (curative treatment) on leaves using a sprayer. *Salmonella* abundance in tomato plants was determined at 1 DPI (FIG. 12A), 3 DPI (FIG. 12B), and 7 DPI (FIG. 12C). *Salmonella* levels in plant tissues were determined by homogenizing the tissues in a whirl-pak bag containing sterile water. Homogenized materials were serially diluted in sterile water, plated on agar plates, and colony forming units were determined after 24 hours of incubation at 37° C. Bars: standard deviation; CK: chloramphenicol (2×MBC, 16 μg/ml); *: *Salmonella* population significantly lower than DMSO control (P<0.05); N=5. DPI: days post-inoculation. MBC: minimal bactericidal concentration.
Figure 12B:
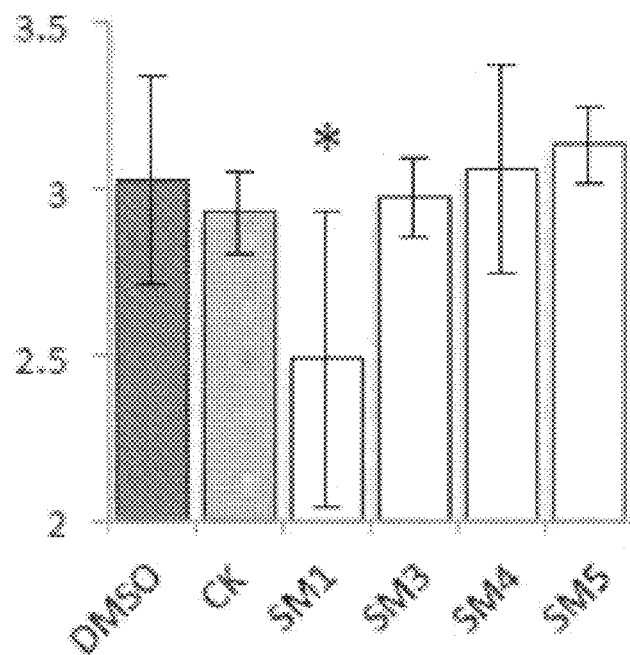
Figure 12C:
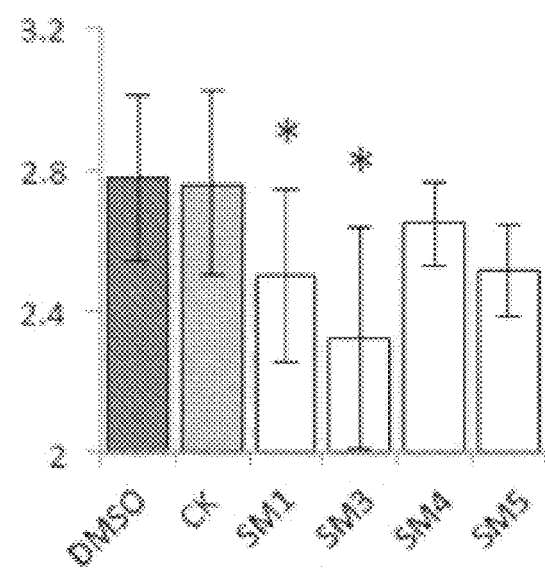

SM4 and SM5 had minimal impact on the cecal microbiota of one-week-old infected broilers: After processing of the reads and taxonomic assignment with the Greengene reference database, 1,155,383 sequences were obtained for a total of 37 samples. The number of reads per samples ranged between 24,748 and 43,688 (mean=31,227). Analysis of the alpha diversity displayed no significant differences in the phylogenetic diversity (FIG. 9A) and richness (FIG. 9B) between chicken groups (P>0.05). However distinct spatial separations of the cecal samples were detected between the NC (non-infected non-treated chickens) group and the five infected chicken groups when the principal coordinate analysis (PCoA) was performed with the unweighted uniFrac data. No clear spatial separation was observed between the DMSO groups and the infected chickens treated with SMs, showing that the presence of either *Salmonella* or DMSO altered the microbiota profile in the ceca (FIG. 9C). This conclusion is supported by a study of the relative microbial abundance at the different taxonomic level.

Figure 6A:
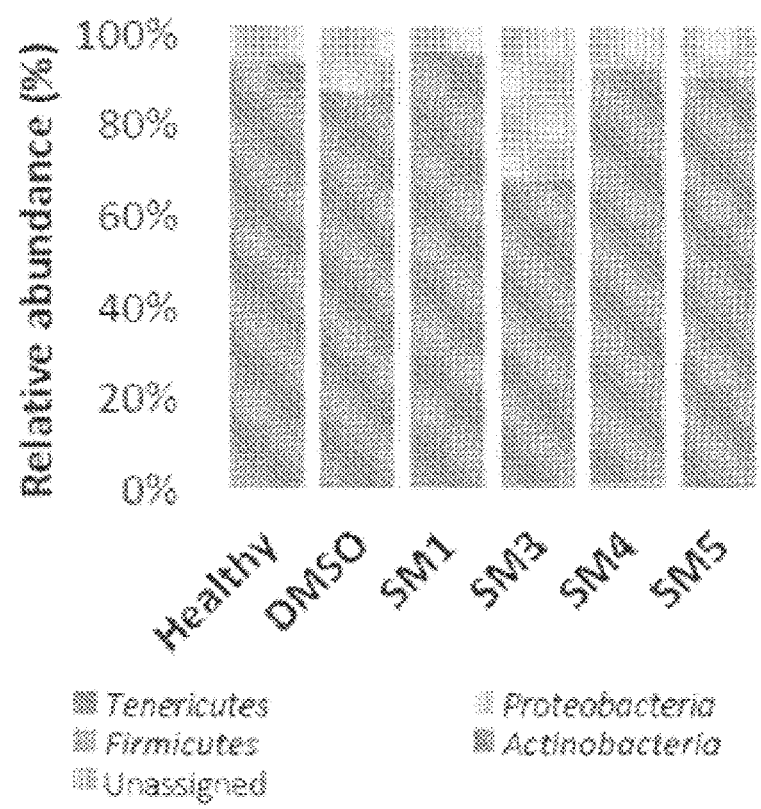
FIG. 6A: Relative abundance at the phylum level.

Firmicutes and Proteobacteria represented the majority of the cecal microbiota with approximately 90% and 10%, respectively (FIG. 6A). A slight increase in Proteobacteria and a decrease in Firmicutes were observed in the DMSO group compared to the NC group. The increase in Proteobacteria was explained by higher abundance in Enterobacteriaceae (2-fold; P<0.01); while the decrease in Firmicutes in the DMSO group was caused by lower abundances in *Clostridium* (25-fold), Ruminococcus (2-fold), *Coprococcus* (2-fold), and a slight decrease of the other Operational Taxonomy Units OTUs in Firmicutes compared to the NC group (P<0.01). However, the DMSO group was also characterized by a significant increase in *Lactobacillus* (663-fold), *R. anaerotruncus* (2.3-fold), *R. rumminococcus* (3.5-fold), and in Coriobacteriaceae (32-fold) compared to the NC group (P<0.01). Details regarding the microbiota diversity is displayed in FIG. 6B.

Different microbiota profiles were also observed at the phylum between the DMSO group and *Salmonella*-infected chickens treated with SMs. Infected chickens treated with SM4 or SM5 had a reduced abundance of *Salmonella* OTUs in ceca, as observed with the bacterial counting (P<0.01; FIG. 5). It was the only OTU significantly affected by SM5 treatment, while SM4 treatment decreased the Ruminococcaceae abundance while increasing Butyricicoccus pullicaecorum compared to the DMSO control (P<0.01) (FIG. 6B). On the other hand, SM1 and SM4 treated chickens displayed more important alteration of the chicken microbiota in ceca. SM1 group had a lower abundance in Proteobacteria and a higher abundance in Firmicutes compared to the DMSO group due to a general increase and decrease of most OTUs in Firmicutes and Proteobacteria, respectively (P<0.01). A reduction in *Salmonella* OTUs was also detected in SM1 treated chickens compared to the DMSO group, which was in discordance with the bacterial counting results (P<0.01; FIG. 5). The difference in sensitivity and specificity of the two techniques used may account for these divergent results. SM1 microbiota was also characterized by a significant decrease in Ruminococcaceae and *Lactobacillus* bacteria. Infected chickens treated with SM3 displayed a lower abundance in Firmicutes compared to DMSO control, which was explained by a general decrease of the Firmicutes OTUs; and an increase in Proteobacteria, which was explained by a significantly higher level of Enterobacteriaceae (2.5-fold) compared to DMSO control (P<0:01) (FIG. 6B). Moreover, the SM3 group was characterized by a significant increase in Leuconostocaceae OTUs (10-fold) and *Clostridium* (15-fold) (P<0.01).

Discussion

The identification of *Salmonella* growth inhibitors was initiated through the screening of 4182 bioactive small molecules (SMs) against *S. typhimurium* LT2 WT at a concentration of 200 µM. During initial steps of the screening, the amount of growth inhibitors identified as well as their antimicrobial activity were increased when bacteria were challenged in minimal growth conditions. SMs with a static effect on *S. typhimurium* in rich growth condition were cidal in minimal growth condition, suggesting nutrient availably is a crucial parameter for *Salmonella* to develop resistance against antimicrobials (17). Nutrients regulate important bacterial physiological processes such as cells division, cell size, and numerous metabolic pathways leading to weaker defense mechanisms when bacteria are in an environment with limited resources (17, 18).

After a battery of tests applied to understand the in vitro limitations of the 19 SMs that totally inhibited *S. typhimurium* growth in minimal growth conditions, four SMs were effective at a low concentration against several *Salmonella* serotypes. However, these SMs also affected the growth of several beneficial bacteria. Only SM5 had a restricted antimicrobial activity among prokaryotes, while the drug targets of SM1, SM3, and SM4, which had high structural similarities between each other, seemed to be more conserved among bacteria (19). These findings confirmed the broad-spectrum activity of imidazole antimicrobial derivatives such as SM1, SM3, and SM4 (20-22). Moreover, a recent study focusing on molecules having high structural similarities with SM3 and SM4 (ionic liquids composed of a hexadecyl group and imidazole derivatives) showed that these molecules could reduce the growth, adhesion, and biofilm formation of algae and disrupted their cell membrane (23). Several ionic liquids are known to have anti-biofilm activities, and due to the similarity of the results obtained in this study, suggests that SM3 and SM4 disrupt *S. typhimurium* cell membranes (21). Concerning SM5, four HTS (PubChem AID #1863, #1981, #2253, and #2401) identified this SM as a direct or indirect inhibitor of the PhoP regulon in *S. typhimurium*; however, its drug target remains unknown.

On the other hand, the four SMs were not pernicious to most eukaryotic cells tested and were able to enter cells to induce antimicrobial effects by clearing internalized *Salmonella* in infected Caco-2, HD11, and THP-1 cells. The *Salmonella* clearance ability of the four SMs in vivo was confirmed using infected *G. mellonella* larvae as model. Several studies described *G. mellonella* as an alternative model to conventional animal test subjects to study infection patterns of foodborne pathogens and to test antimicrobial effectiveness in vivo (14, 24, 25). The application of 12.5 µg of SMs per larva induced low mortality rate in larvae after 72 hrs incubation; and the same concentration of SMs delayed the mortality of infected larvae by reducing *Salmonella* replication inside the larvae. In addition, the four SMs displayed synergetic effects with ciprofloxacin, Cefepime, and Meropenem, which are antibiotics that inhibit DNA replication, cell wall synthesis, and protein synthesis, respectively.

Further, the anti-*Salmonella* effect of the SMs was validated in *Salmonella*-infected one-week-old broiler chickens. Of the four SMs tested, SM4 and SM5 successfully reduced *Salmonella* populations in ceca (up to 2.6-log reduction), and reduced systemic transmission of the pathogen to the liver tissues. Moreover, SM4 and SM5 had minimal impact on the native microbial population in ceca. The microbiome acts as a bridge communicating conditions inside the gut, and also acts as a moderator of metabolism (26, 27). Alteration of gut bacteria diversity influences degradation of complex molecules, production of metabolites, and by consequence modulates resistance of the host toward enteric pathogens. Alternatively, it can change the gut environment, making it more or less challenging for enteric pathogen such as *Salmonella* to colonize it (28-30).

In this study, most of the microbiota variations were detected within the Clostridiales and Lactobacillies orders. *Clostridiales* bacteria are major actors in short chain fatty acid (SCFA) metabolism, resulting in production of butyrate, propionate, or acetic acid (31, 32). These metabolites behave as growth performers or host defense stimulators, and are effective control methods against enteric pathogens in chickens (31-34) (www.lohmann-information.com/content/l_i_42_2007-04_artikel2.pdf). For example, the use of butyrate producers such as Butyricicoccus pullicaecorum or direct application of butyrate in feed are effective methods to control S. *Enteritidis, S. typhimurium, Campylobacter*, and *Clostridium perfringens* infection in chicken broilers (35-37).

Similar results were described for *Lactobacillus*, a bacterium often associated with anti-*Salmonella* properties via the production of bacteriocins (38, 39). Bacteriocins are growth inhibitors of gram-negative bacteria such as *Salmonella* (40). *Lactobacillus* is also involved in the degradation of complex polysaccharides into oligosaccharides. These oligosaccharides could be used in SCFA metabolism (41, 42).

An increase in Leuconastocacede OTUs was also observed in SM5 treated chickens. Little is known about the Leuconostocaceae family; however, they produce acetate and lactate, two subtracts of SCFAs metabolism used by bacteria such as *Butyricicoccus pullicaecorum*. This was supported by a positive correlation between Butyricicoccus and Leuconostocaceae relative abundance in ceca of the SM5 group ($r^2>0.96$) (43). Thus, reduction of *Salmonella* observed in infected chickens treated with SM4 and SM5 could be explained by the anti-*Salmonella* activity of the SMs combined with the growth-promoting effects of the SM4 and SM5 treatment on *Salmonella*-antagonistic microbes such as Leuconostocaceae bacteria, *Lactobacillus*, and *Butyricicoccus pullicaecorum*.

SCFAs metabolites, more importantly butyrate, are important regulators in tight junction proteins (TJP), which are involved in permeability between lumen and hepatic cells. Thus, reduction in systemic colonization of the host observed with SM4- and SM5-treated chickens could be explained by increased SCFAs metabolites that improve intestinal barrier functions (43). This is supported by the microbiota data, in which SM4 had higher relative abundance levels of potential butyrate producers than SM5, and SM4-treated chickens had a lower rate of systemic host colonization than SM5 group.

In summary, two small molecules (SM4 and SM5) effective in controlling *Salmonella* in poultry were identified. Metagenomic data showed the combined effect of butyrate producers against *Salmonella*. However, the use of DMSO to counter the solubility issues with the SMs during the chicken experiment also altered the ceca microbiota, which could explain the higher abundance of *Salmonella* in presence of DMSO.

REFERENCES

1. Painter J A, Hoekstra R M, Ayers T, Tauxe R V, Braden C R, Angulo F J, Griffin P M. 2013. Attribution of Foodborne Illnesses, Hospitalizations, and Deaths to Food Commodities by using Outbreak Data, United States, 1998-2008. Emerg Infect Dis 19:407-415.
2. Rychlik I, Elsheimer-Matulova M, Kyrova K. 2014. Gene expression in the chicken caecum in response to infections with non-typhoid *Salmonella*. Vet Res 45.
3. Antunes P, Mourão J, Campos J, Peixe L. 2016. *Salmonellosis*: the role of poultry meat. Clin Microbiol Infect 22:110-121.
4. Foley S L, Nayak R, Hanning I B, Johnson T J, Han J, Ricke S C. 2011. Population Dynamics of *Salmonella enterica* Serotypes in Commercial Egg and Poultry Production ʸ. Appl Environ Microbiol 77:4273-4279.
5. Mon K K Z, Saelao P, Halstead M M, Chanthavixay G, Chang H-C, Garas L, Maga E A, Zhou H. 2015. *Salmonella enterica* Serovars *Enteritidis* Infection Alters the Indigenous Microbiota Diversity in Young Layer Chicks. Front Vet Sci 2.
6. Basler C, Nguyen T-A, Anderson T C, Hancock T, Behravesh C B. 2016. Outbreaks of Human *Salmonella* Infections Associated with Live Poultry, United States, 1990--2014. Emerg Infect Dis 22:1705-1711.
7. Batz M B, Hoffmann S, Morris J G. 2012. Ranking the disease burden of 14 pathogens in food sources in the United States using attribution data from outbreak investigations and expert elicitation. J Food Prot 75:1278-1291.
8. Martens E, Demain A L. 2017. The antibiotic resistance crisis, with a focus on the United States. J Antibiot (Tokyo) 70:520-526.
9. Xu X, Kumar A, Deblais L, Pina-Mimbela R, Nislow C, Fuchs J R, Miller S A, Rajashekara G. 2015. Discovery of novel small molecule modulators of *Clavibacter michiganensis* subsp. *michiganensis*. Front Microbiol 6.
10. Rajashekara G, Glover D A, Krepps M, Splitter G A. 2005. Temporal analysis of pathogenic events in virulent and avirulent *Brucella melitensis* infections. Cell Microbiol 7:1459-1473.
11. Vrisman C M, Deblais L, Rajashekara G, Miller S A. 2016. Differential Colonization Dynamics of Cucurbit Hosts by *Erwinia tracheiphila*. Phytopathology 106:684-692.
12. Doern C D. 2014. When does 2 plus 2 equal 5? A review of antimicrobial synergy testing. J Clin Microbiol 52:4124-4128.
13. Kumar A, Drozd M, Pina-Mimbela R, Xu X, Helmy Y A, Antwi J, Fuchs J R, Nislow C, Templeton J, Blackall P J, Rajashekara G. 2016. Novel Anti-*Campylobacter* Compounds Identified Using High Throughput Screening of a Pre-selected Enriched Small Molecules Library. Front Microbiol 7.
14. Desbois A P, Coote P J. 2011. Wax moth larva (*Galleria mellonella*): an in vivo model for assessing the efficacy of antistaphylococcal agents. J Antimicrob Chemother 66:1785-1790.
15. Bolger A M, Lohse M, Usadel B. 2014. Trimmomatic: a flexible trimmer for Illumina sequence data. Bioinforma Oxf Engl 30:2114-2120.
16. Caporaso J G, Kuczynski J, Stombaugh J, Bittinger K, Bushman F D, Costello E K, Fierer N, Peña A G, Goodrich J K, Gordon J I, Huttley G A, Kelley S T, Knights D, Koenig J E, Ley R E, Lozupone C A, McDonald D, Muegge B D, Pirrung M, Reeder J, Sevinsky J R, Turnbaugh P J, Walters W A, Widmann J, Yatsunenko T, Zaneveld J, Knight R. 2010. QIIME allows analysis of high-throughput community sequencing data. Nat Methods 7:335-336.
17. Anderl J N, Zahller J, Roe F, Stewart P S. 2003. Role of Nutrient Limitation and Stationary-Phase Existence in *Klebsiella pneumoniae* Biofilm Resistance to Ampicillin and Ciprofloxacin. Antimicrob Agents Chemother 47:1251-1256.
18. Mirzaei M K, Maurice C F. 2017. Menage a trois in the human gut: interactions between host, bacteria and phages. Nat Rev Microbiol 15:397-408.
19. Łuczak J, Jungnickel C, Łącka I, Stolte S, Hupka J. 2010. Antimicrobial and surface activity of 1-alkyl-3-methylimidazolium derivatives. Green Chem 12:593-601.
20. Liu C, Shi C, Mao F, Xu Y, Liu J, Wei B, Zhu J, Xiang M, Li J. 2014. Discovery of New Imidazole Derivatives Containing the 2,4-Dienone Motif with Broad-Spectrum Antifungal and Antibacterial Activity. Molecules 19:15653-15672.
21. Pendleton J N, Gilmore B F. 2015. The antimicrobial potential of ionic liquids: A source of chemical diversity for infection and biofilm control. Int J Antimicrob Agents 46:131-139.

22. Gupta N, Pathak D P. 2011. Synthesis and Evaluation of N-substituted Imidazole Derivatives for Antimicrobial Activity. Indian J Pharm Sci 73:674-678.
23. Reddy G K K, Nancharaiah Y V, Venugopalan V P. 2017. Long alkyl-chain imidazolium ionic liquids: Antibiofilm activity against phototrophic biofilms. Colloids Surf B Biointerfaces 155:487-496.
24. Tsai C J-Y, Loh J M S, Proft T. 2016. *Galleria mellonella* infection models for the study of bacterial diseases and for antimicrobial drug testing. Virulence 7:214-229.
25. Desbois A P, Coote P J. 2012. Utility of Greater Wax Moth Larva (*Galleria mellonella*) for Evaluating the Toxicity and Efficacy of New Antimicrobial Agents. Adv Appl Microbiol 78:25-53.
26. Eisenstein M. 2016. Microbiome: Bacterial broadband. Nature 533: S104-S106.
27. Sonnenburg J L, Bäckhed F. 2016. Diet-microbiota interactions as moderators of human metabolism. Nature 535:56-64.
28. Sekirov I, Finlay B B. 2009. The role of the intestinal microbiota in enteric infection. J Physiol 587:4159-4167.
29. Langdon A, Crook N, Dantas G. 2016. The effects of antibiotics on the microbiome throughout development and alternative approaches for therapeutic modulation. Genome Med 8.
30. Rolhion N, Chassaing B. 2016. When pathogenic bacteria meet the intestinal microbiota. Phil Trans R Soc B 371:20150504.
31. Oakley B B, Lillehoj H S, Kogut M H, Kim W K, Maurer J J, Pedroso A, Lee M D, Collett S R, Johnson T J, Cox N A. 2014. The chicken gastrointestinal microbiome. FEMS Microbiol Lett 360:100-112.
32. Sun Y, O'Riordan MXD. 2013. Regulation of bacterial pathogenesis by intestinal short-chain Fatty acids. Adv Appl Microbiol 85:93-118.
33. van der Wielen P W J J, Bolhuis H, Borin S, Daffonchio D, Corselli C, Giuliano L, D'Auria G, de Lange G J, Huebner A, Varnavas S P, Thomson J, Tamburini C, Marty D, McGenity T J, Timmis K N, BioDeep Scientific Party. 2005. The enigma of prokaryotic life in deep hypersaline anoxic basins. Science 307:121-123.
34. Wielen P W J J van der, Biesterveld S, Notermans S, Hofstra H, Urlings B A P, Knapen F van. 2000. Role of Volatile Fatty Acids in Development of the Cecal Microflora in Broiler Chickens during Growth. Appl Environ Microbiol 66:2536-2540.
35. Fernández-Rubio C, Ordóñez C, Abad-González J, Garcia-Gallego A, Honrubia M P, Mallo J J, Balaña-Fouce R. 2009. Butyric acid-based feed additives help protect broiler chickens from *Salmonella Enteritidis* infection. Poult Sci 88:943-948.
36. Eeckhaut V, Wang J, Van Parys A, Haesebrouck F, Joossens M, Falony G, Raes J, Ducatelle R, Van Immerseel F. 2016. The Probiotic Butyricicoccus pullicaecorum Reduces Feed Conversion and Protects from Potentially Harmful Intestinal Microorganisms and Necrotic Enteritis in Broilers. Front Microbiol 7.
37. Geirnaert A, Steyaert A, Eeckhaut V, Debruyne B, Arends J B A, Van Immerseel F, Boon N, Van de Wiele T. 2014. Butyricicoccus pullicaecorum, a butyrate producer with probiotic potential, is intrinsically tolerant to stomach and small intestine conditions. Anaerobe 30:70-74.
38. Nakphaichit M, Thanomwongwattana S, Phraephaisarn C, Sakamoto N, Keawsompong S, Nakayama J, Nitisinprasert S. 2011. The effect of including *Lactobacillus reuteri* KUB-AC5 during post-hatch feeding on the growth and ileum microbiota of broiler chickens. Poult Sci 90:2753-2765.
39. Pascual M, Hugas M, Badiola J I, Monfort J M, Garriga M. 1999. *Lactobacillus salivarius* CTC2197 Prevents *Salmonella enteritidis* Colonization in Chickens. Appl Environ Microbiol 65:4981-4986.
40. Svetoch E A, Eruslanov B V, Levchuk V P, Perelygin V V, Mitsevich E V, Mitsevich I P, Stepanshin J, Dyatlov I, Seal B S, Stern N J. 2011. Isolation of *Lactobacillus salivarius* 1077 (NRRL B-50053) and Characterization of Its Bacteriocin, Including the Antimicrobial Activity Spectrum v. Appl Environ Microbiol 77:2749-2754.
41. Onrust L, Ducatelle R, Van Driessche K, De Maesschalck C, Vermeulen K, Haesebrouck F, Eeckhaut V, Van Immerseel F. 2015. Steering Endogenous Butyrate Production in the Intestinal Tract of Broilers as a Tool to Improve Gut Health. Front Vet Sci 2.
42. Pryde S E, Duncan S H, Hold G L, Stewart C S, Flint H J. 2002. The microbiology of butyrate formation in the human colon. FEMS Microbiol Lett 217:133-139.
43. Morrison D J, Preston T. 2016. Formation of short chain fatty acids by the gut microbiota and their impact on human metabolism. Gut Microbes 7:189-200.

Example 2. Control of *Salmonella* in Plant Models Using New Generation Small Molecule Inhibitor Phytopathogens are plant pathogens, some of which can decimate yields of commercially important crops. SMs 1, 3, 4, and 5 from Example 1 were tested at a concentration of 200 μM against eleven phytopathogenic bacteria commonly encountered worldwide and with significant economic impact, and twelve beneficial plant bacteria (FIG. 14). All the SMs were cidal for most of the plant pathogens and with no negative growth effect on some of the beneficial plant bacteria tested. Some of the beneficial bacteria have antagonistic growth effect on *Salmonella* as well. Thus, the SMs can be combined with one of these beneficial bacteria to control *Salmonella* in crops.

200 μM SMs showed no detectable toxic effects on tomato seed germination (FIG. 10A) or fruit appearance (FIG. 10D). 200 μM SMs were also non-toxic to tomato seeds (FIG. 10B) and to seedling and plant growth (FIG. 10C).

SM1, SM3, SM4, and SM5 were effective in preventing (up to 95%) *Salmonella* growth in tomato fruits at the green mature (FIG. 11A) and ripened (FIG. 11B) stage when applied as a pretreatment by soaking and spraying the SMs on the fruits before *Salmonella* inoculation. Further, the SMs were effective in reducing (up to 95%) the *Salmonella* population in contaminated tomato fruits at the green mature (FIG. 11C) and ripened (FIG. 11D) stage when applied as a post-inoculation treatment at two-fold their respective minimal bactericidal concentrations (MBC) by soaking and spraying the SMs on the fruits. Moreover, SM1 and SM4 displayed significant reduction (up to 79%) of *Salmonella* persistence on days 1 (FIG. 12A), 3 (FIG. 12B), and 7 (FIG. 12C) post-inoculation in young tomato seedlings when applied by spraying the leaves Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of treating a subject with an avian pathogen comprising administering to the subject an effective amount of a compound having the following formula:

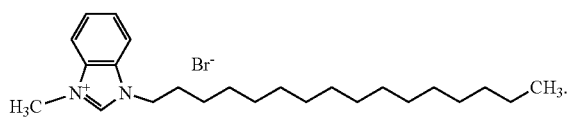

SM4

2. The method of claim 1, wherein the avian pathogen is *Salmonella*.

3. The method of claim 1, wherein the avian pathogen is a *Salmonella enterica* serovar comprising Albany, Anatum, Braenderup, *Enteritidis*, Heidelberg, Javiana, Muenchen, Newport, Saint-Paul, or *Typhimurium*.

4. The method of claim 1, wherein the avian pathogen is *Campylobacter jejuni, Escherichia coli*, or *Mycoplasma gallisepticum*.

5. The method of claim 1, wherein the subject is a mammal.

6. The method of claim 1, wherein the subject is a human.

7. The method of claim 1, wherein the subject is selected from the group consisting of: plant, dog, cow, horse, mouse, rabbit, non-human primate, sheep, goat, cow, pig, turkey, quail, duck, emu, goose, ostrich, pigeon, pheasant, rhea, guineafowl, moth, fly, beetle, ant, spider, butterfly, mosquito, flea, mantis, termite, cricket, grasshopper, bee, caterpillar, and centipede.

8. The method of claim 7, wherein the subject is a poultry subject.

9. The method of claim 7, wherein the subject is a chicken.

10. The method of claim 1, wherein from about 0.01 mg/kg body weight to about 100 mg/kg body weight of the compound are administered to the subject.

11. The method of claim 1, wherein the avian pathogen comprises bacteria arranged in a biofilm.

12. The method of claim 1, further comprising administering an antibiotic selected from ciprofloxacin, cefepime, or meropenem.

13. The method of claim 12, wherein the compound and the antibiotic have a synergistic bactericidal effect.

14. The method of claim 1, wherein the compound does not inhibit growth of at least one cecal microbiota organism selected from the group consisting of *Clostridium clostridioforme, Bacteroides thetaiotaomicron, Bifidobacterium adolescentis, Bifidobacterium longum, Enterococcus faecalis, Lactobacillus brevis*, and *Lactobacillus rhamnosus*.

15. The method of claim 1, wherein the compound promotes growth of a cecal microbiota organism selected from the group consisting of comprising Leuconostocaceae, *Lactobacillus*, and *Butyricicoccus pullicaecorum*.

16. A method of inhibiting an avian pathogen in a subject comprising administering to the subject a compound having the following formula:

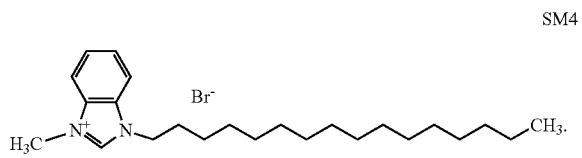 [SMILES: CCCCCCCCCCCCCCCCn1c[n+](C)c2ccccc21 ; [Br-]]

SM4

17. The method of claim 16, wherein the subject is a poultry subject.

18. The method of claim 16, wherein the compound is administered to the subject orally.

19. The method of claim 16, wherein the compound is administered to the subject in feed product.

20. The method of claim 16, wherein the avian pathogenies selected from the group consisting of Avian Pathogenic *Escherichia coli* (APEC) *Campylobacter jejuni, Salmonella* spp., and *Mycoplasma gallisepticum*.

21. A method of inhibiting *Salmonella* infection in a subject comprising administering to the subject a compound having the following formula:

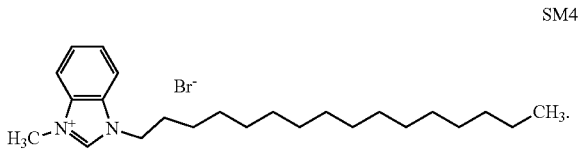 [SMILES: CCCCCCCCCCCCCCCCn1c[n+](C)c2ccccc21 ; [Br-]]

SM4

22. A method of claim 21, wherein the subject is selected from the group consisting of plant, human, dog, cow, horse, mouse, rabbit, non-human primate, sheep, goat, cow, pig, chicken, turkey, quail, duck, emu, goose, ostrich, pigeon, pheasant, rhea, guineafowl, moth, fly, beetle, ant, spider, butterfly, mosquito, flea, mantis, termite, cricket, grasshopper, bee, caterpillar, and centipede.

23. A method of claim 21, wherein the subject is selected from the group consisting of subsistence crop, commercial crop, and cash crop.

24. A method of claim 21, wherein the subject is selected from the group consisting of Solanaceae seed, Solanaceae plant, and Solanaceae plant part.

* * * * *